US012559471B2

(12) United States Patent
Xu et al.

(10) Patent No.: US 12,559,471 B2
(45) Date of Patent: Feb. 24, 2026

(54) 1,5-DIHYDRO-2,4-BENZODIAZEPINE-3-ONE DERIVATIVE AND APPLICATION THEREOF

(71) Applicant: JIANGSU NHWA PHARMACEUTICAL CO., LTD, Jiangsu (CN)

(72) Inventors: Xiangqing Xu, Jiangsu (CN); Yinli Qiu, Jiangsu (CN); Qiang Guo, Jiangsu (CN); Minquan Yu, Jiangsu (CN); Song Zhao, Jiangsu (CN); Quxiang Li, Jiangsu (CN); Peng Jing, Jiangsu (CN); Yuanyuan Hou, Jiangsu (CN); Yingying Dong, Jiangsu (CN); Guosheng Wu, Jiangsu (CN); Shuang Zhang, Jiangsu (CN); Aijun Lu, Jiangsu (CN)

(73) Assignee: JIANGSU NHWA PHARMACEUTICAL CO., LTD, Jiangsu (CN)

( * ) Notice: Subject to any disclaimer, the term of this patent is extended or adjusted under 35 U.S.C. 154(b) by 627 days.

(21) Appl. No.: 18/048,340

(22) Filed: Oct. 20, 2022

(65) Prior Publication Data

US 2023/0132621 A1 May 4, 2023

Related U.S. Application Data

(63) Continuation-in-part of application No. PCT/CN2021/089660, filed on Apr. 25, 2021.

(30) Foreign Application Priority Data

Apr. 26, 2020 (CN) ........................ 202010330893.1
Mar. 17, 2021 (CN) ........................ 202110288141.8

(51) Int. Cl.

| | |
|---|---|
| ***C07D 243/04*** | (2006.01) |
| ***A61K 31/551*** | (2006.01) |
| ***A61P 25/16*** | (2006.01) |
| ***A61P 25/18*** | (2006.01) |
| ***C07D 401/04*** | (2006.01) |
| ***C07D 401/14*** | (2006.01) |
| ***C07D 403/14*** | (2006.01) |
| ***C07D 471/04*** | (2006.01) |
| ***C07D 471/10*** | (2006.01) |

(52) U.S. Cl.

CPC ............ *C07D 401/04* (2013.01); *A61P 25/16* (2018.01); *A61P 25/18* (2018.01); *C07D 401/14* (2013.01); *C07D 403/14* (2013.01); *C07D 471/04* (2013.01); *C07D 471/10* (2013.01)

(58) Field of Classification Search

CPC .. C07D 243/04; C07D 401/04; A61K 31/551; A61K 31/55; A61P 25/18; A61P 25/16; A61P 25/28

USPC ..................... 540/500, 543; 514/221, 212.02

See application file for complete search history.

(56) References Cited

U.S. PATENT DOCUMENTS

2019/0031605 A1 1/2019 Watanabe et al.

FOREIGN PATENT DOCUMENTS

| | | | |
|---|---|---|---|
| CN | 1215054 | A | 4/1999 |
| CN | 101304980 | A | 11/2008 |
| CN | 103702983 | A | 4/2014 |
| WO | 8502843 | A1 | 7/1985 |
| WO | 9738984 | A1 | 10/1997 |
| WO | 0102358 | A2 | 1/2001 |
| WO | 2005082859 | A1 | 9/2005 |
| WO | 2007011820 | A2 | 1/2007 |
| WO | 2008132139 | A2 | 11/2008 |
| WO | 2009013212 | A2 | 1/2009 |

OTHER PUBLICATIONS

Tian, Chao et al.; "Pharmacological and Clinical Evaluation of Pimavanserin in the Treatment of Psychosis in Parkinson's Disease"; Clinical Medication Journal; vol. 15, No. 11; Nov. 15, 2017; ISSN: 1672-3384; pp. 15-19.

*Primary Examiner* — Charanjit Aulakh
(74) *Attorney, Agent, or Firm* — NKL Law; Allen Xue

(57) ABSTRACT

1,5-dihydro-2,4-benzodiazepine-3-one derivatives, such as a compound represented by formula I, acts on 5-$HT_{2A}$ and 5-$HT_{2C}$ receptors. The selectivity for 5-$HT_{2A}$ is superior or similar to pimavanserin. The derivative is used for treating schizophrenia or Parkinson's disease, dementia-related behavioral disorders, and psychosis. The antipsychotic activity of the compound is equivalent to that of pimavanserin, the side effects of sedation and worsening of exercise are less than those of pimavanserin, and cardiotoxicity is less than that of pimavanserin.

I

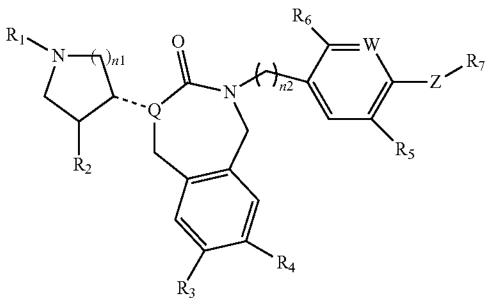

13 Claims, 1 Drawing Sheet

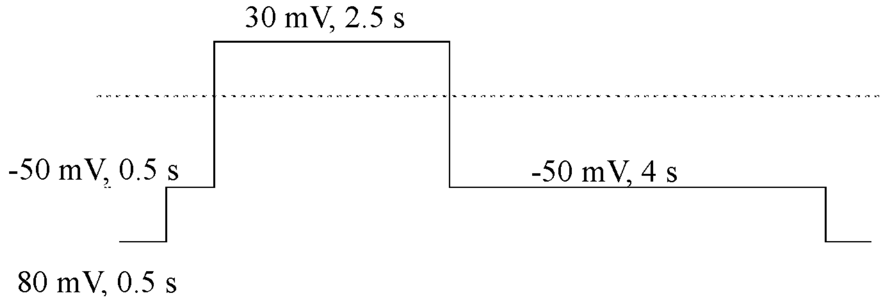
30 mV, 2.5 s
-50 mV, 0.5 s
-50 mV, 4 s
80 mV, 0.5 s

1,5-DIHYDRO-2,4-BENZODIAZEPINE-3-ONE DERIVATIVE AND APPLICATION THEREOF

CROSS-REFERENCE TO RELATED APPLICATIONS

The is a continuation-in-part application of PCT International Application No. PCT/CN2021/089660, filed on Apr. 25, 2021, which claims the priority to Chinese Patent Application No. 202010330893.1 entitled with "1,5-dihydro-2,4-benzodiazepine-3-one derivative and application thereof" filed on Apr. 26, 2020, and Chinese Patent Application No. 202110288141.8 entitled with "1,5-dihydro-2,4-benzodiazepine-3-one derivative and application thereof" filed on Mar. 17, 2021, the content of each is incorporated herein by reference in its entirety.

TECHNICAL FIELD

The present invention relates to the field of pharmaceutical chemistry, particularly relates to a 1,5-dihydro-2,4-benzodiazepine-3-one derivative and application thereof.

BACKGROUND

Schizophrenia is insidious in onset, low in treatment rate and high in lifetime prevalence rate. Currently, about 0.3%-0.7% of the world's population is affected by schizophrenia in their lifetime, with over 21 million people estimated to be living with schizophrenia globally in 2016. At present, anti-schizophrenic drugs mainly include typical anti-schizophrenic drugs and atypical anti-schizophrenic drugs. However, the current schizophrenia therapeutic drugs will cause adverse reactions such as extrapyramidal symptoms (EPS), tardive dyskinesia and prolactin increase due to their strong blocking of dopamine receptors. In the medical field, although there are many types of active compounds acting on different targets available for the treatment of sleep disorders, adverse reactions such as addiction susceptibility, drug resistance and sequelae effects are still unsolved issues.

Antipsychotic drugs that exert pharmacological effects by blocking dopamine $D_2$ receptors have traditionally been referred to as the first generation antipsychotic drugs, i.e., "typical" antipsychotic drugs (e.g., haloperidol), which are groundbreaking in treating positive symptoms of schizophrenia but fail to treat negative symptoms and cognitive disorder. Typical antipsychotic drugs generally have severe EPS side effects and are ineffective in one third of schizophrenic patients.

After 1960s, a series of new generation antipsychotic drugs, including ziprasidone, risperidone, etc., were developed in succession and referred to as the second generation antipsychotic drugs, i.e., novel antipsychotic drugs. Although their respective pharmacological effects are not completely identical, they share the common pharmacological characteristic that the affinity for 5-hydroxytryptamine (5-HT) receptors (5-HT1A, 2A, and 2C) and norepinephrine (NA) receptors ($\alpha$1 and $\alpha$2) is much higher than for a $D_2$ receptor, resulting in a lower ratio of $D_2$/5-$HT_{2A}$. Compared with the first generation antipsychotic drugs, the second generation antipsychotic drugs has more advantages in clinical effects, not only are they as effective as traditional antipsychotic drugs for positive symptoms, but they are also effective for negative symptoms and cognitive disorder symptoms and have a broader spectrum of action. However, these drugs have adverse reactions such as QT interval prolongation, hyperprolactinemia, and weight gain. Therefore, it is a research hotspot to find drugs that are effective for positive and negative symptoms and cognitive disorder of schizophrenia and have small side effects.

The 5-hydroxytryptamine system plays an important role in regulating the functions of the prefrontal cortex (PFC), including emotion control, cognitive behavior, and working memory. The pyramidal neurons and GABA interneurons of PFC comprise several 5-hydroxytryptamine receptor subtypes with particularly high density, including 5-HTA and 5-$HT_{2A}$. It has recently been demonstrated that the PFC and NMDA receptor channels are targets for 5-$HT_{1A}$R, and that these two receptors regulate cortical excitatory neurons and thus affect cognitive function. In fact, various preclinical data suggest that 5-$HT_{1A}$R may be a new target for the development of antipsychotics. The high affinity (such as olanzapine and aripiprazole) for 5-$HT_{1A}$R and low EPS side effects of atypical antipsychotic drugs suggest that the 5-hydroxytryptamine system plays an important role in regulating the functions of the prefrontal cortex (PFC), including emotion control, cognitive behavior, and working memory. The pyramidal neurons and GABA interneurons of PFC comprise several 5-hydroxytryptamine receptor subtypes with particularly high density, including 5-$HT_{1A}$ and 5-$HT_{2A}$. Recent studies have shown that 5-HTA agonists are associated with atypical antipsychotic therapy and can ameliorate negative symptoms and cognitive disorder. In the treatment of schizophrenia with the atypical antipsychotic drug clozapine, 5-$HT_{2A}$ has been found to play a major role, involving various aspects of perception, emotion regulation and motion control. Blocking of the 5-$HT_{2A}$ receptor will normalize the release of dopamine, which plays an antipsychotic role. In addition, the 5-$HT_{2C}$ receptor is closely associated with weight gain.

Pimavanserin is an inverse agonist with high affinity for 5-$HT_{2A}$ and 5-$HT_{2C}$. In vitro experimental results show that pimavanserin has higher affinity for 5-$HT_{2A}$ receptor [inhibition constant (Ki)=0.4 nM] than for the 5-$HT_{2C}$ receptor (Ki=16 nM), and has no significant affinity for the 5-$HT_{2B}$ receptor, dopamine receptor (including $D_2$ receptor), adrenergic receptor, muscarinic receptor or calcium channel receptor (Ki>300 nM). Pimavanserin has been approved for marketing by the U.S. Food and Drug Administration in April 2016 under the trade name Nuplazid™, and is mainly used for treating Parkinson's psychiatric symptoms such as hallucinations and delusions.

Therefore, there is a need to find an anti-schizophrenic drug that is effective for both positive and negative symptoms, and can ameliorate cognitive disorder in addition to preventing extrapyramidal side effects, including tardive dyskinesia and Parkinson's disease; and that can reduce weight gain.

SUMMARY

The present invention is intended to solve at least one of the problems present in the prior art. For this purpose, it is an object of the present invention to provide a compound represented by formula I: a compound represented by formula I:

I

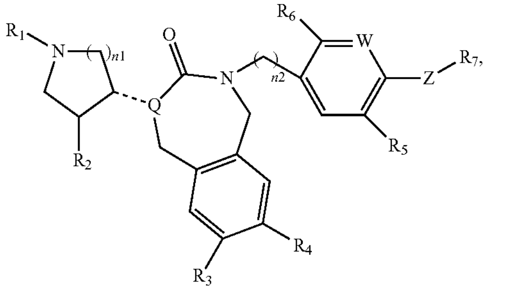

wherein in formula I: n1 and n2 are integers of 1-3;

R1 is selected from C1-C8 linear or branched alkyl, C2-C8 alkenyl, and C2-C8 alkynyl, wherein the alkyl, alkenyl and alkynyl are each independently and optionally substituted with substituents selected from halogen and C1-C8 haloalkyl;

R2 is selected from hydrogen, halogen and C1-C8 haloalkyl;

R3, R4, R5 and R6 are each independently selected from hydrogen, halogen and C1-C8 haloalkyl;

R7 is selected from C1-C5 linear or branched alkyl, cycloalkyl and R9,

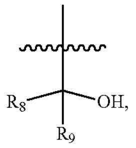

wherein R8 and R9 are each independently selected from C1-C8 linear or branched alkyl, and the alkyl and cycloalkyl are optionally substituted with substituents selected from halogen and C1-C8 haloalkyl;

Z is selected from C, O and N;

Q and W are each selected from C and N; and bond ------ represents that the bond is absent or is present as a single bond;

when the bond ------ represents that the bond is absent, the compound represented by formula I is a compound represented by formula II:

II

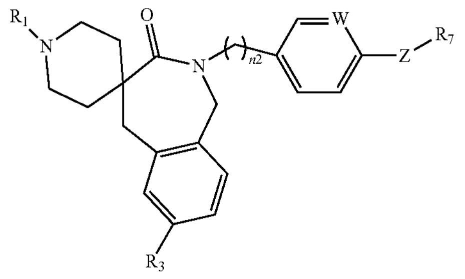

in formula II, n2, R1, R3, R7, W and Z are as defined above; or when the bond ------ represents that the bond is present as a single bond, the compound represented by formula I is a compound represented by formula III:

III

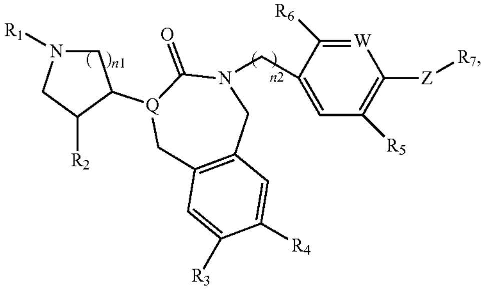

in formula III, n1 and n2 are integers of 1-3;

R1 is selected from C1-C8 linear or branched alkyl, C2-C8 alkenyl, and C2-C8 alkynyl, wherein the alkyl, alkenyl and alkynyl are optionally substituted with substituents selected from halogen and C1-C8 haloalkyl;

R2 is selected from hydrogen and halogen;

R3, R4, R5 and R6 are each independently selected from hydrogen, halogen and haloalkyl;

R7 is selected from C1-8 linear or branched alkyl, cycloalkyl and

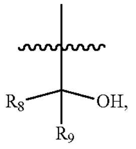

wherein R8 and R9 are each independently selected from C1-C8 linear or branched alkyl, and the alkyl and cycloalkyl are optionally substituted with substituents selected from halogen and C1-C8 haloalkyl;

Z is selected from C, O and N; and

Q and W are each selected from C and N.

In an embodiment, the C1-C8 linear or branched alkyl is selected from C1-C5 linear or branched alkyl and C1-C3 linear or branched alkyl; and/or the C2-C8 alkenyl is C2-C5 alkenyl; and/or the C2-C8 alkynyl is C2-C5 alkynyl; and/or the haloalkyl is C1-C5 haloalkyl; and/or the cycloalkyl is C3-C10 cycloalkyl, preferably C3-C6 cycloalkyl.

In another aspect, the present invention provides a pharmaceutical composition comprising a therapeutically effective amount of the compound represented by formula I described above, and optionally further comprising a pharmaceutically acceptable excipient, carrier, adjuvant or vehicle or a combination thereof.

In another aspect, the present invention provides use of the compound represented by formula I and a pharmaceutical composition thereof in preparing a medicament for treating a psychiatric disease.

In an embodiment, the psychiatric disease is schizophrenia and psychosis.

In another embodiment, the psychiatric disease is Parkinson's disease, behavioral and psychological symptom of dementia.

BRIEF DESCRIPTION OF THE DRAWING

The FIGURE shows the voltage stimulation scheme for cellular hERG potassium current.

DETAILED DESCRIPTION

Unless otherwise defined, all technical and scientific terms used herein have the same meaning as that commonly understood by one of ordinary skill in the art to which the present invention belongs. In the event of a contradiction, the definition provided in the present application will control. When referring to a trade name, it is intended to refer to its corresponding commercial product or its active ingredient. All patents, published patent applications and publications cited herein are incorporated herein by reference.

General Terms and Definitions

The term "comprise", "comprises" or "comprising" is an open-ended expression, i.e., including what is meant by the present invention, but not excluding other aspects. It should be understood that the term "comprise", "comprises" or "comprising" may encompass the meaning in a closed-end language, i.e., "consist(s) of . . . /consisting of . . . ".

As described herein, the compound of the present invention such as the compound of general formula above or instances and subclasses as specified in the examples may optionally be substituted with one or more substituents. It should be understood that the term "optionally substituted" is used interchangeably with the term "substituted or unsubstituted". In general, the term "substituted" means that one or more hydrogen atoms in a given structure are replaced with a particular substituent, with the proviso that the normal valency of the atom specified is not exceeded and that the replacement results in a stable compound. A combination of substituents and/or variables is permissible only if the combination results in a stable compound. When it is stated that a certain substituent is absent, it should be understood that the substituent may be one or more hydrogen atoms, provided that the structure enables the compound to reach a stable state. Unless otherwise indicated, the substitution of a substituent may occur at various substitutable positions/sites of the substituted group. When more than one position/site in a given structure can be substituted with one or more substituents selected from particular groups, the substitution of the substituents may occur at various positions/sites, identically or differently.

Unless otherwise indicated, as used herein, the attachment point of a substituent may be from any suitable position/site of the substituent. When a bond of a substituent is shown to pass through a bond connecting two atoms in a ring, the substituent may be bonded to any one of the ring-forming atoms in the substitutable ring.

In addition, it should be noted that unless otherwise explicitly indicated, the description "be each independently" used in the present invention should be understood in a broad sense, and it may mean that specific items expressed by the same symbol in different groups do not affect each other, or that specific items expressed by the same symbol in the same group do not affect each other.

When the lower and upper limits of a range of values are disclosed, any value falling within the range and any included range are specifically disclosed. In particular, each range of values disclosed herein is to be understood as indicating each value and range encompassed within the broader range. When any variable (e.g., R), as well as labeled variables (e.g., R1, R2, R3, R4, R5, R6, R7, etc.) occurs more than once in a composition or structure of a compound, the variable is independently defined in each case at each occurrence. For example, if a group is substituted with 0, 1, 2, 3 or 4 R substituents, the group can be optionally substituted with up to four R substituents, and each option for R substituent is independently defined in each case.

In each part of this specification, substituents for the disclosed compounds are disclosed according to group types or ranges. It is specifically noted that each separate sub-combination of the various members of these group types and ranges is encompassed in the present invention. For example, the expression "m-n" as used herein refers to the range of m to n as well as to sub-ranges consisting of point values therein and the point values. For example, the term "C1-C5 alkyl" refers specifically to independently disclosed methyl, ethyl, C3 alkyl, C4 alkyl and C5 alkyl. Examples of the alkyl group include, but are not limited to, methyl (Me, $-CH_3$), ethyl (Et, $-CH_2CH_3$), n-propyl (n-Pr, $-CH_2CH_2CH_3$), isopropyl (i-Pr, $-CH(CH_3)_2$), n-butyl (n-Bu, $-CH_2CH_2CH_2CH_3$), isobutyl (i-Bu, $-CH_2CH(CH_3)_2$), sec-butyl (s-Bu, $-CH(CH_3)CH_2CH_3$), tert-butyl (t-Bu, $-C(CH_3)_3$), n-pentyl ($-CH_2CH_2CH_2CH_2CH_3$), 2-pentyl ($-CH(CH_3)CH_2CH_2CH_3$), 3-pentyl ($-CH(CH_2CH_3)_2$), 2-methyl-2-butyl ($-C(CH_3)_2CH_2CH_3$), 3-methyl-2-butyl ($-CH(CH_3)CH(CH_3)_2$), 3-methyl-1-butyl ($-CH_2CH_2CH(CH_3)_2$), 2-methyl-1-butyl ($-CH_2CH(CH_3)CH_2CH_3$), etc. For example, the expression "C2-C8" or "C2-8" encompasses a range of 2-8 carbon atoms and should be understood as also encompassing any sub-range and each point value therein, e.g., C2-C5, C3-C4, C2-C6, C3-C6, C4-C6, C4-C7, C4-C8, C2-C5, etc., and C2, C3, C4, C5, C6, C7, C8, etc. For example, the expression "C3-C10" or "C3-10" should also be understood in a similar manner, for example, it can encompass any sub-range and point value therein, e.g., C3-C9, C6-C9, C6-C8, C6-C7, C7-C10, C7-C9, C7-C8, C8-C9, etc., and C3, C4, C5, C6, C7, C8, C9, C10, etc. For another example, the expression "C1-C5" or "C1-5" encompasses a range of 1-5 carbon atoms and should be understood as also encompassing any sub-range and each point value therein, e.g., C2-C5, C3-C4, C1-C2, C1-C3, C1-C4, C1-C5, etc., and C1, C2, C3, C4, C5, etc. For another example, the expression "C2-C5" or "C2-5" encompasses a range of 2-5 carbon atoms and should be understood as also encompassing any sub-range and each point value therein, e.g., C2-C5, C3-C4, C2-C3, C2-C4, C3-C5, C4-C5, etc., and C2, C3, C4, C5, etc. For another example, the expression "C3-C6" or "C3-6" encompasses a range of 3-6 carbon atoms and should be understood as also encompassing any sub-range and each point value therein, e.g., C3-C5, C3-C4, C3-C6, C5-C6, C4-C6, C4-C5, etc., and C3, C4, C5, C6, etc. For another example, the expression "C1-C8" or "C1-8" encompasses a range of 1-8 carbon atoms and should be understood as also encompassing any sub-range and each point value therein, e.g., C2-C5, C3-C4, C2-C6, C3-C6, C4-C6, C4-C7, C4-C8, C2-C5, etc., and C1, C2, C3, C4, C5, C6, C7, C8, etc. For another example, the expression "three to ten membered" should be understood as encompassing any sub-range and each point value therein, e.g., three to five membered, three to six membered, three to seven membered, three to eight membered, four to five membered, four to six membered, four to seven membered, four to eight membered, five to seven membered, five to eight membered, six to seven membered, six to eight membered, nine to ten membered, etc., and three membered, four membered, five membered, six membered, seven membered, eight membered, nine membered, ten membered, etc. Other similar expressions herein should also be understood in a similar manner.

A range (e.g., numerical range) recited herein may encompass each value in the range and each sub-range formed by the values. Therefore, for example, the expression "n2 is any integer between 0 and 3", includes, for example, any integer of 0-2, any integer of 2-3, etc., e.g., 1, 2 or 3.

The term "one or more" or the similar expression "at least one" may indicate, for example, 1, 2, 3, 4, 5, 6, 7, 8, 9, 10 or more.

The term "selected from . . . " refers to the independent selection of one or more elements in a group listed below, and may include a combination of two or more elements.

When it is stated that each carbon atom in a group may optionally be replaced by a heteroatom, the proviso is that the normal valency of all atoms in the group in the present case is not exceeded, and that a stable compound is formed.

The term "hydrogen (H)" refers to a single hydrogen atom. Such a radical may be connected to other groups, such as to an oxygen atom, to form a hydroxyl group.

The term "halogen" or "halo" should be understood to refer to fluorine (F), chlorine (Cl), bromine (Br) or iodine (I), preferably fluorine, chlorine, bromine atoms, more preferably a fluorine atom.

The term "alkyl" refers to a linear or branched saturated aliphatic hydrocarbon group consisting of carbon atoms and hydrogen atoms, which is connected to the rest of the molecule by a single bond.

The "alkyl" may have 1-5 carbon atoms, that is, it may be "C1-C5 alkyl", e.g., C1-4 alkyl, C1-3 alkyl, C1-2 alkyl, C3 alkyl, C4 alkyl, C1-5 alkyl, or C3-5 alkyl. The alkyl may also have 1-3 carbon atoms, that is, it may be "C1-C3 alkyl", e.g., C1-3 alkyl, C1-2 alkyl, or C3 alkyl. For another example, the term "C1-C5 alkyl" refers specifically to independently disclosed methyl, ethyl, C3 alkyl, C4 alkyl and C5 alkyl. Examples of the alkyl group include, but are not limited to, methyl (Me, $—CH_3$), ethyl (Et, $—CH_2CH_3$), n-propyl (n-Pr, $—CH_2CH_2CH_3$), isopropyl (i-Pr, $—CH(CH_3)_2$), n-butyl (n-Bu, $—CH_2CH_2CH_2CH_3$), isobutyl (i-Bu, $—CH_2CH(CH_3)_2$), sec-butyl (s-Bu, $—CH(CH_3)CH_2CH_3$), tert-butyl (t-Bu, $-C(CH_3)_3$), n-pentyl ($—CH_2CH_2CH_2CH_2CH_3$), 2-pentyl ($—CH(CH_3)CH_2CH_2CH_3$), 3-pentyl ($—CH(CH_2CH_3)_2$), 2-methyl-2-butyl ($—C(CH_3)_2CH_2CH_3$), 3-methyl-2-butyl ($—CH(CH_3)CH(CH_3)_2$), 3-methyl-1-butyl ($—CH_2CH_2CH(CH_3)_2$), 2-methyl-1-butyl ($—CH_2CH(CH_3)CH_2CH_3$), n-hexyl ($—CH_2CH_2CH_2CH_2CH_2CH_3$), 2-hexyl ($—CH(CH_3)CH_2CH_2CH_2CH_3$), 3-hexyl ($—CH(CH_2CH_3)(CH_2CH_2CH_3)$), 2-methyl-2-pentyl ($—C(CH_3)_2CH_2CH_2CH_3$), 3-methyl-2-pentyl ($—CH(CH_3)CH(CH_3)CH_2CH_3$), 4-methyl-2-pentyl ($—CH(CH_3)CH_2CH(CH_3)_2$), 3-methyl-3-pentyl ($—C(CH_3)(CH_2CH_3)_2$), 2-methyl-3-pentyl ($—CH(CH_2CH_3)CH(CH_3)_2$), 2,3-dimethyl-2-butyl ($—C(CH_3)_2CH(CH_3)_2$), 3,3-dimethyl-2-butyl ($—CH(CH_3)C(CH_3)_3$), n-heptyl, n-octyl, etc.

The term "alkenyl" refers to a linear or branched unsaturated aliphatic hydrocarbyl group consisting of carbon atoms and hydrogen atoms with at least one double bond. The alkenyl may have 2-5 carbon atoms, that is, it may be "C2-s alkenyl", e.g., C2-4 alkenyl, or C3-4 alkenyl. Non-limiting examples of the alkenyl group include, but are not limited to, vinyl, allyl, (E)-2-methylvinyl, (Z)-2-methylvinyl, (E)-but-2-enyl, (Z)-but-2-enyl, (E)-but-1-enyl, (Z)-but-1-enyl, etc.

The term "cycloalkyl" refers to a saturated cyclic hydrocarbon group consisting of carbon atoms and hydrogen atoms, preferably containing 1 or 2 rings. The cycloalkyl may be of a monocyclic, fused polycyclic, bridged cyclic or spiro cyclic structure. The cycloalkyl may have 3-6 carbon atoms, that is, it may be "$C_3$-$C_6$ cycloalkyl", e.g., $C_6$ cycloalkyl, $C_5$ cycloalkyl, $C_4$ cycloalkyl, or $C_3$ cycloalkyl. Non-limiting examples of the cycloalkyl group include, but are not limited to, cyclopropyl, cyclobutyl, cyclopentyl, cyclohexyl, etc. The term also encompasses the case where the C atom may be substituted with oxo (=O).

The term "alkynyl" refers to a linear or branched unsaturated aliphatic hydrocarbyl group consisting of carbon atoms and hydrogen atoms with at least one triple bond. The alkynyl may have 2-5 carbon atoms, that is, it may be "$C_{2-5}$ alkynyl", e.g., $C_{2-3}$ alkynyl or $C_{2-4}$ alkynyl. Non-limiting examples of the alkynyl group include, but are not limited to, ethynyl, prop-1-ynyl, prop-2-ynyl, but-1-ynyl, but-2-ynyl, but-3-ynyl, etc.

A "---" bond refers to any one of the cases where the bond is a single bond "—" or is absent.

When it is stated that a certain chemical bond is absent, it should be understood that only one of the two atoms to which the chemical bond connects is present and provided that the structure of a compound reaches a stable state, the atom is connected to the atom of the other moiety of the structure which is connected to the two atoms to which the original chemical bond connects.

Herein, when it is described that the bond "---" in formula I is absent, only a carbon atom of the carbon atom and Q atom at both ends of the bond "---" is present, and provided that the structure of the compound reaches a stable state, the present carbon atom is connected to the atoms of the other moiety of the structure, to form the compound represented by formula II

II

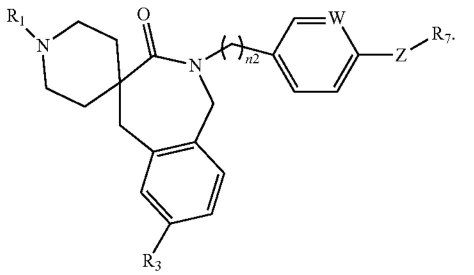

The term "pharmaceutically acceptable" substance refers to those substances which are, within the scope of sound medical judgment, suitable for use in contact with the tissues of patients without undue toxicity, irritation, allergic response and other problems, commensurate with a reasonable benefit to risk ratio, and effective for their intended use.

The term "pharmaceutically acceptable carrier" refers to those substances which do not have a significant irritating effect on organisms and do not impair the biological activity and properties of the active compound. The "pharmaceutically acceptable carrier" includes, but is not limited to a glidant, a sweetener, a diluent, a preservative, a dye/colorant, a flavoring agent, a surfactant, a wetting agent, a dispersant, a disintegrant, a stabilizer, a solvent or an emulsifier.

The terms "administration" or "administering" and the like refer to methods those enable a compound or composition to be delivered to a desired site of biological action. Those methods include, but are not limited to, oral administration or parenteral (including intraventricular, intravenous, subcutaneous, intraperitoneal, intramuscular, intravascular injection or infusion), topical, rectal administrations, and the like. Those methods especially include injection or oral administration.

As used herein, the term "treat", "treating" or "treatment" includes alleviating, reducing, or ameliorating a disease or symptom; preventing other symptoms; ameliorating or preventing metabolic factors underlying a symptom; inhibiting a disease or symptom, e.g., arresting the development of a disease or symptom; alleviating a disease or symptom; promoting the alleviation of a disease or symptom; or halting the signs of a disease or symptom, and extends to include prevention. The "treat", "treating" or "treatment" also includes achieving a therapeutic benefit and/or a prophylactic benefit. The therapeutic benefit refers to eradication or amelioration of a condition being treated. In addition, the therapeutic benefit is achieved by eradicating or ameliorating one or more physiological signs associated with the underlying disease, and amelioration of an underlying disease in the subject is observed, although the subject may still be afflicted with the underlying disease. The prophylactic benefit refers to the use of a composition by a patient to prevent the risk of a disease or the administration of a composition by a patient when the patient develops one or more physiological conditions of a disease, although the disease has not yet been diagnosed.

The term "active ingredient", "therapeutic agent", "active substance" or "active agent" refers to a chemical entity that is effective in treating a target disorder, disease, or condition.

The term "psychiatric disease" is a disorder of the nervous system.

For a drug, drug unit or active ingredient, the term "effective amount", "therapeutically effective amount" or "prophylactically effective amount" refers to an amount of a drug or an agent that is sufficient to provide the desired effect with acceptable side effects. The determination of the effective amount varies from person to person. It depends on the age and general condition of a subject, as well as the particular active substance used. The appropriate effective amount in a case may be determined by those skilled in the art in the light of routine tests.

As used herein, an "individual" includes a human or non-human animal. An exemplary human individual includes a human individual (referred to as patients) with a disease (e.g., a disease described herein) or a normal individual. As used herein, a "non-human animal" includes all vertebrates, such as non-mammals (e.g., birds, amphibians, and reptiles) and mammals, such as non-human primates, livestock and/or domesticated animals (e.g., sheep, dogs, cats, cows, pigs, etc.).

The following detailed description is intended to illustrate non-limiting embodiments and to enable others skilled in the art to more fully understand the technical scheme of the present invention, its principles, and its practical application, so that others skilled in the art may modify and implement the present invention in various forms to allow it to be optimally adapted to the particular use contemplated.

Compound Represented by Formula I

In one aspect, the present invention provides a compound represented by formula I:

I

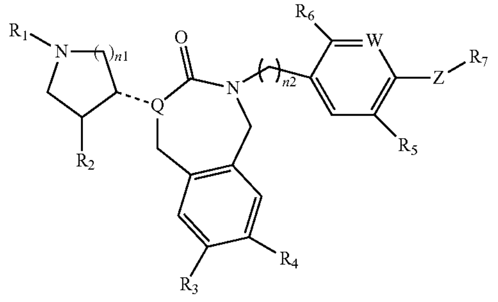

wherein in formula I: n1 and n2 are integers of 1-3;

R1 is selected from C1-C8 linear or branched alkyl, C2-C8 alkenyl, and C2-C8 alkynyl, wherein the alkyl, alkenyl and alkynyl are each independently and optionally substituted with substituents selected from halogen and C1-C8 haloalkyl;

R2 is selected from hydrogen, halogen and C1-C8 haloalkyl;

R3, R4, R5 and R6 are each independently selected from hydrogen, halogen and C1-C8 haloalkyl;

R7 is selected from C1-C8 linear or branched alkyl, cycloalkyl and

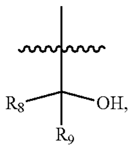

wherein R8 and R9 are each independently selected from C1-C8 linear or branched alkyl, and the alkyl and cycloalkyl are optionally substituted with substituents selected from halogen and C1-C8 haloalkyl;

Z is selected from C, O and N;

Q and W are each selected from C and N; and bond ------ represents that the bond is absent or is present as a single bond;

when the bond ------ represents that the bond is absent, the compound represented by formula I is a compound represented by formula II:

II

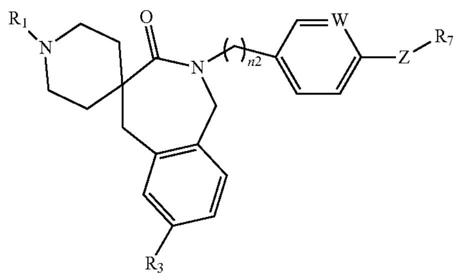

in formula II, n2, R1, R3, R7, W and Z are as defined above; or when the bond ------ represents that the bond is present as a single bond, the compound represented by formula I is a compound represented by formula III:

III

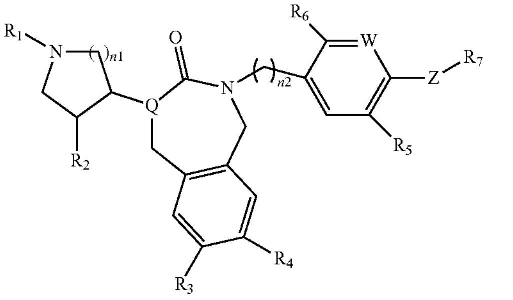

in formula III, n1 and n2 are integers of 1-3;

R1 is selected from C1-C8 linear or branched alkyl, C2-C8 alkenyl, and C2-C8 alkynyl, wherein the alkyl, alkenyl and alkynyl are optionally substituted with substituents selected from halogen and C1-C8 haloalkyl;

R2 is selected from hydrogen, halogen and C1-C8 haloalkyl;

R3, R4, R5 and R6 are each independently selected from hydrogen, halogen and haloalkyl;

R7 is selected from C1-8 linear or branched alkyl, cycloalkyl and

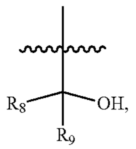

wherein R8 and R9 are each independently selected from C1-C8 linear or branched alkyl, and the alkyl and cycloalkyl are optionally substituted with substituents selected from halogen and C1-C8 haloalkyl;

Z is selected from C, O and N; and

Q and W are each selected from C and N.

In an embodiment, n1 and n2 are integers selected from 1-3. For example, n1 and n2 are each independently selected from 1, 2 and 3, e.g., 1, 2 or 3. In a preferred embodiment, n1 is selected from 2 and 3. In a more preferred embodiment, n1 is 1. In another preferred embodiment, n2 is 1. In a more preferred embodiment, n1 is 2. In another more preferred embodiment, n2 is 2. In a more preferred embodiment, n1 is 3. In another more preferred embodiment, n2 is 3. In a particularly preferred embodiment, n1 is 2 and n2 is 1.

In an embodiment, R1 is selected from C1-C8 linear or branched alkyl, C2-C8 alkenyl, and C2-C8 alkynyl, wherein the alkyl, alkenyl and alkynyl are each independently and optionally substituted with substituents selected from halogen and C1-C8 haloalkyl. In a preferred embodiment, R1 is C1-C8 linear or branched alkyl, wherein the alkyl is optionally substituted with substituents selected from halogen and C1-C8 haloalkyl. In a more preferred embodiment, R1 is C1-C8 linear or linear alkyl. In a particularly preferred embodiment, R1 is C1-C5 linear or branched alkyl. In another particularly preferred embodiment, R1 is C1-C3 linear or branched alkyl. In a specific embodiment, R1 is selected from methyl, ethyl, propyl, isopropyl, butyl, isobutyl, pentyl and isopentyl. In a more specific embodiment, R1 is selected from methyl, ethyl and propyl, e.g., methyl, ethyl or propyl. In a particularly specific embodiment, R1 is methyl. In another particularly specific embodiment, R1 is ethyl. In yet another particularly specific embodiment, R1 is propyl.

In an embodiment, R2 is selected from hydrogen, halogen and C1-C8 haloalkyl. In a preferred embodiment, R2 is selected from hydrogen and halogen. In a more preferred embodiment, R2 is hydrogen. In another more preferred embodiment, R2 is halogen. In a specific embodiment, R2 is selected from hydrogen, fluorine, chlorine, bromine and iodine. In a more specific embodiment, R2 is selected from hydrogen, fluorine, chlorine and bromine. In a more specific embodiment, R2 is fluorine. In another more specific embodiment, R2 is chlorine. In yet another more specific embodiment, R2 is bromine.

In an embodiment, R3, R4, R5 and R6 are each independently selected from hydrogen, halogen and C1-C8 haloalkyl.

In a preferred embodiment, R3 is selected from hydrogen and halogen. In a more preferred embodiment, R3 is hydrogen. In another more preferred embodiment, R3 is halogen. In a particularly preferred embodiment, R3 is selected from fluorine, chlorine, bromine and iodine. In a more preferred embodiment, R3 is selected from fluorine, chlorine and bromine. In a specific embodiment, R3 is selected from hydrogen, fluorine, chlorine and bromine. In a more specific embodiment, R3 is selected from hydrogen, fluorine and chlorine. In a particularly specific embodiment, R3 is fluorine. In another particularly specific embodiment, R3 is chlorine.

In a preferred embodiment, R4 is selected from hydrogen and halogen. In a more preferred embodiment, R4 is hydrogen. In another more preferred embodiment, R4 is halogen. In a particularly preferred embodiment, R4 is selected from fluorine, chlorine, bromine and iodine. In a more preferred embodiment, R4 is selected from fluorine, chlorine and bromine. In a specific embodiment, R4 is selected from hydrogen, fluorine, chlorine and bromine. In a more specific embodiment, R4 is selected from hydrogen, fluorine and chlorine. In a particularly specific embodiment, R4 is fluorine. In another particularly specific embodiment, R4 is chlorine.

In a preferred embodiment, R5 is selected from hydrogen and halogen. In a more preferred embodiment, R5 is hydrogen. In another more preferred embodiment, R5 is halogen. In a particularly preferred embodiment, R5 is selected from fluorine, chlorine, bromine and iodine. In a more preferred embodiment, R5 is selected from fluorine, chlorine and bromine. In a specific embodiment, R5 is selected from hydrogen, fluorine, chlorine and bromine. In a more specific embodiment, R5 is selected from hydrogen, fluorine and chlorine. In a particularly specific embodiment, R5 is fluorine. In another particularly specific embodiment, R5 is chlorine.

In a preferred embodiment, R6 is selected from hydrogen and halogen. In a more preferred embodiment, R6 is hydrogen. In another more preferred embodiment, R6 is halogen. In a particularly preferred embodiment, R6 is selected from fluorine, chlorine, bromine and iodine. In a more preferred embodiment, R6 is selected from fluorine, chlorine and bromine. In a specific embodiment, R6 is selected from hydrogen, fluorine, chlorine and bromine. In a more specific embodiment, R6 is selected from hydrogen, fluorine, and chlorine. In a particularly specific embodiment, R6 is fluorine. In another particularly specific embodiment, R6 is chlorine.

In an embodiment, R7 is selected from C1-C8 linear or branched alkyl, cycloalkyl and

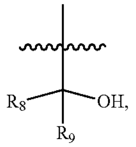

wherein R8 and R9 are each independently selected from C1-C8 linear or branched alkyl, and the alkyl and cycloalkyl are optionally substituted with substituents selected from halogen and C1-C8 haloalkyl.

In a preferred embodiment, R7 is C1-C8 linear or branched alkyl. In a more preferred embodiment, R7 is C1-C5 linear or branched alkyl. In a particularly preferred embodiment, R7 is C1-C3 linear or branched alkyl. In a specific embodiment, R7 is selected from methyl, ethyl, propyl, isopropyl, butyl, isobutyl, pentyl and isopentyl. In a more specific embodiment, R7 is selected from methyl, ethyl, propyl, isopropyl, butyl and isobutyl, e.g., methyl, ethyl, propyl, isopropyl, butyl or isobutyl. In another particularly specific embodiment, R7 is isopropyl.

In a preferred embodiment, R7 is cycloalkyl. In a more preferred embodiment, R7 is C3-C10 cycloalkyl. In a particularly preferred embodiment, R7 is C3-C6 cycloalkyl. In a specific embodiment, R7 is selected from cyclopropyl, cyclobutyl, cyclopentyl and cyclohexyl. In a more specific embodiment, R7 is selected from cyclopropyl, cyclobutyl and cyclopentyl, e.g., cyclopropyl, cyclobutyl or cyclopentyl.

In a preferred embodiment, R7 is

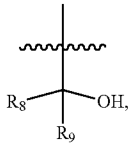

wherein R8 and R9 are each independently selected from C1-C8 linear or branched alkyl. In a preferred embodiment, R7 is

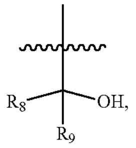

wherein R8 and R9 are each independently selected from C1-C3 linear or branched alkyl. In a specific embodiment, R7 is

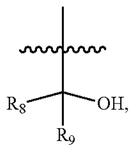

wherein R8 and R9 are each independently selected from methyl, ethyl, propyl, butyl and pentyl. In a more specific embodiment, R7 is

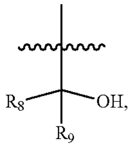

wherein R8 and R9 are each independently selected from methyl, ethyl and propyl, e.g., methyl, ethyl, n-propyl and isopropyl. In a specific embodiment, R8 and R9 are methyl.

In an embodiment, Z is selected from C, O and N. In a preferred embodiment, Z is C. In another preferred embodiment, Z is O. In yet another preferred embodiment, Z is N.

In an embodiment, Q and W are each selected from C and N. In a preferred embodiment, Q is N. In a preferred embodiment, Q is C. In a preferred embodiment, W is C. In a preferred embodiment, W is N.

In an embodiment, the C1-C8 linear or branched alkyl is selected from C1-C5 linear or branched alkyl and C1-C3 linear or branched alkyl. In a specific embodiment, the C1-C8 linear or branched alkyl, the C1-C5 linear or branched alkyl, and the C1-C3 linear or branched alkyl are each independently selected from methyl, ethyl, propyl, butyl, pentyl and isopentyl. In a more specific embodiment, the C1-C8 linear or branched alkyl, the C1-C5 linear or branched alkyl, and the C1-C3 linear or branched alkyl are each independently selected from methyl, ethyl, propyl and butyl.

In an embodiment, the propyl includes, but is not limited to n-propyl (n-Pr, $-CH_2CH_2CH_3$) and isopropyl (i-Pr, $-CH(CH_3)_2$). The butyl includes, but is not limited to n-butyl (n-Bu, $-CH_2CH_2CH_2CH_3$), isobutyl (i-Bu, $-CH_2CH(CH_3)_2$), sec-butyl (s-Bu, $-CH(CH_3)CH_2CH_3$), or tert-butyl (t-Bu, $-C(CH_3)_3$). The pentyl includes, but is not limited to n-pentyl ($-CH_2CH_2CH_2CH_2CH_3$), 2-pentyl ($-CH(CH_3)CH_2CH_2CH_3$), 3-pentyl ($-CH(CH_2CH_3)_2$), 2-methyl-2-butyl ($-C(CH_3)_2CH_2CH_3$), 3-methyl-2-butyl ($-CH(CH_3)CH(CH_3)_2$), 3-methyl-1-butyl ($-CH_2CH_2CH(CH_3)_2$), or 2-methyl-1-butyl ($-CH_2CH(CH_3)CH_2CH_3$).

In an embodiment, the C2-C8 alkenyl is C2-C5 alkenyl. In a specific embodiment, the C2-C8 alkenyl and the C2-C5 alkenyl are each independently selected from vinyl, propenyl, butenyl and pentenyl. In a more preferred embodiment, the C2-C8 alkenyl and the C2-C5 alkenyl are each independently selected from vinyl, propenyl and butenyl.

In an embodiment, the propenyl includes, but is not limited to $-CH_2-CH_2=CH_2$ and $-CH_2=CH_2-CH_3$. The butenyl includes, but is not limited to $-CH_2-CH_2-CH_2=CH_2$, $-CH_2-CH_2=CH_2-CH_3$, $-CH_2=CH_2-CH_2-CH_3$, $-CH=C(CH_3)_2$, $-C(CH_3)=CH_2CH_3$, and $-CH(CH_3)CH=CH_2$. The pentenyl includes, but is not limited to $-CH=CHCH_2CH_2CH_3$, $-CH_2CH=CHCH_2CH_3$, $-CH_2CH_2CH=CHCH_3$, $-CH_2CH_2CH_2CH=CH_2$, $-C(CH_3)=CHCH_2CH_3$, $-CH(CH_3)CH=CHCH_3$, and $-CH(CH_3)CH_2CH=CH_2$. In an embodiment, the C2-C8 alkynyl is C2-C5 alkynyl. In a specific embodiment, the C2-C8 alkynyl and the C2-C5 alkynyl are each independently selected from ethynyl, propynyl, butynyl and pentynyl. In a more specific embodiment, the C2-C8 alkynyl and the C2-C5 alkynyl are each independently selected from ethynyl, propynyl and butynyl.

In an embodiment, the propynyl includes, but is not limited to $-H_2C-C\equiv CH$ and $-C\equiv C-CH_3$. The butynyl includes, but is not limited to $-H_2C-CH_2-C\equiv CH$, $-H_2C-C\equiv C-CH_3$ and $H_3C-CH_2-C\equiv C-$. The pentynyl includes, but is not limited to $H_3C-H_2C-CH_2-$ $C{\equiv}C$—, —$H_2C$—$H_2C$—$C{\equiv}C$—$CH_3$, $H_3C$—$H_2C$—$C{\equiv}C$—$CH_2$— and $(H_3C)_2C$—$C{\equiv}C$—.

In an embodiment, the C1-C8 haloalkyl is C1-C5 haloalkyl. In a specific embodiment, in the C1-C8 haloalkyl and the C1-C5 haloalkyl, the C1-C8 alkyl or the C1-C5 alkyl is substituted with 1, 2, 3 or 4 halogens. In a preferred embodiment, the C1-C8 alkyl or the C1-C5 alkyl is $-(CH_2)_aCX_3$, wherein a is selected from 1, 2, 3, 4, 5, 6 and 7, and X represents halogen. In a specific embodiment, the halogen is selected from fluorine, chlorine, bromine and iodine. In a preferred embodiment, a is selected from 1, 2, 3 and 4. In a preferred embodiment, the halogen is fluorine.

In an embodiment, the C1-C8 haloalkyl or the C1-C5 haloalkyl includes, but is not limited to $-CF_3$, $-CCl_3$, $-CBr_3$, $-CI_3$, —$CH_2CF_3$, —$CH_2CCl_3$, —$CH_2CBr_3$, —$CH_2CI_3$, $-(CH_2)_2CF_3$, $-(CH_2)_2CCl_3$, $-(CH_2)_2CBr_3$, —$(CH_2)_2CI_3$, etc.

In an embodiment, the halogen is selected from fluorine, chlorine, bromine and iodine. In a preferred embodiment, the halogen is selected from fluorine, chlorine and bromine, e.g., fluorine, chlorine, bromine or iodine. In a specific embodiment, the halogen is fluorine.

In a specific embodiment, Z is O, and R1, R2, R3, R4, R5, R6, R7, n1, n2, Q and the bond ------ are as defined above. In a more specific embodiment, Z is O; R1 is C1-C5 linear or branched alkyl; R2 is selected from hydrogen and halogen; R3, R4, R5 and R6 are each independently selected from hydrogen and halogen; and R7 is selected from C1-C5 linear or branched alkyl and C3-C6 cycloalkyl. In a preferred embodiment, Z is O; R1 is selected from methyl, ethyl, propyl, isopropyl, butyl and isobutyl; R2 is selected from hydrogen, fluorine, chlorine, bromine and iodine; R3, R4, R5 and R6 are each independently selected from hydrogen, fluorine, chlorine, bromine and iodine; and R7 is selected from methyl, ethyl, propyl, isopropyl, butyl, isobutyl, cyclopropyl, cyclobutyl and cyclopentyl.

In a specific embodiment, when Z is O, and the bond ------ is a single bond, the compound represented by formula I is a compound represented by formula I-1:

I-1

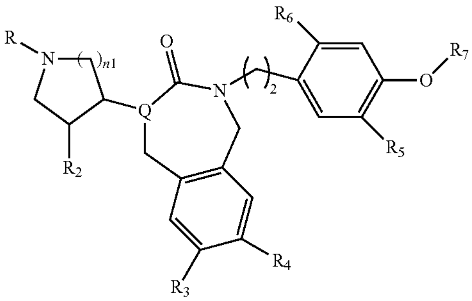

wherein R1, R2, R3, R4, R5, R6, R7, n1, n2 and Q are as defined above. In a preferred embodiment, when Z is O, and the bond ------ is a single bond, the compound represented by formula I is a compound represented by formula I-1, wherein R1 is C1-C5 linear or branched alkyl; R2 is selected from hydrogen and halogen; R3, R4, R5 and R6 are each independently selected from hydrogen and halogen; R7 is selected from C1-C5 linear or branched alkyl and C3-C6 cycloalkyl; and Q is N. In a preferred embodiment, when Z is O, and the bond ------ is a single bond, and the compound represented by formula I is a compound represented by formula I-1, wherein R1 is selected from methyl, ethyl, propyl, isopropyl, butyl and isobutyl; R2 is selected from hydrogen, fluorine, chlorine, bromine and iodine; R3, R4, R5 and R6 are each independently selected from hydrogen, fluorine, chlorine, bromine and iodine; and R7 is selected from methyl, ethyl, propyl, isopropyl, butyl, isobutyl, cyclopropyl, cyclobutyl and cyclopentyl.

In an embodiment, the compound represented by formula I is a compound represented by formula IV:

IV

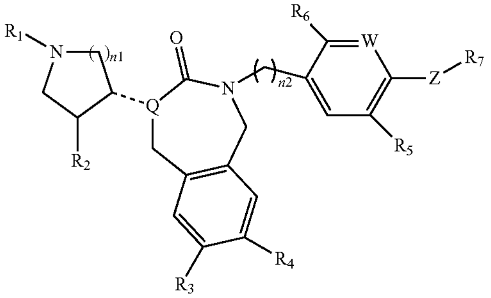

wherein: n1 and n2 are integers of 1-3; R1 is selected from methyl, ethyl, propyl and butyl; R2 is selected from hydrogen, fluorine, chlorine, bromine and iodine; R3, R4, R5 and R6 are each selected from hydrogen, fluorine and chlorine; R7 is selected from isopropyl, isobutyl, ethyl, propyl, methyl, cyclopropyl, cyclobutyl and

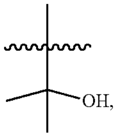 [SMILES: *C(C)(C)O]

Z is selected from C, O and N; Q and W are each selected from C and N; and bond ------ represents that the bond is absent or is present as a single bond. In a specific embodiment, when the bond ------ in the compound represented by formula I is absent, the compound represented by formula I is a compound represented by formula V:

V

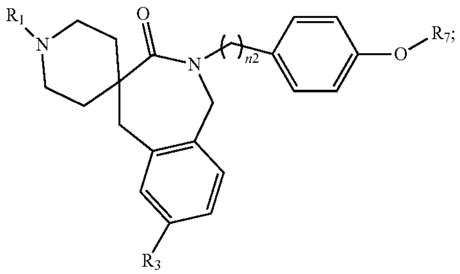

wherein n2 is an integer of 1-2; R1 is selected from methyl, ethyl, propyl, and butyl; R3 is selected from hydrogen, fluorine and chlorine; and R7 is selected from isopropyl, isobutyl, ethyl, propyl, methyl, cyclopropyl, cyclobutyl, cyclohexyl and

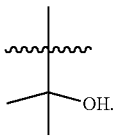 [SMILES: *C(C)(C)O]

In an embodiment, when the bond ------ in the compound represented by formula I is a single bond, the compound represented by formula I is a compound represented by formula VI:

VI

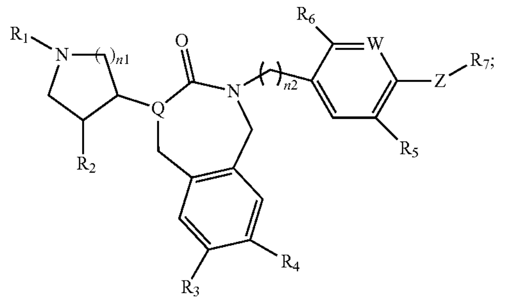

wherein n1 and n2 are integers of 1-3; R1 is methyl; R2 is selected from fluorine and hydrogen; R3, R4, R5 and R6 are each selected from hydrogen, fluorine and chlorine; R7 is selected from isopropyl, cyclopropyl, isobutyl, methyl and

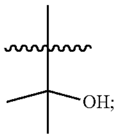 [SMILES: *C(C)(C)O]

Z is selected from C, O and N; and Q and W are each selected from C and N.

In an embodiment, the compound represented by formula I is selected from any one of the compounds shown below:

A19020

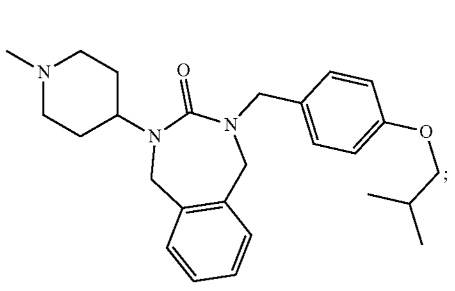

-continued

A19001

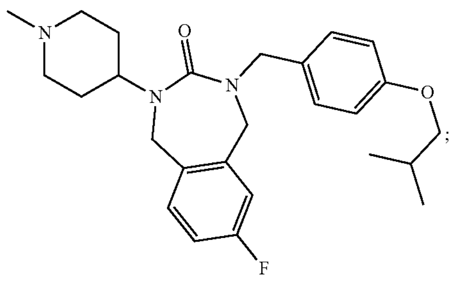

A190017

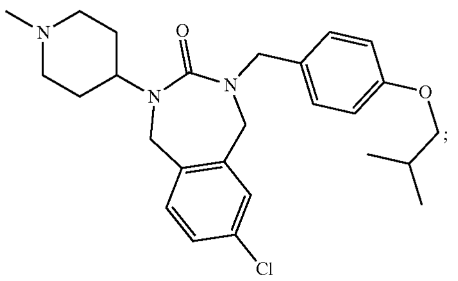

A19005

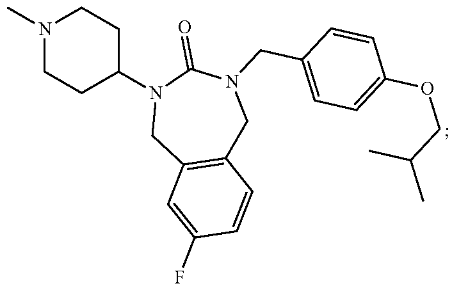

A19007

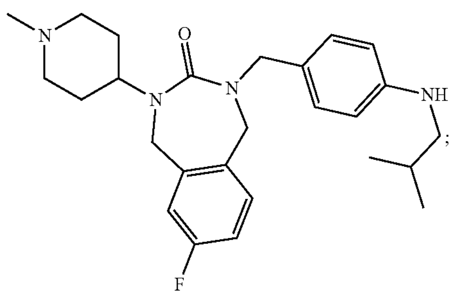

A19006

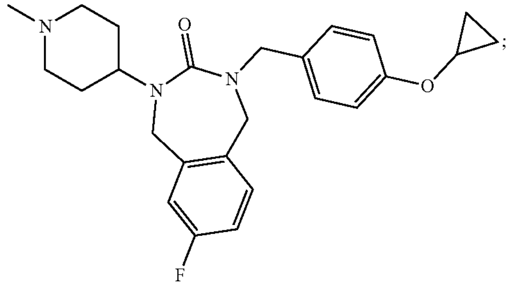

-continued
A19008
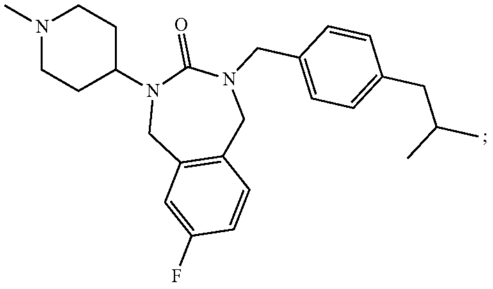
A19009
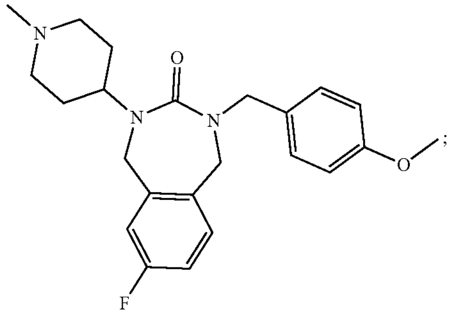
A19011
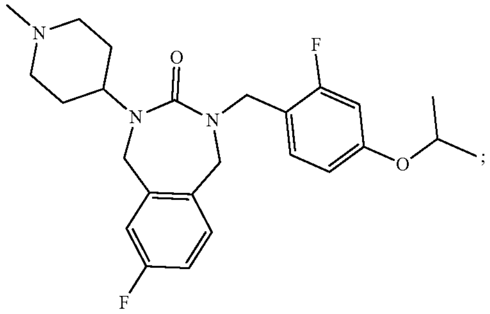
A19012
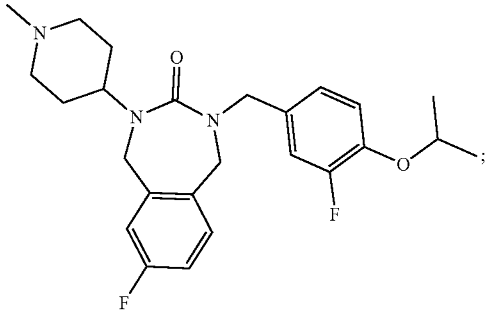
-continued
A19013
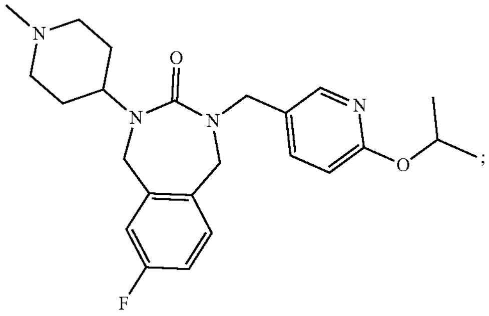
A19015
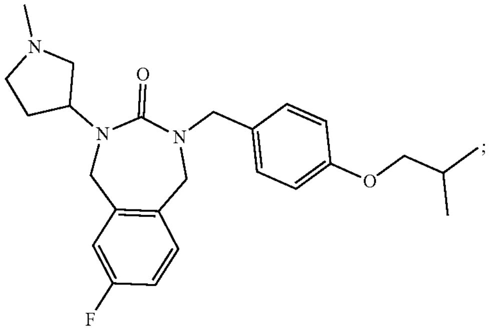
A19019
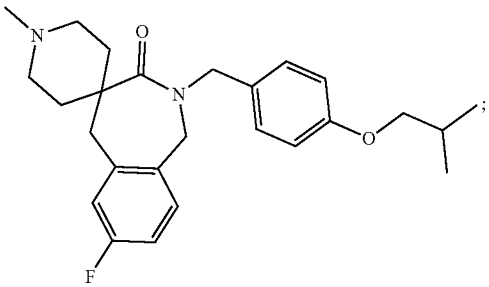
A19014-0
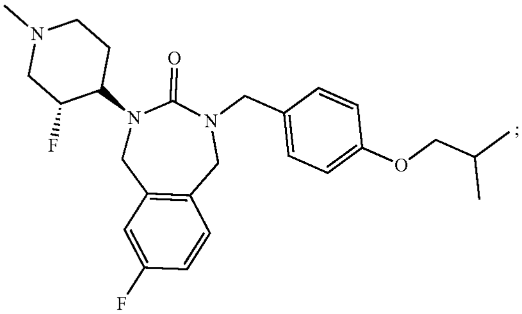

-continued

A19014-0A

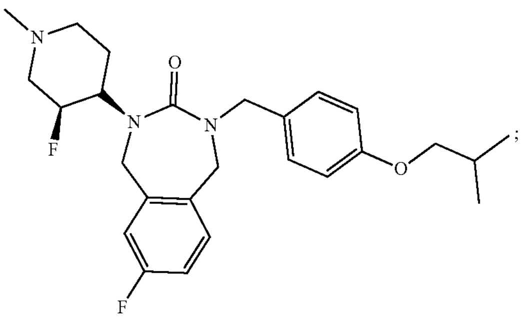

;

A20001

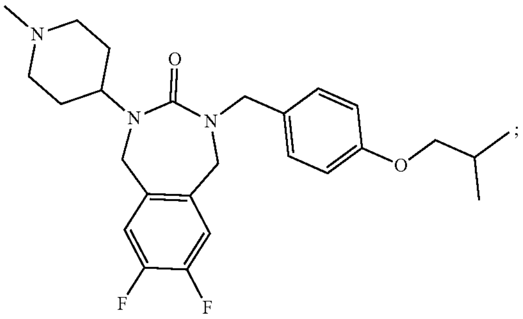

;

A19016

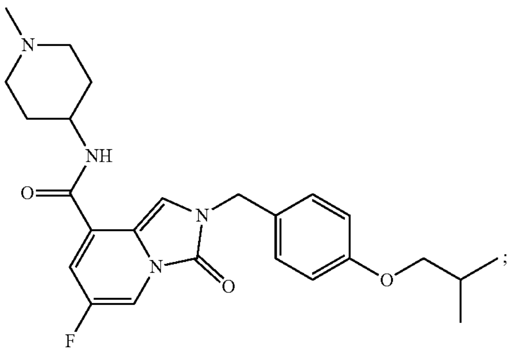

;

A19010

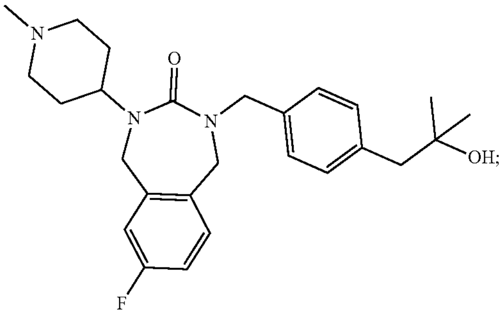

-continued

A19022

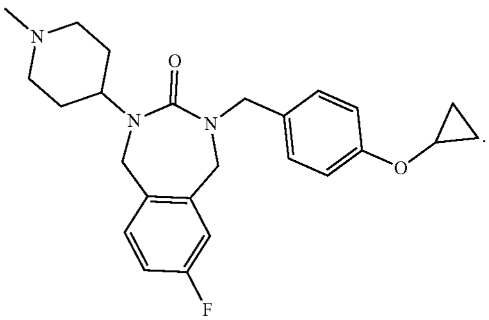

.

Method for Preparing Compound Represented by Formula I

The present invention provides a method for preparing the compound represented by formula I, which comprises:

condensing a substituted o-carboxybenzylamine with a primary amine to obtain an intermediate I-a, wherein the amino group of the o-carboxybenzylamine is protected with Boc; subsequently adding hydrochloric acid to the intermediate I-a to perform deprotection of Boc to obtain an intermediate I-b; reductively aminating the I-b with a substituted aryl aldehyde to obtain an intermediate I-c; subsequently subjecting the I-c to a reaction with borane to reduce the amide moiety to obtain an intermediate I-d; cyclizing the I-d with triphosgene to obtain an intermediate I-e; and finally, alkylating the I-e to obtain the compound represented by formula I.

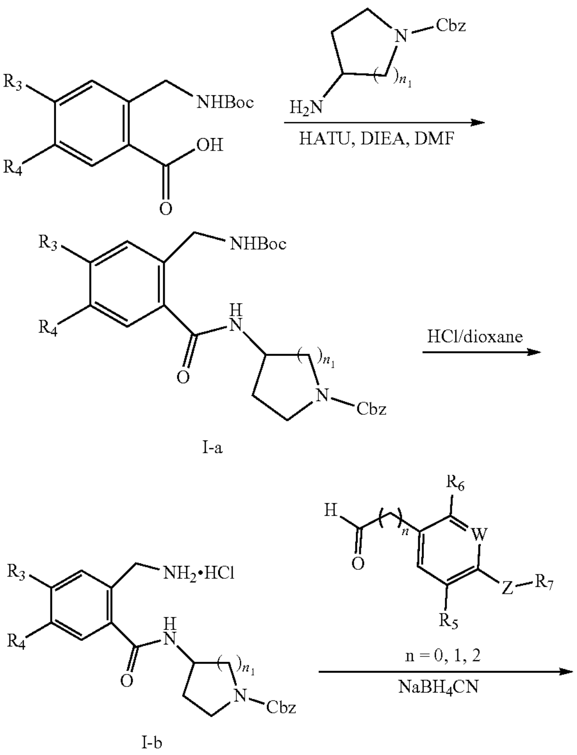

-continued

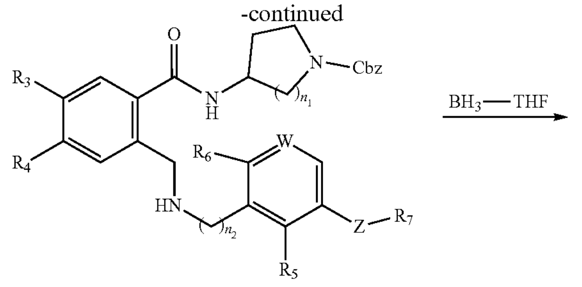

I-c

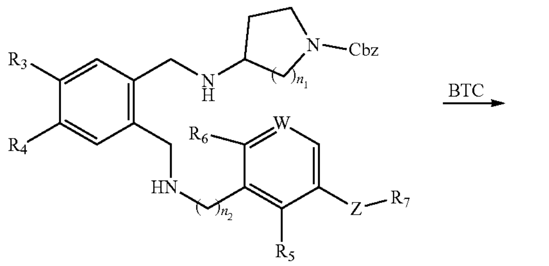

I-d

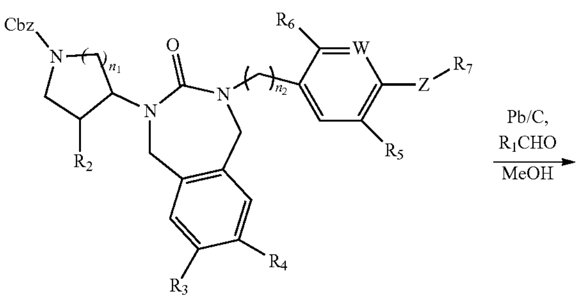

I-e

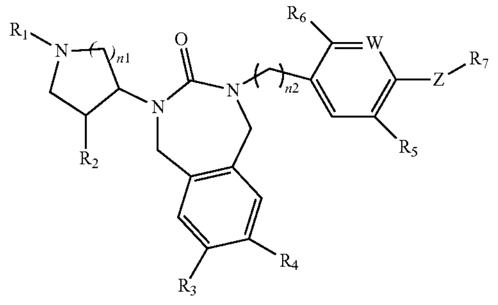

I

Pharmaceutical Composition and Pharmaceutical Formulation

Another object of the present invention is to provide a pharmaceutical composition comprising a therapeutically effective amount of the compound of the present invention, and optionally comprising a pharmaceutically acceptable excipient, carrier, adjuvant or vehicle or a combination thereof.

Pharmaceutically acceptable carriers that may be used in the pharmaceutical composition of the present invention include, but are not limited to, sterile liquids, such as water and oil, and the composition may also comprise small amounts of wetting agents, emulsifiers, lubricants, stabilizers or pH buffering agents as required. Oral formulations may comprise a standard carrier.

In an embodiment of the present invention, the pharmaceutical composition may be formulated in a conventional manner using one or more pharmaceutically acceptable carriers. Therefore, the active compound of the present invention may be formulated into dosage forms for oral, buccal, intranasal, parenteral (e.g., intravenous, intramuscular or subcutaneous) or rectal administration or for administration by inhalation or insufflation.

The pharmaceutical composition of the present invention may be administered in any manner as long as it achieves the effect of preventing, alleviating, avoiding or curing the symptoms of a human or animal patient. For example, the composition may be formulated into various suitable dosage forms according to the administration route, in particular injections, such as a lyophilized powder for injection, a solution for injection or a sterile powder for injection.

In an embodiment of the present invention, an effective dose of a compound of the present invention may be administered orally, e.g., with an inert diluent or with a certain carrier. According to some embodiments of the present invention, the compound of the present invention may be encapsulated in gelatin capsules or compressed into tablets. For the purpose of oral treatment, the compound of the present invention may be used with excipients and in the form of a tablet, a troche, a capsule, a suspension, a syrup and the like. According to an example of the present invention, the above formulations should contain at least 0.5% (w/w) of the active compound of the present invention, but may vary depending on the particular dosage form, wherein 4% to about 70% of the unit weight is convenient. The amount of the active compound in such pharmaceutical compositions should allow an appropriate dosage to be obtained.

In an embodiment of the present invention, for oral administration, the active compound of the present invention may be formulated, for example, by conventional means, into tablets or capsules with pharmaceutically acceptable excipients such as a binding agent, a fillers, a lubricant, a disintegrant or a wetting agent. Tablets may be coated by methods well known in the art. Liquid formulations used for oral administration may, for example, be presented as solutions, syrups or suspensions, or be evaporated to a dry product, which is constituted with water or other suitable carriers before use. Such liquid formulations may be prepared by conventional means using pharmaceutically acceptable additives such as a suspending agent, an emulsifier, a non-aqueous carrier and a preservative.

In an embodiment of the present invention, when the active compound of the present invention is used for parenteral administration, the compound provided in the present invention may be combined with sterile water or an organic medium to form an injectable solution or suspension.

In an embodiment of the present invention, the active compound of the present invention may be formulated into rectal compositions such as suppositories or retention enemas, e.g., containing conventional suppository bases such as cocoa butter or other glycerides.

Therapeutic Use and Method

The present invention also provides use of the compound represented by formula I in preparing a medicament for treating a psychiatric disease.

The present invention also provides a method for treating a psychiatric disease, which comprises administering to a subject in need the compound represented by formula I or the pharmaceutical composition thereof. The method also optionally comprises administering another active agent for treating a psychiatric disease.

The present invention also provides a compound represented by formula I or a pharmaceutical composition thereof for use in treating a psychiatric disease.

In an embodiment, the psychiatric disease is selected from schizophrenia and psychosis.

In another embodiment, the psychiatric disease is selected from Parkinson's disease, behavioral and psychological symptom of dementia.

EXEMPLARY EMBODIMENTS

1. A compound represented by formula I:

I

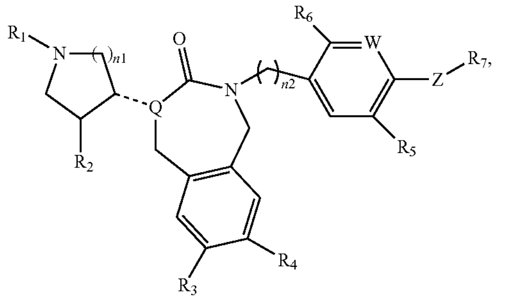

wherein in formula I: n1 and n2 are integers of 1-3;

R1 is C1-C5 linear or branched alkyl;

R2 is selected from hydrogen and halogen;

R3, R4, R5 and R6 are each independently selected from hydrogen and halogen;

R7 is selected from C1-C5 linear or branched alkyl, cycloalkyl and

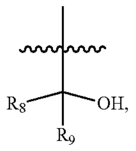

wherein R8 and

R9 are each independently selected from C1-C3 linear or branched alkyl;

Z is selected from C, O and N;

Q and W are each selected from C and N; and bond ------ represents that the bond is absent or is present as a single bond;

when the bond ------ represents that the bond is absent, the compound represented by formula I is a compound represented by formula II:

II

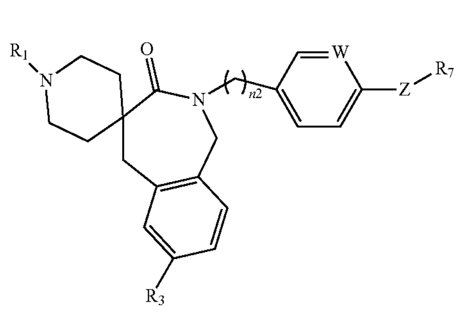

in formula II, n2, R1, R3, R7, W and Z are as defined above;

when the bond ------ represents that the bond is present as a single bond, the compound represented by formula I is a compound represented by formula III:

III

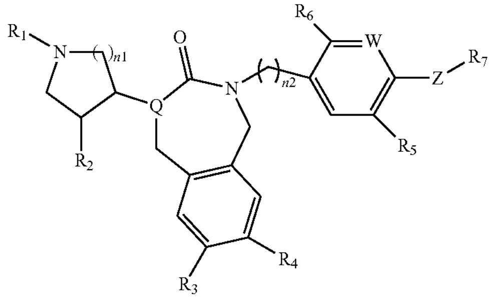

in formula III, n1 and n2 are integers of 1-3;

R1 is C1-C5 linear or branched alkyl;

R2 is selected from hydrogen and halogen;

R3, R4, R5 and R6 are each independently selected from hydrogen and halogen;

R7 is selected from C1-5 linear or branched alkyl, cycloalkyl and

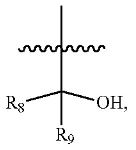

wherein R8 and R9 are each independently selected from C1-C3 linear or branched alkyl;

Z is selected from C, O and N; and

Q and W are each selected from C and N.

2. The compound represented by formula I according to item 1, characterized in that, the halogen is fluorine, chlorine, bromine and iodine.

3. The compound represented by formula I according to item 1, characterized in that, the C1-C5 linear or branched alkyl is selected from methyl, ethyl, propyl, isopropyl, butyl, isobutyl, pentyl and isopentyl; the cycloalkyl is selected from cyclopropyl, cyclobutyl and cyclopentyl; and the C1-C3 linear or branched alkyl is methyl, ethyl, propyl or isopropyl.

4. The compound represented by formula I according to item 1, characterized in that, the compound represented by formula I is a compound represented by formula IV:

IV

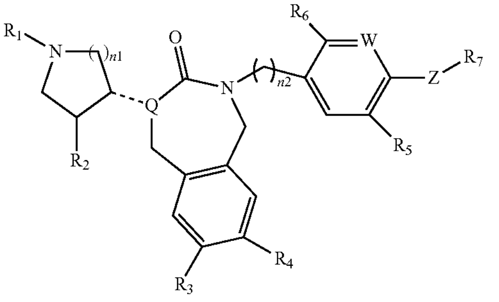

wherein: n1 and n2 are integers of 1-3;

R1 is selected from methyl, ethyl, propyl and butyl;

R2 is selected from hydrogen, fluorine, chlorine, bromine and iodine;

R3, R4, R5 and R6 are each selected from hydrogen, fluorine and chlorine;

R7 is selected from isopropyl, isobutyl, ethyl, propyl, methyl, cyclopropyl, cyclobutyl and

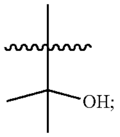 [SMILES: *C(C)(C)O]

Z is selected from C, O and N;

Q and W are each selected from C and N; and bond ------ represents that the bond is absent or is present as a single bond.

5. The compound represented by formula I according to item 1, characterized in that, when the bond ------ is absent, the compound represented by formula I is a compound represented by formula V:

V

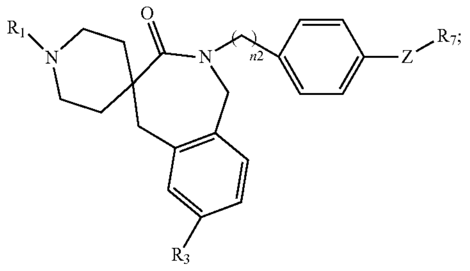

wherein n2 is an integer of 1-2;

R1 is selected from methyl, ethyl, propyl and butyl;

R3 is selected from hydrogen, fluorine and chlorine; and

R7 is selected from isopropyl, isobutyl, ethyl, propyl, methyl, cyclopropyl, cyclobutyl and

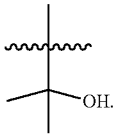 [SMILES: *C(C)(C)O]

6. The compound represented by formula I according to item 1, characterized in that, when the bond ------ is present as a single bond, the compound represented by formula I is a compound represented by formula VI:

VI

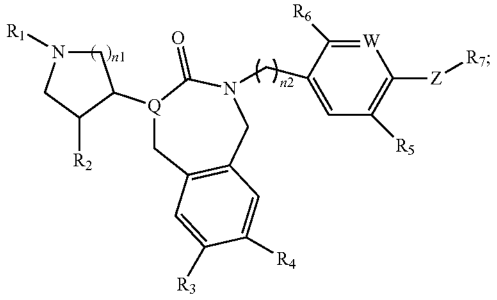

wherein n1 and n2 are integers of 1-3;

R1 is methyl;

R2 is selected from fluorine and hydrogen;

R3, R4, R5 and R6 are each selected from hydrogen, fluorine and chlorine;

R7 is selected from isopropyl, cyclopropyl, isobutyl, methyl and

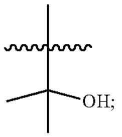 [SMILES: *C(C)(C)O]

Z is selected from C, 0 and N; and

Q and W are each selected from C and N.

7. The compound represented by formula I according to any one of items 1-4, characterized in that, the compound is selected from any one of the following compounds:

A19020

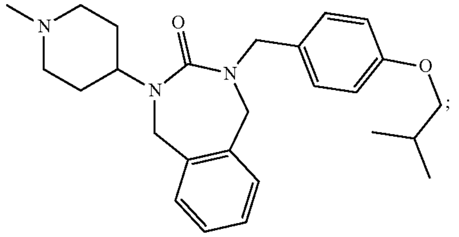

A19001

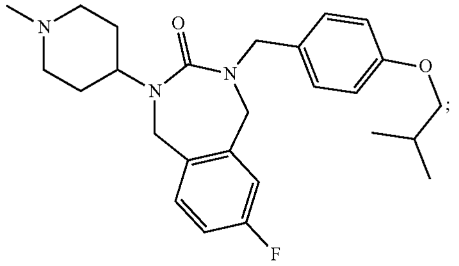

-continued
A190017
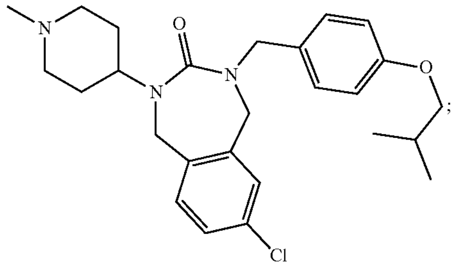
A19005
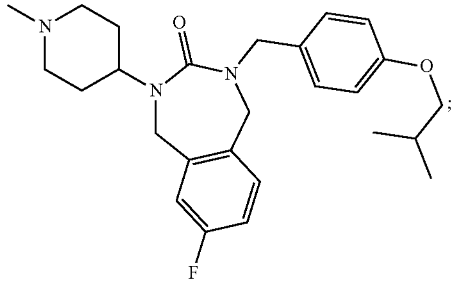
A19007
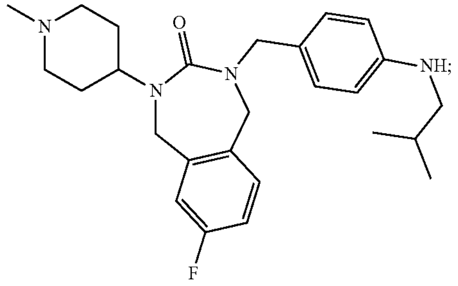
A19006
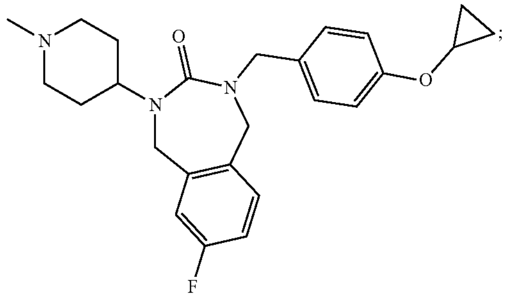
A19008
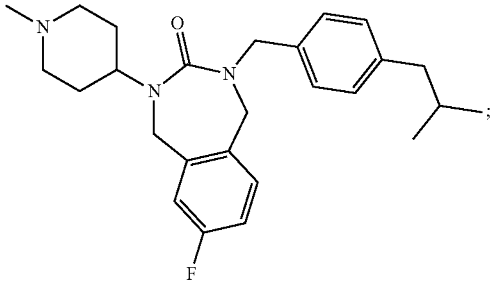
-continued
A19009
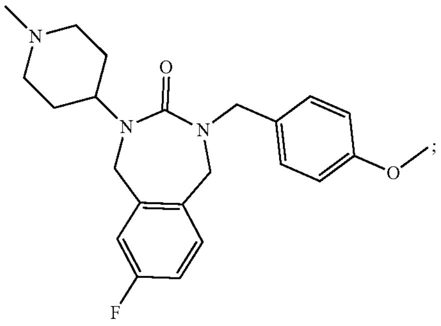
A19011
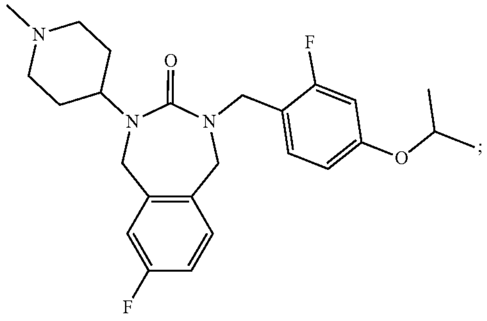
A19012
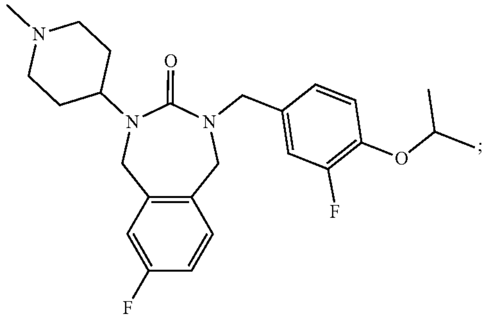
A19013
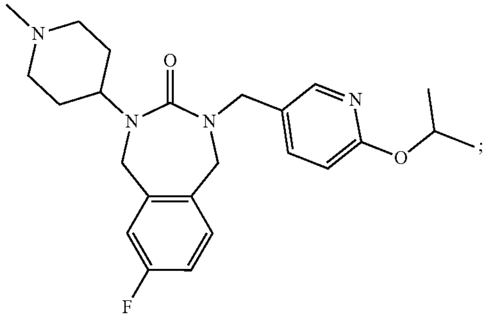

-continued

A19015

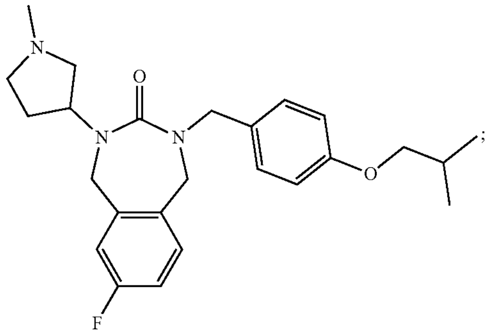

A19019

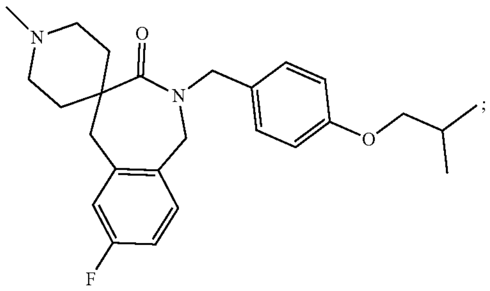

A19014-0

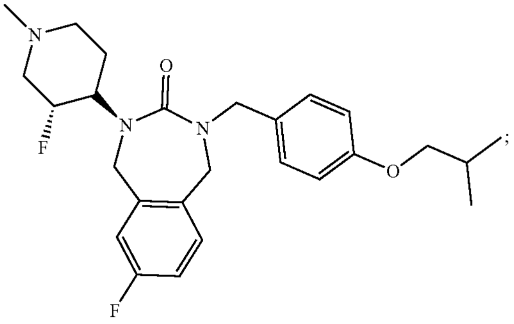

A19014-0A

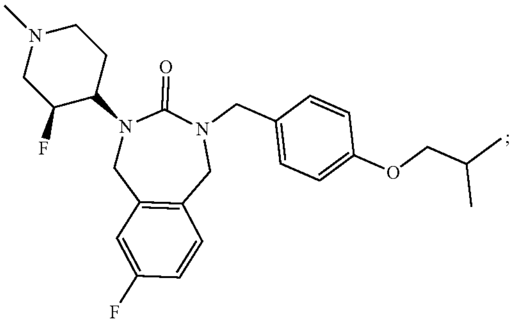

-continued

A20001

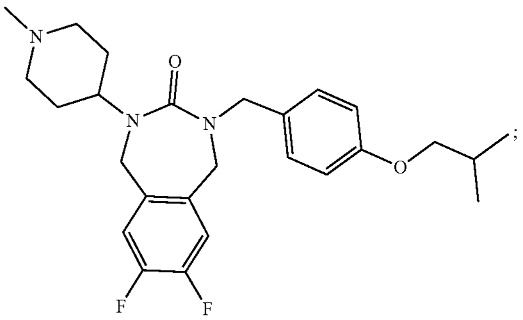

A19016

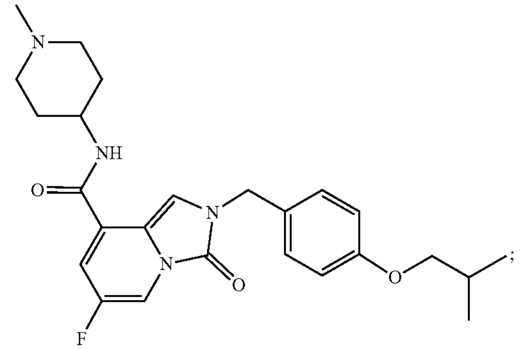

A19010

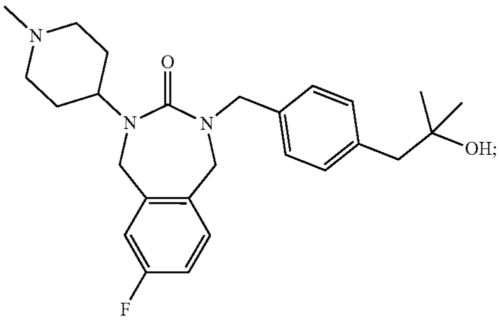

A19022

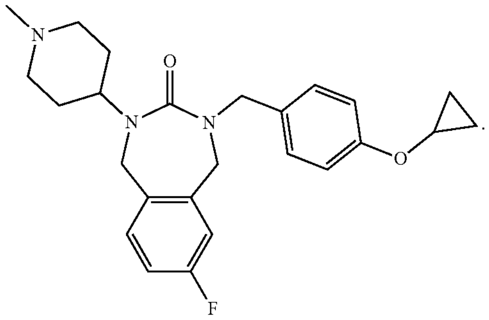

8. A pharmaceutical composition comprising the compound according to any one of items 1-7, and optionally further comprising a pharmaceutically acceptable excipient, carrier, adjuvant or vehicle or a combination thereof.

9. Use of the compound according to any one of items 1-7 or the pharmaceutical composition according to item 8 in preparing a medicament for treating a psychiatric disease.

10. The use according to item 9, characterized in that, the psychiatric disease is schizophrenia and psychosis.

11. The use according to claim 9, characterized in that, the psychiatric disease is Parkinson's disease, behavioral and psychological symptom of dementia.

Beneficial Effects

The compound provided in the present invention acts on 5-$HT_{2A}$ and 5-$HT_{2C}$ receptors, and has selectivity on 5-$HT_{2A}$ better than or similar to pimavanserin. The compound provided in the present invention is used for treating schizophrenia or Parkinson's disease, behavioral and psychological symptom of dementia. The compound of the present invention has antipsychotic activity comparable to pimavanserin, less side effects of sedation and motor deterioration than pimavanserin, and less cardiotoxicity than pimavanserin.

EXAMPLE

The present invention will be further described by the following examples, which, however, are not intended to limit the scope of the present invention. It will be understood by those skilled in the art that various changes and modifications may be made to the present invention without departing from the spirit and scope of the present invention.

SYNTHETIC EXAMPLES

Example 1: Preparation of 2-(1-methylpiperidin-4-yl)-4-[[4-(2-methylpropoxy)phenyl]methyl]-1,5-dihydro-2,4-benzodiazepine -3-one (A19020)

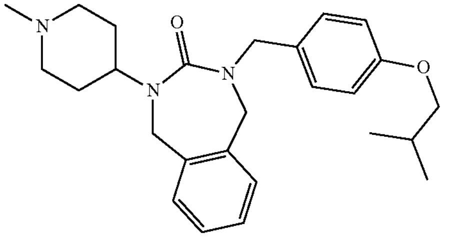 [SMILES: CC(C)COc1ccc(CN2Cc3ccccc3CN(C3CCN(C)CC3)C2=O)cc1]

Synthetic Route:

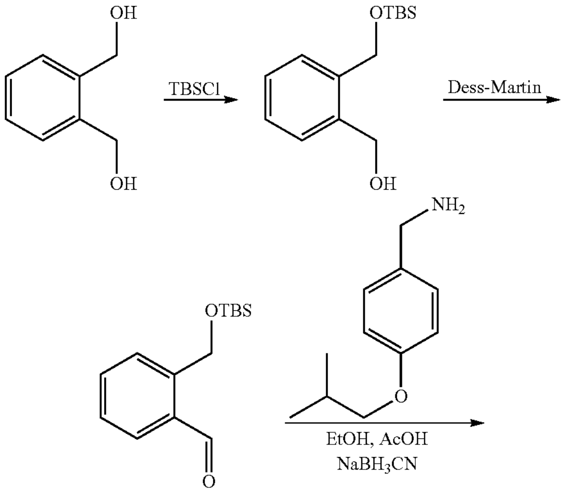

-continued

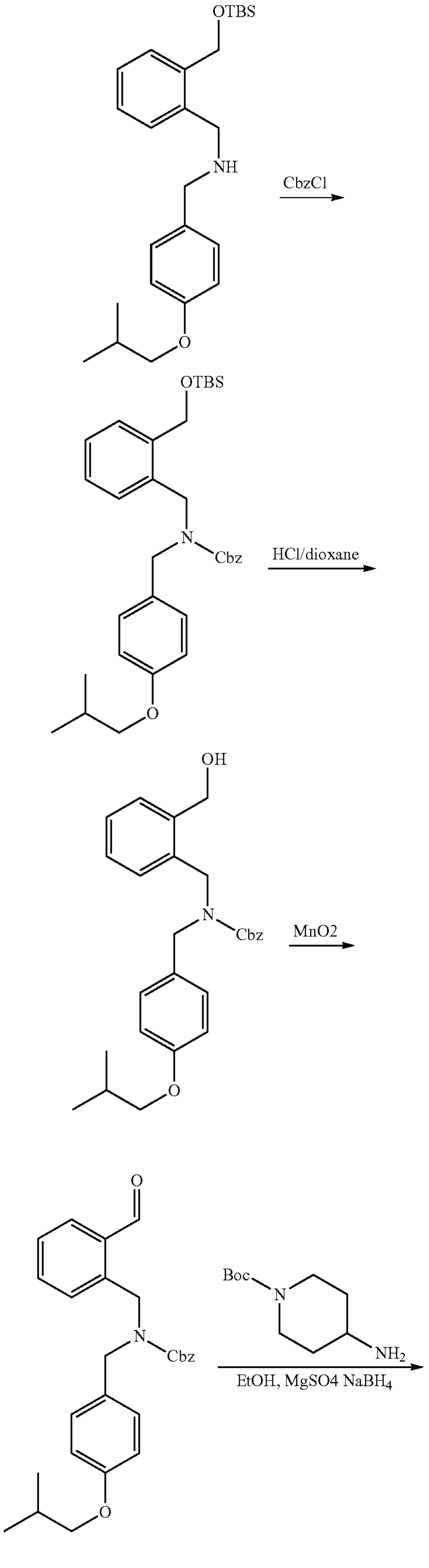

-continued

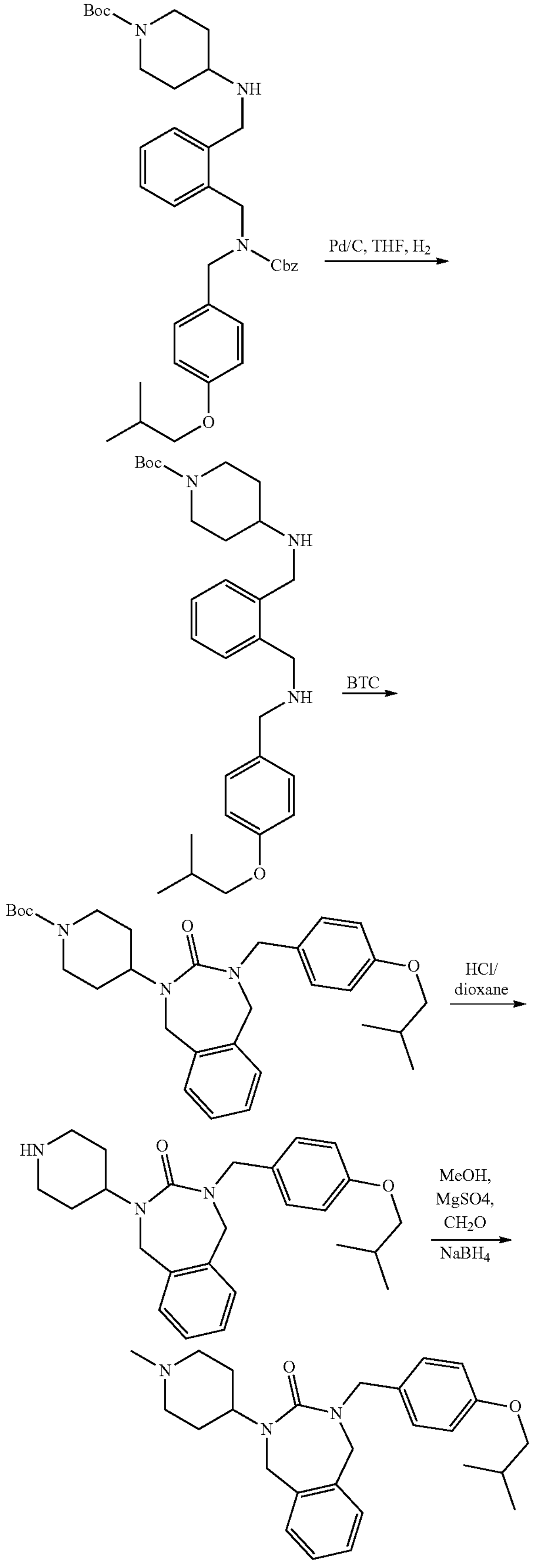

1.1 Preparation of 2-[[(tert-butyldimethylsilyl)oxy]methyl]benzyl alcohol 1,2-phenylenedimethanol (22.0 g, 159.2 mmol), tert-butyldimethylsilyl chloride (24.0 g, 159.2 mmol), triethylamine (16.1 g, 159.2 mmol) and DCM (200.00 mL) were added into a 500 mL three-necked round-bottom flask, and the mixture was stirred at room temperature overnight under nitrogen atmosphere. The reaction mixture was quenched with water, extracted with DCM (3×100 mL) and washed with saturated brine (200 mL). The DCM phase was dried over anhydrous sodium sulfate, filtered under suction and concentrated to give a colorless oil (30 g, yield 74.64%).

1.2 Preparation of 2-[(tert-butyldimethylsilyl)oxymethyl]benzaldehyde

2-[(tert-butyldimethylsilyl)oxymethyl]benzyl alcohol (30.00 g, 118.8 mmol), Dess Martin (50.4 g, 118.8 mmol) and DCM (300 mL) were added into a 1 L three-necked round-bottom flask, and the mixture was reacted at room temperature for 4 h under nitrogen atmosphere. The reaction mixture was quenched with water, extracted with DCM (3×100 mL) and washed with saturated brine (200 mL). The DCM phase was dried over anhydrous sodium sulfate, filtered under suction and concentrated, and the residue was purified by column chromatography (ethyl acetate/petroleum ether=1/35) to give a colorless oil (17 g, yield 58.62%).

1.3 Preparation of 2-[(tert-butyldimethylsilyl)oxymethyl]benzyl-[4-(2-methylpropoxy) phenyl]methylamine 2-[(tert-butyldimethylsilyl)oxymethyl]benzaldehyde (1.00 g, 3.9 mmol), 1-(4-isobutoxyphenyl)methylamine (0.66 g, 3.9 mmol), $MgSO_4$ (0.1 g, 0.83 mmol) and EtOH (10 mL) were added into a 50 mL three-necked round-bottom flask, and the mixture was reacted at room temperature for 3 h with nitrogen purging and maintaining, then NaBH4 (0.76 g, 19.9 mmol) was added, and the resulting mixture was stirred at room temperature for 1 h. The reaction mixture was added with water (30 mL), extracted with DCM (3×20 mL) and washed with saturated brine (30 mL). The DCM phase was dried over anhydrous sodium sulfate, filtered under suction and concentrated to give a colorless oil (1.6 g, yield 96.85%).

1.4 Preparation of benzyl-[N-2-[((tert-butyldimethylsilyl)oxy)methyl]benzyl]-N-[4-(2-methylpropoxy) benzyl]carbamate 2-[(tert-butyldimethylsilyl)oxymethyl]benzyl-[4-(2-methylpropoxy)phenyl]methylamine (1.6 g, 0.004 mol), tetrahydrofuran (5 mL) and water (5 mL), benzyl chloroformate (0.79 g, 0.005 mol) and potassium carbonate (1.08 g, 0.008 mol) were added into a 50 mL round-bottom flask, and the mixture was stirred at 50° C. for 2 h. The reaction mixture was added with water (30 mL), extracted with ethyl acetate (3×20 mL), and washed with saturated brine (50 mL). The ethyl acetate phase was dried over anhydrous sodium sulfate, filtered under suction and concentrated to give an oil (2.27 g).

1.5 Preparation of benzyl-[N-2-(hydroxymethyl) benzyl]-N-[4-(2-methylpropoxy) benzyl]carbamate Benzyl-[N-2-[((tert-butyldimethylsilyl)oxy)methyl]benzyl]-N-[4-(2-methylpropoxy)benzyl]carbamate (2.27 g, 4.14 mmol), dioxane (20.00 mL) and HCl (5.2 mL) were placed in a 50 mL three-necked round-bottom flask with inert nitrogen purging and maintaining, and the mixture was stirred at room temperature for 1 h. The reaction mixture was concentrated, and the residue was purified by silica gel column chromatography (ethyl acetate/petroleum ether=1/5) to give a colorless oil (0.87 g, yield 48.6%).

1.6 Preparation of benzyl-[N-2-(formylbenzyl)]-N-[4-(2-methylpropoxy) benzyl]carbamate Benzyl-[N-2-(hydroxymethyl)benzyl]-N-[4-(2-methylpropoxy)benzyl]carbamate (0.87 g, 2.0 mmol), manganese dioxide (2.62 g, 30.1 mmol) and DCM (20 mL) were placed in a 50 mL round-bottom flask, and the mixture was warmed up to 80° C. and stirred overnight. The reaction mixture was filtered to remove the solid, and the filtrate was directly concentrated to give an oil (0.75 g, yield 86.61%).

1.7 Preparation of benzyl-[N-2-(((1-tert-butoxycarbonylpiperidine-4-yl)amino)methyl) benzyl]-N-[4-(2-methylpropoxy)benzyl]carbamate Benzyl-[N-2-(formylbenzyl)]-N-[4-(2-methylpropoxy) benzyl]carbamate (0.75 g, 1.74 mmol), 4-amino-tert-butoxycarbonylpiperidine (0.42 g, 2.08 mmol), magnesium sulfate (0.10 g, 0.001 mmol) and ethanol (10 mL) were added into a 50 mL three-necked round-bottom flask, with nitrogen purging and maintaining, and the mixture was stirred at room temperature for 3 h, subsequently added with $NaBH_4$ (0.33 g, 8.69 mmol) and stirred at room temperature for 1 h. The reaction mixture was added with water (30 mL), extracted with ethyl acetate (3×20 mL) and washed with saturated brine (50 mL). The ethyl acetate phase was dried over anhydrous sodium sulfate, filtered under suction and concentrated to give an oil (1.1 g).

1.8 Preparation of N-[2-(((1-tert-butoxycarbonylpiperidine-4-yl)amino)methyl)benzyl]-N-[4-(2-methylpropoxy)benzyl]amino Benzyl-[N-2-(((1-tert-butoxycarbonylpiperidine-4-yl) amino)methyl)benzyl]-N-[4-(2-methylpropoxy)benzyl]carbamate (1.1 g), palladium on carbon (0.1 g), methanol (5 mL) and tetrahydrofuran (5 mL) were placed in a 50 mL three-necked round-bottom flask, with hydrogen purging, and the mixture was stirred at room temperature for 3 h. The reaction mixture was filtered to remove the solid, and the filtrate was directly concentrated to give an oil (0.65 g).

1.9 Preparation of 2-(1-tert-butoxycarbonylpiperidine-4-yl)-4-[[4-(2-methylpropoxy)phenyl]methyl]-1,5-dihydro-2,4-b enzodiazepine-3-one N-[2-(((1-tert-butoxycarbonylpiperidine-4-yl)amino) methyl)benzyl]-N-[4-(2-methylpropoxy)benzyl]amino (0.65 g, 1.34 mmol) and tetrahydrofuran (10 mL) were added into a 50 mL round-bottom flask, with inert nitrogen purging and maintaining, followed by the addition of BTC (0.16 g, 0.54 mmol) at −40° C., and the mixture was reacted for 1 h with the temperature maintained. The reaction mixture was added with water (30 mL), extracted with ethyl acetate (3×20 mL) and washed with saturated brine (50 mL). The ethyl acetate phase was dried over anhydrous sodium sulfate, filtered under suction and concentrated to give an oil (0.78 g).

1.10 Preparation of 2-(piperidin-4-yl)-4-[[4-(2-methylpropoxy)phenyl]methyl]-1,5-dihydro-2,4-benzodiazepine-3-one 2-(1-tert-butoxycarbonylpiperidine-4-yl)-4-[[4-(2-methylpropoxy)phenyl]methyl]-1,5-dihydro-2,4-b enzodiazepine-3-one (0.78 g, 1.53 mmol), DCM (10 mL) and HCl/dioxane (4 M, 0.22 g, 1.6 mmol) were added into a 50 mL round-bottom flask, and the mixture was stirred at room temperature for 1 h. The reaction mixture was directly concentrated to give an oil (0.66 g).

1.11 Preparation of 2-(1-methylpiperidin-4-yl)-4-[[4-(2-methylpropoxy)phenyl]methyl]-1,5-dihydro-2,4-benzodiazepine -3-one 2-(piperidin-4-yl)-4-[[4-(2-methylpropoxy)phenyl] methyl]-1,5-dihydro-2,4-benzodiazepine-3-one (0.66 g, 1.6 mmol), formaldehyde (0.1 g, 3.2 mmol), triethylamine (0.66 g, 6.4 mmol), magnesium sulfate (0.02 g, 0.16 mmol) and methanol (10 mL) were added into a 50 mL round-bottom flask, and the mixture was stirred at room temperature for 3 h, subsequently added with $NaBH_4$ (0.31 g, 8.1 mmol), and stirred at room temperature for 1 h. The reaction mixture was added with water (30 mL), extracted with ethyl acetate (3×20 mL), and washed with saturated brine (30 mL). The ethyl acetate phase was dried over anhydrous sodium sulfate, filtered under suction and concentrated, and the residue was finally purified on an Intel Flash-1 column to give a pale-yellow oil (11.6 mg, yield 1.7%). $^1H$ NMR (400 MHz, Methanol-$d_4$) δ 7.40-7.19 (m, 5H), 7.03 (d, J=7.3 Hz, 1H), 6.91-6.82 (m, 2H), 4.51 (s, 2H), 4.46 (s, 2H), 4.41 (s, 2H), 4.34 (tt, J=12.2, 3.9 Hz, 1H), 3.74 (d, J=6.5 Hz, 2H), 3.64-3.56 (m, 2H), 3.21-3.04 (m, 2H), 2.91 (s, 3H), 2.32-2.17 (m, 2H), 2.07 (dq, J=13.3, 6.6 Hz, 1H), 1.97 (t, J=15.8 Hz, 2H), 1.04 (d, J=6.7 Hz, 6H), LCMS (ES, m/z): 422 $[M+H]^+$.

Example 2: Preparation of 7-fluoro-2-(1-methylpiperidin-4-yl)-4-[[4-(2-methylpropoxy)phenyl] methyl]-1,5-dihydro-2,4-benzo diazepine-3-one (A19001)

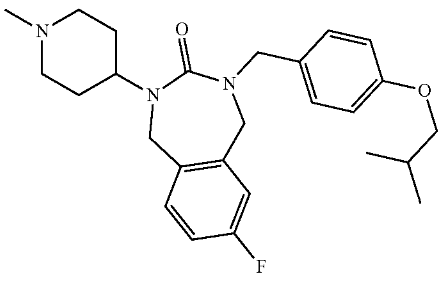

Synthetic Route:

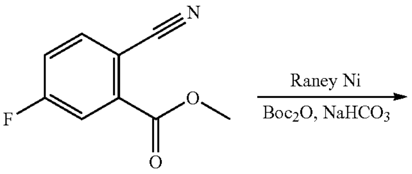

-continued

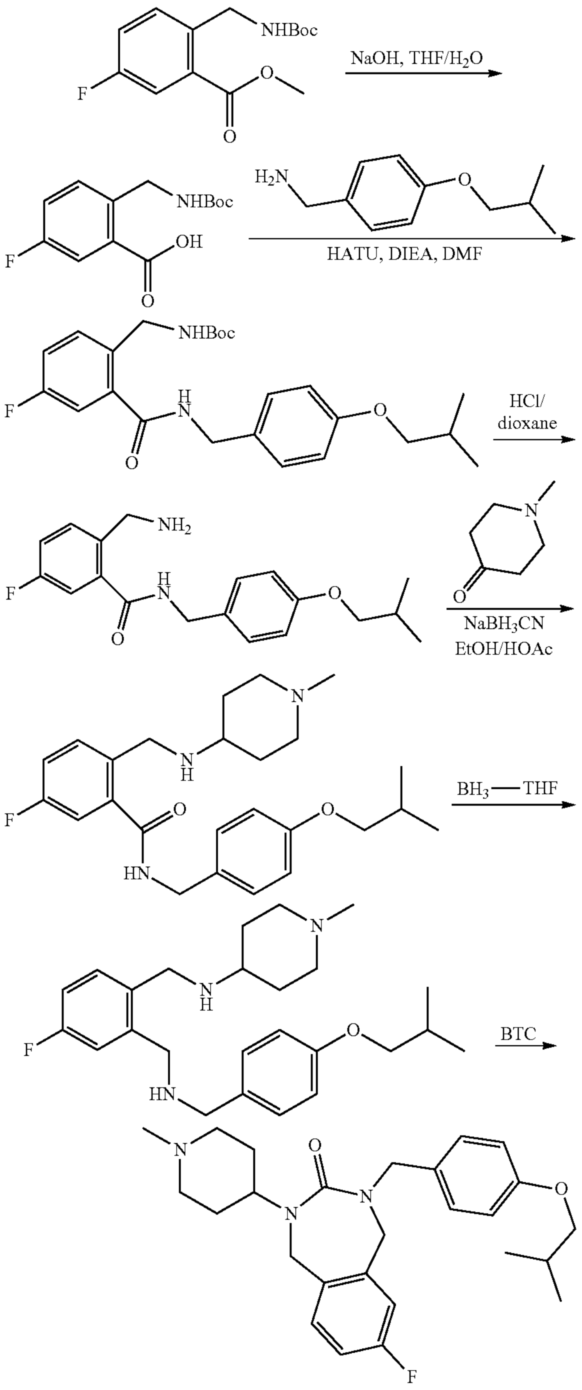

2.1 Preparation of methyl 2-[(tert-butoxycarbonyl) aminomethyl]-5-fluoro-benzoate Methyl 2-cyano-5-fluorobenzoate (1.8 g, 10.05 mmol), Raney-Ni (0.5 g), $Boc_2O$ (2.63 g, 12.06 mmol), $NaHCO_3$ (1.69 g, 20.1 mmol) and THF (20 mL) were added into a 50 mL three-necked round-bottom flask, with hydrogen purging, and the mixture was stirred at 50° C. for 48 h. The reaction mixture was filtered and the filtrate was directly concentrated to give a solid (2 g, yield 70.26%).

2.2 Preparation of 2-[(tert-butoxycarbonyl) aminomethyl]-5-fluoro-benzoic acid

Methyl 2-[(tert-butoxycarbonyl) aminomethyl]-5-fluoro-benzoate (2.0 g, 7.06 mmol), sodium hydroxide (1.41 g, 35.3 mmol), and THF/$H_2O$ (10/10 mL) were placed in a 50 mL three-necked round-bottom flask, and the mixture was stirred at room temperature overnight. The reaction mixture was adjusted to pH 5 with 3 N HCl, extracted with EA (3×20 mL), washed with saturated brine (30 mL), dried over anhydrous sodium sulfate, filtered under suction and concentrated to give a solid (1.2 g, yield 63.13%).

2.3 Preparation of 2-[(tert-butoxycarbonyl)aminomethyl]-5-fluoro-N-[4-(2-methylpropoxy)benzyl]benzamide 2-[(tert-butoxycarbonyl)aminomethyl]-5-fluoro-benzoic acid (1.2 g, 4.4 mmol), 4-isobutoxybenzylamine (0.88 g, 4.9 mmol), HATU (2.2 g, 5.8 mmol), DIEA (1.15 g, 8.9 mmol) and DMF (20 mL) were placed in a 50 mL three-necked round-bottom flask, and the mixture was stirred at room temperature overnight. The reaction mixture was added with water (30 mL), extracted with EA (3×20 mL), washed with saturated brine (30 mL), dried over anhydrous sodium sulfate, filtered under suction and concentrated, and the residue was purified by silica gel column chromatography (ethyl acetate/petroleum ether=1/3) to give a solid (1 g, yield 52.12%).

2.4 Preparation of 2-(aminomethyl)-5-fluoro-N-[4-(2-methylpropoxy)benzyl]benzamide The preparation was performed with reference to the step 1.10 of the method in Example 1 to give an oil (1 g).

2.5 Preparation of 2-[[(1-methylpiperidin-4-yl) amino]methyl]-5-fluoro-N-[4-(2-methylpropoxy) benzyl]benzamide 2-(aminomethyl)-5-fluoro-N-[4-(2-methylpropoxy)benzyl]benzamide (1 g, 3.02 mmol), 1-methylpiperidin-4-one (0.41 g, 3.6 mmol), $NaBH_3CN$ (0.38 g, 6.05 mmol), EtOH (10 mL) and HOAc (1 mL) were added into a 50 mL round-bottom flask, and the mixture was stirred overnight at room temperature. The reaction mixture was added with saturated $NaHCO_3$ solution (30 mL), extracted with EA (3×20 mL), washed with saturated brine (30 mL), dried over anhydrous sodium sulfate, filtered under suction and concentrated, and the residue was purified by silica gel column chromatography (dichloromethane/methanol=10/1) to give a solid (0.75 g, yield 57.96%).

2.6 Preparation of 2-[[(1-methylpiperidin-4-yl) amino]methyl]-5-fluoro-N-[4-(2-methylpropoxy) benzyl]benzylamine 2-[[(1-methylpiperidin-4-yl)amino]methyl]-5-fluoroN-[4-(2-methylpropoxy)benzyl]benzamide (0.3 g, 0.702 mmol) and $BH_3$-THF (10.00 mL) were placed in a 50 mL round-bottom flask, and the mixture was stirred at reflux overnight. The reaction mixture was quenched with 2 N HCl and added with EA (30 mL). The aqueous phase was extracted with EA (2×20 mL), adjusted to pH 10 with 15% NaOH solution, extracted with DCM, the solvent was removed, and the residue was purified by reverse-phase chromatography to give a white solid (0.1 g, yield 34.46%).

2.7 Preparation of 7-fluoro-2-(1-methylpiperidin-4-yl)-4-[[4-(2-methylpropoxy)phenyl]methyl]-1,5-dihydro-2,4-benzo diazepine-3-one The preparation was performed with reference to the step 1.9 of the method in Example 1 to give a white solid (2.8 mg, yield 2.63%). H-NMR (400 MHz, Methanol-$d_4$): δ 7.34 (dd, J=8.4, 5.4 Hz, 1H), 7.25-7.17 (m, 2H), 7.00 (td, J=8.6, 2.7 Hz, 1H), 6.91-6.82 (m, 2H), 6.77 (dd, J=9.1, 2.7 Hz, 1H), 4.47 (d, J=15.2 Hz, 4H), 4.39 (s, 2H), 4.43-4.27 (m, 1H), 3.74 (d, J=6.4 Hz, 2H), 3.64-3.56 (m, 2H), 3.21-3.10 (m, 2H), 2.90 (s, 3H), 2.32 (dd, J=13.4, 4.0 Hz, 1H), 2.25 (dd, J=13.1, 4.1 Hz, 1H), 2.06 (dp, J=13.3, 6.7 Hz, 1H), 1.95 (d, J=13.9 Hz, 2H), 1.04 (d, J=6.7 Hz, 6H); LCMS (ES, m/z): 440 $[M+H]^+$.

Example 3: Preparation of 7-chloro-2-(1-methylpiperidin-4-yl)-4-[[4-(2-methylpropoxy)phenyl]methyl]-1,5-dihydro-2,4-benzo diazepine-3-one (A190017)

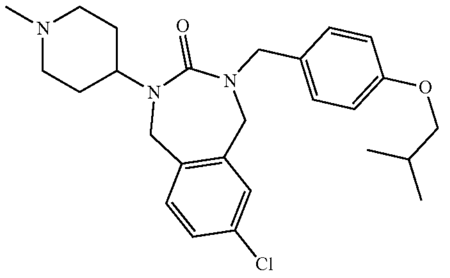 [SMILES: CC(C)COc1ccc(CN2Cc3cc(Cl)ccc3CN(C3CCN(C)CC3)C2=O)cc1]

Synthetic Route:

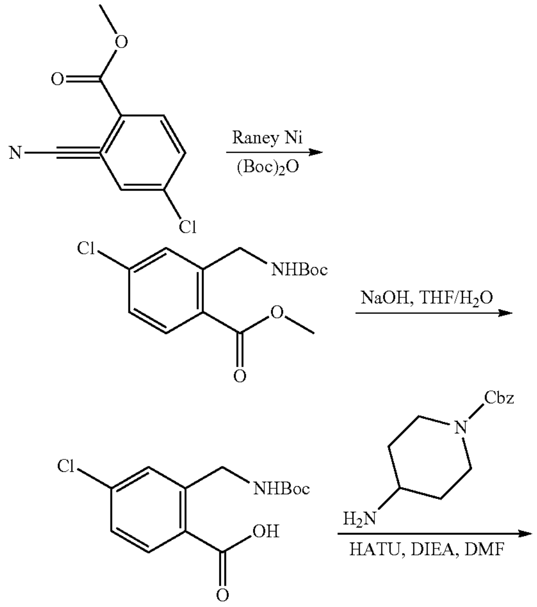

-continued

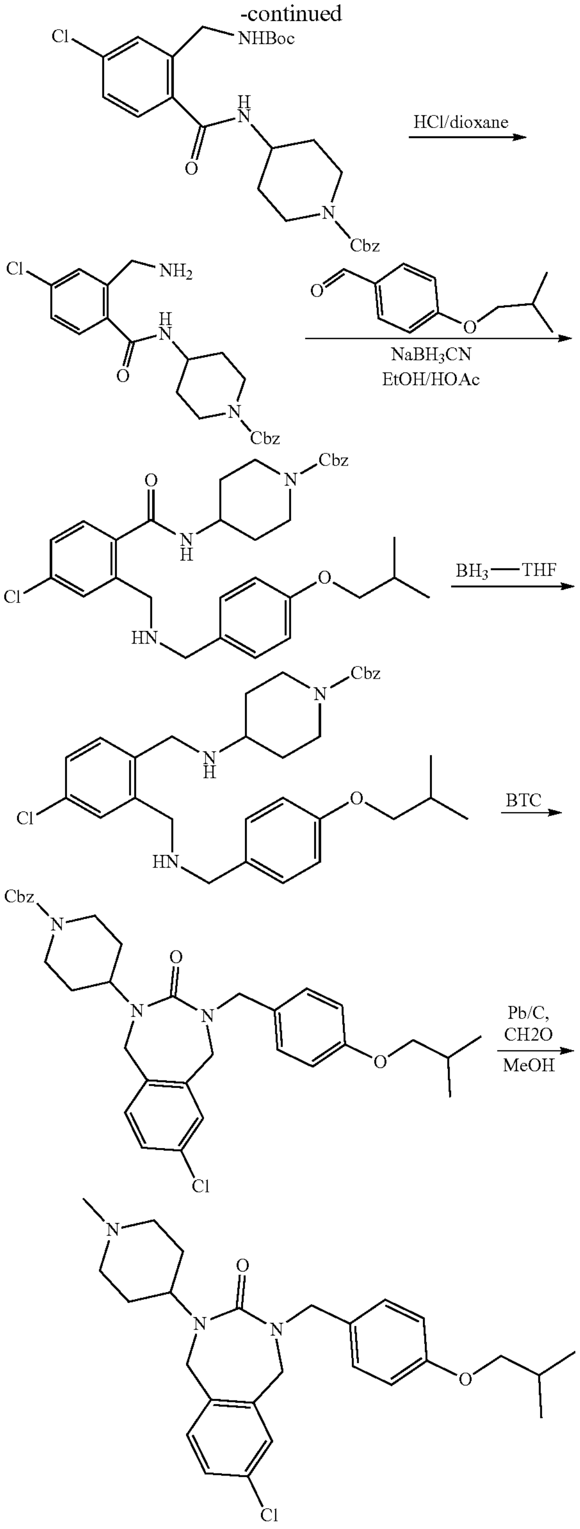

3.1 Preparation of methyl 2-[(tert-butoxycarbonyl) aminomethyl]-4-chloro-benzoate The preparation was performed with reference to the step 2.1 of the method in Example 2 to give a white solid (1.58 g, yield 103.10%).

3.2 Preparation of 2-[(tert-butoxycarbonyl)aminomethyl]-4-chloro-benzoic acid The preparation was performed with reference to the step 2.2 of the method in Example 2 to give a white solid (1.12 g, yield 74.37%).

3.3 Preparation of 2-[(tert-butoxycarbonyl)aminomethyl]-4-chloro-4(benzyl piperidine-1-carboxylate) benzamide The preparation was performed with reference to the step 2.3 of the method in Example 2 to give a yellow oil (2 g, yield 101.63%).

3.4 Preparation of 2-(aminomethyl)-4-chloro-4-(benzyl piperidine-1-carboxylate)benzamide The preparation was performed with reference to the step 1.10 of the method in Example 1 to give a white solid (2 g, yield 124.91%).

3.5 Preparation of 2-(2-methylpropoxy)-benzylamine-4-chloro-4-(benzyl piperidine-1-carboxylate) benzamide The preparation was performed with reference to the step 2.5 of the method in Example 2 to give a yellow oil (1 g, yield 35.62%).

3.6 Preparation of 2-(2-methylpropoxy)-benzylamine-4-chloro-4-(benzyl piperidine-1-carboxylate) benzylamine The preparation was performed with reference to the step 2.6 of the method in Example 2 to give a yellow oil (0.22 g, yield 22.56%).

3.7 Preparation of 7-chloro-2-(benzyl piperidine-1-carboxylate)-4-[[4-(2-methylpropoxy)phenyl] methyl]-1,5-dihydro-2,4-benzodiazepine-3-one The preparation was performed with reference to the step 1.9 of the method in Example 1 to give a yellow oil (0.21 g, yield 91.15%).

3.8 Preparation of 7-chloro-2-(1-methylpiperidin-4-yl)-4-[[4-(2-methylpropoxy)phenyl]methyl]-1,5-dihydro-2,4-benzo diazepine-3-one 7-chloro-2-(benzyl piperidine-1-carboxylate)-4-[[4-(2-methylpropoxy)phenyl]methyl]-1,5-dihydro-2,4-benzodiazepine-3-one (0.21 g, 0.365 mmol), Pd/C (77.58 mg, 0.729 mmol), HCHO (43.78 mg, 1.46 mmol) and MeOH (3 mL) were placed in a 50 mL round-bottom flask, and the mixture was stirred at room temperature for 10 h. The reaction mixture was filtered under suction, the filtrate was concentrated, and the residue was purified by preparative liquid chromatography to give a white solid (2.4 mg, yield 1.44%). $^1$H NMR (400 MHz, DMSO-$d_4$) δ 9.62 (s, 1H), 7.33 (dd, J=8.0, 2.2 Hz, 1H), 7.28-7.18 (m, 6H), 6.90-6.83 (m, 3H), 4.37-4.30 (m, 8H), 4.17 (d, J=12.6 Hz, 2H), 3.72 (d, J=6.5 Hz, 3H), 3.05 (d, J=10.8 Hz, 2H), 2.76 (d, J=4.7 Hz, 4H), 2.38 (s, 4H), 2.18-2.08 (m, 3H), 2.00 (dt, J=13.4, 6.7 Hz, 1H), 1.75 (d, J=13.3 Hz, 3H), 1.24 (s, 1H), 0.98 (d, J=6.7 Hz, 9H); LCMS (ES, m/z): 456 [M+H]$^+$.

Example 4: Preparation of 8-fluoro-2-(1-methylpiperidin-4-yl)-4-[[4-(2-methylpropoxy)phenyl] methyl]-1,5-dihydro-2,4-benzo diazepine-3-one (A19005)

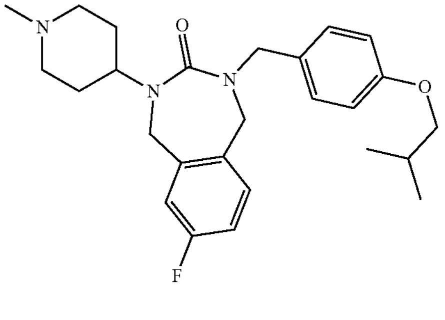 [SMILES: CC(C)COc1ccc(CN2Cc3ccc(F)cc3CN(C3CCN(C)CC3)C2=O)cc1]

Synthetic Route:

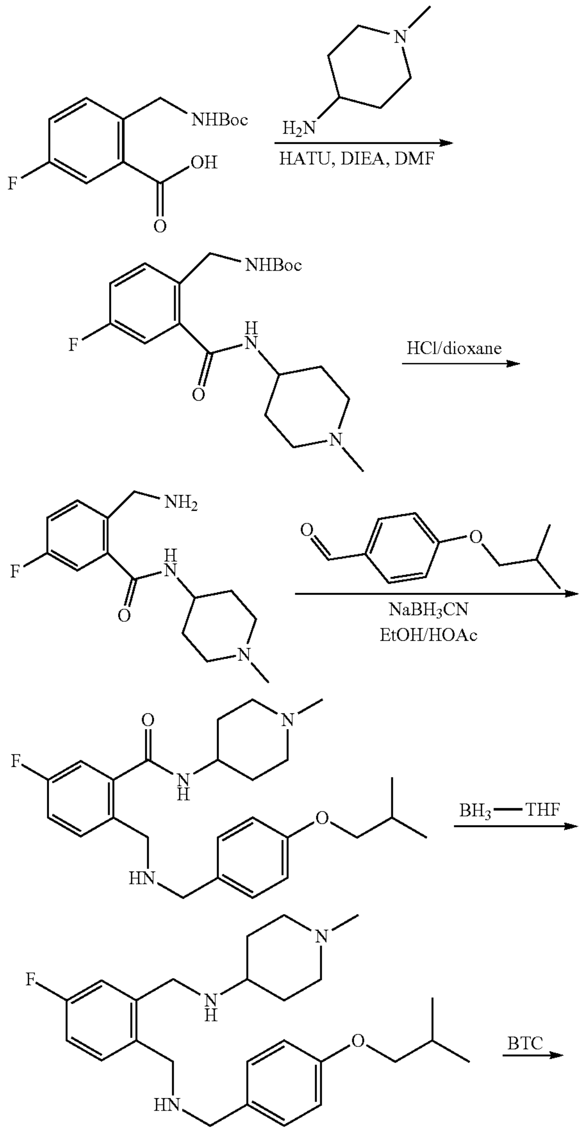

-continued

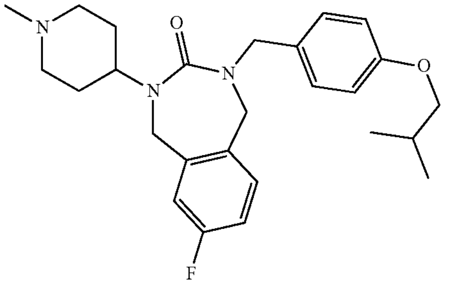

4.1 Preparation of 2-[(tert-butoxycarbonyl)aminomethyl]-5-fluoro-N-[4-(1-methylpiperidine)]benzamide The preparation was performed with reference to the step 2.3 of the method in Example 2 to give an oil (8g, yield 84.21%).

4.2 Preparation of 2-(aminomethyl)-5-fluoro-N-[4-(1-methylpiperidine)]benzamide

The preparation was performed with reference to the step 1.10 of the method in Example 1 to give an oil (2 g).

4.3 Preparation of 2-[[4-(2-methylpropoxy)-benzylamine]methyl]-5-fluoro-N-[4-(1-methylpiperidine)]benzamide The preparation was performed with reference to the step 2.5 of the method in Example 2 to give a yellow oil (0.65 g, yield 20.17%).

4.4 Preparation of 2-[[4-(2-methylpropoxy)-benzylamine]methyl]-5-fluoro-N-[4-(1-methylpiperidine)]benzylamine The preparation was performed with reference to the step 2.6 of the method in Example 2 to give a yellow oil (0.25 g, yield 12.31%).

4.5 Preparation of 8-fluoro-2-(1-methylpiperidin-4-yl)-4-[[4-(2-methylpropoxy)phenyl]methyl]-1,5-dihydro-2,4-benzo diazepine-3-one The preparation was performed with reference to the step 1.9 of the method in Example 1 to give a white solid (35 mg, yield 13.17%). H-NMR (400 MHz, Methanol-$d_4$) δ 7.24-7.17 (m, 2H), 7.11 (dd, J=9.0, 2.6 Hz, 1H), 7.03 (dd, J=8.4, 5.5 Hz, 1H), 6.95 (td, J=8.6, 2.6 Hz, 1H), 6.90-6.83 (m, 2H), 4.52-4.36 (m, 7H), 4.31 (tt, J=12.3, 3.9 Hz, 1H), 3.73 (d, J=6.5 Hz, 2H), 3.60 (d, J=12.4 Hz, 2H), 3.40 (s, OH), 3.15 (t, J=12.7 Hz, 2H), 2.91 (s, 3H), 2.25 (qd, J=13.3, 4.0 Hz, 2H), 2.06 (dt, J=13.3, 6.6 Hz, 1H), 1.96 (d, J=13.8 Hz, 2H), 1.04 (d, J=6.7 Hz, 6H); LCMS (ES, m/z): 440 $[M+H]^+$.

Example 5: Preparation of 8-fluoro-2-(1-methylpiperidin-4-yl)-4-[[4-(2-methylpropylamino)phenyl]methyl]-1,5-dihydro-2,4-benzodiazepine-3-one (A19007)

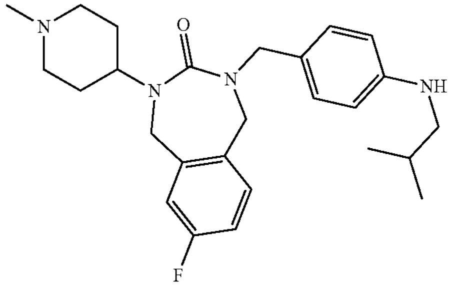 [SMILES: CC(C)CNc1ccc(CN2Cc3ccc(F)cc3CN(C3CCN(C)CC3)C2=O)cc1]

Synthetic Route:

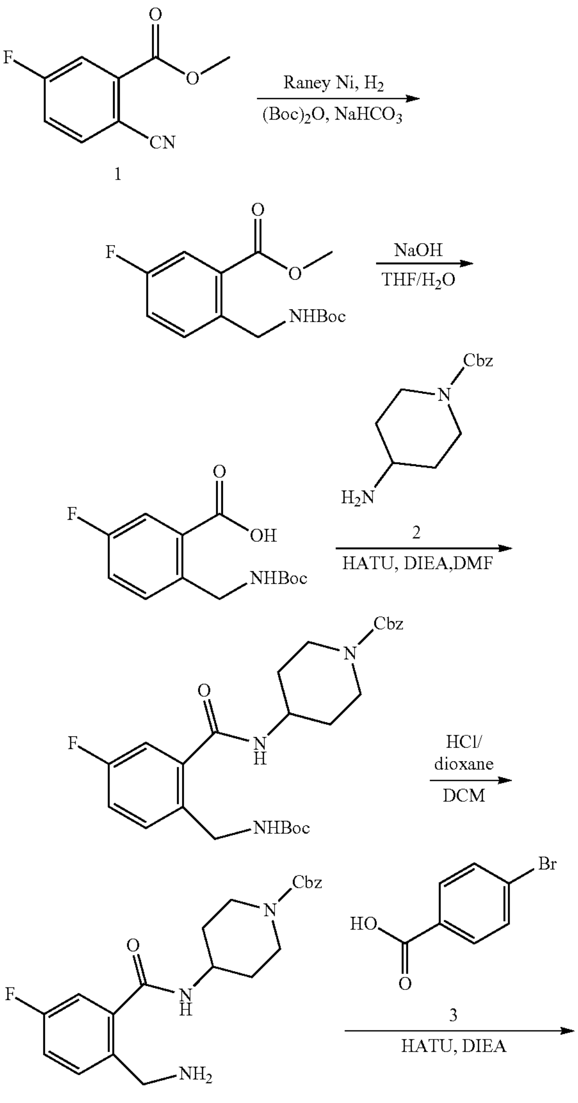

-continued

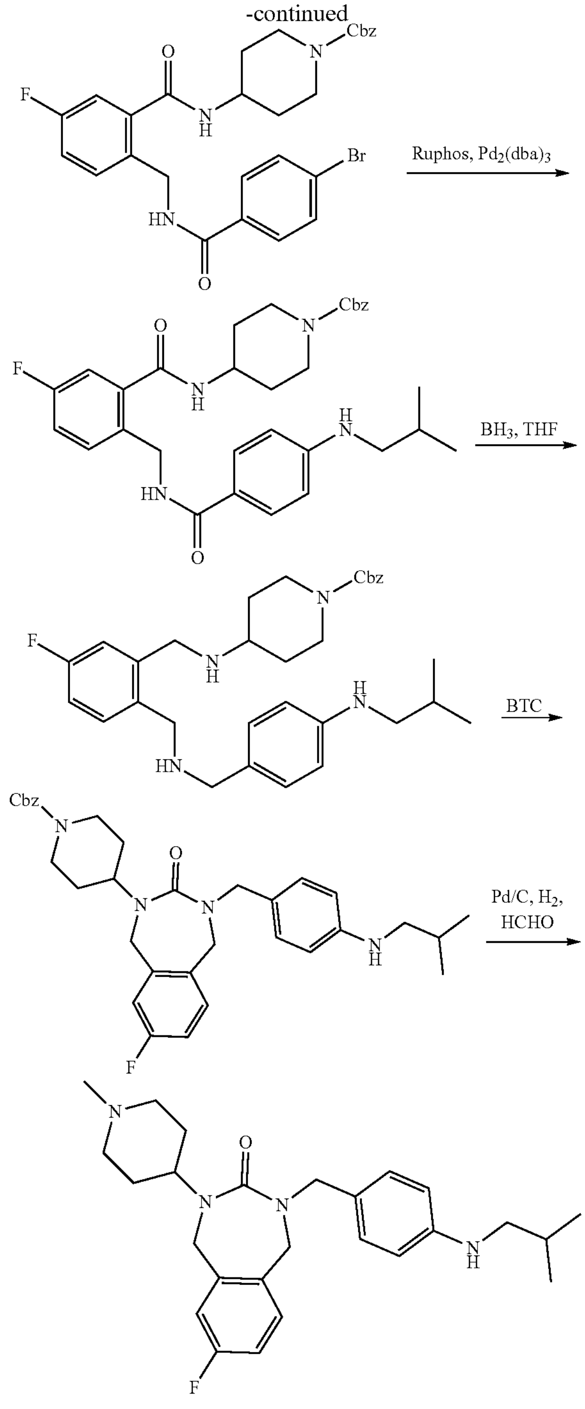

5.1 Preparation of methyl 2-[(tert-butoxycarbonyl) aminomethyl]-5-fluoro-benzoate The preparation was performed with reference to the step 2.1 of the method in Example 2 to give an oil (4.7 g).

5.2 Preparation of 2-[(tert-butoxycarbonyl)aminomethyl]-5-fluoro-benzoic acid The preparation was performed with reference to the step 2.2 of the method in Example 2 to give an oil (4.0 g, yield 89.54%).

5.3 Preparation of 2-[(tert-butoxycarbonyl)aminomethyl]-5-fluoro-N-[4-(benzyl piperidine-1-carboxylate)]benzamide The preparation was performed with reference to the step 2.3 of the method in Example 2 to give an oil (4.6 g).

5.4 Preparation of 2-(aminomethyl)-5-fluoro-N-[4-(benzyl piperidine-1-carboxylate)]benzamide The preparation was performed with reference to the step 1.10 of the method in Example 1 to give an oil (5.6 g).

5.5 Preparation of [2-(4-bromobenzamide)methyl]-5-fluoro-N-[4-(benzyl piperidine-1-carboxylate)] benzamide The preparation was performed with reference to the step 2.3 of the method in Example 2 to give a white solid (3.2 g, yield 38.75%).

5.6 Preparation of [2-[[4-(2-methylpropyl)amino-benzamide]methyl]-5-fluoro-N-[4-(benzyl piperidine-1-carboxylate)]benzamide

[2-(4-bromobenzamide)methyl]-5-fluoro-N-[4-(benzyl piperidine-1-carboxylate)]benzamide (lg, 1.76 mmol), isobutylamine (0.193 g, 2.64 mmol), sodium tert-butoxide (0.34 g, 3.52 mmol), Ruphos (82.1 mg, 0.176 mmol), $Pd_2(dba)_3$ (0.161 mg, 0.176 mmol) and toluene (13 mL) were placed in a 50 mL round-bottom flask, and the mixture was warmed up to 80° C. and stirred for 1 h. The reaction mixture was filtered under suction, the filtrate was concentrated, and the residue was purified by silica gel column chromatography (PE/EA=3:1) to give a yellow solid (0.797 g, yield 80.8%).

5.7 Preparation of benzyl 4-((5-fluoro-2-(((4-(isobutylamino)benzyl)amino)methyl)benzyl)amino) piperidine-1-carboxylate The preparation was performed with reference to the step 2.6 of the method in Example 2 to give a white solid (260 mg, yield 34.33%).

5.8 Preparation of 8-fluoro-2-(benzyl piperidine-1-carboxylate)-4-[[4-(2-methylpropylamino)phenyl] methyl]-1,5-dihydro-2,4-benzodiazepine-3-one The preparation was performed with reference to the step 1.9 of the method in Example 1 to give an oil (0.26 g).

5.9 Preparation of 8-fluoro-2-(1-methylpiperidin-4-yl)-4-[[4-(2-methylpropylamino)phenyl]methyl]-1,5-dihydro-2,4-benzodiazepine-3-one The preparation was performed with reference to the step 3.8 of the method in Example 3 to give a white solid (4.1 mg, yield 2.61%). $^1H$ NMR (400 MHz, Methanol-$d_4$) δ 8.48 (s, 1H, FA), 7.10-6.98 (m, 4H), 6.93 (td, J=8.6, 2.7 Hz, 1H), 6.58 (d, 2H), 4.42 (s, 4H), 4.36 (s, 2H), 4.30-4.18 (m, 1H), 3.46-3.39 (m, 2H), 2.96-2.83 (m, 4H), 2.77 (s, 3H), 2.25-2.05 (m, 2H), 1.96-1.84 (m, 3H), 1.36-1.30 (m, 1H), 0.99 (d, J=6.6 Hz, 6H); LCMS (ES, m/z): 439 $[M+H]^+$.

Compounds A19006, A19008, A19009, A19011, A19012, A19013, and A19015 were synthesized according to the following general synthetic route:

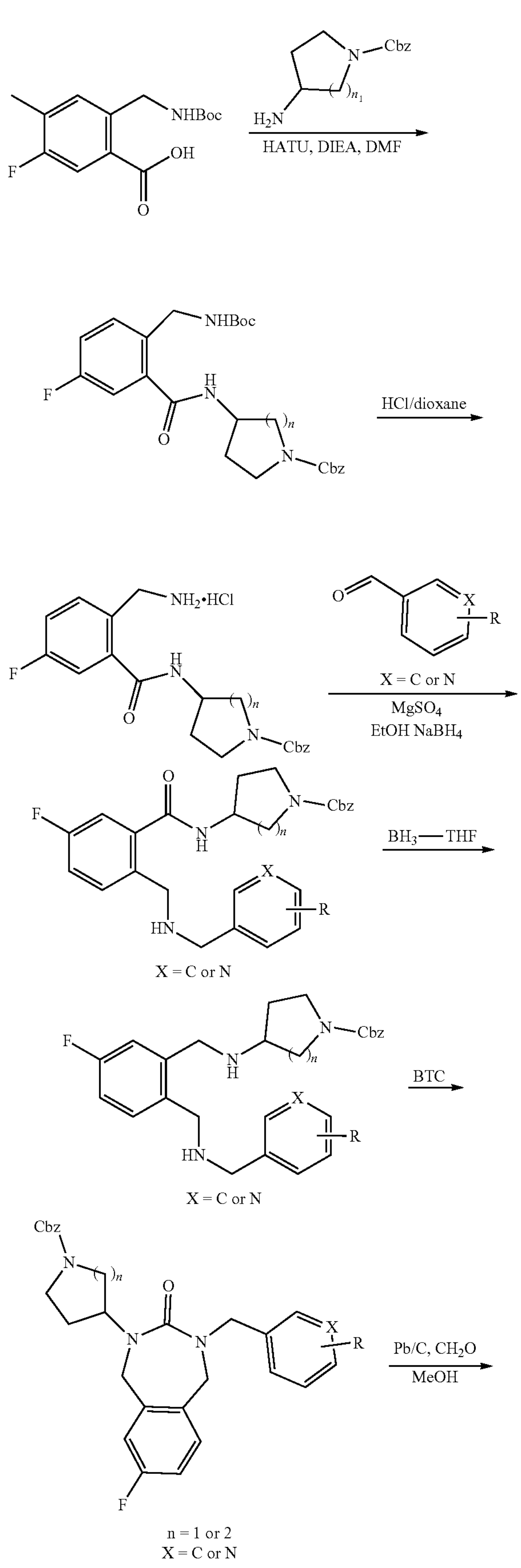

-continued

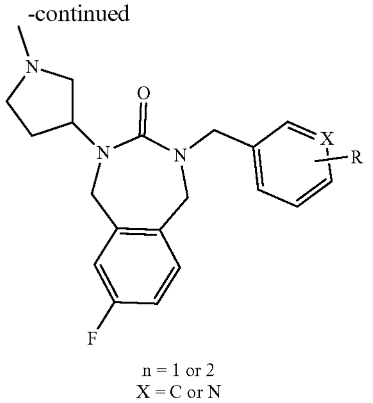

Example 6: Preparation of 8-fluoro-2-(1-methylpiperidin-4-yl)-4-[[4-(cyclopropoxy)phenyl]methyl]-1,5-dihydro-2,4-benzodiazepine-3-one (A19006)

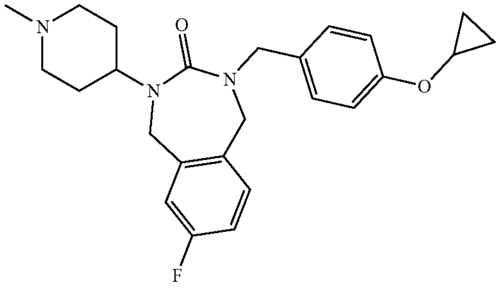 [SMILES: CN1CCC(N2Cc3cc(F)ccc3CN(Cc3ccc(OC4CC4)cc3)C2=O)CC1]

6.1 Preparation of 2-[(tert-butoxycarbonyl)aminomethyl]-5-fluoro-N-[4-(benzyl piperidine-1-carboxylate)]benzamide The preparation was performed with reference to the step 2.3 of the method in Example 2 to give a yellow solid (23 g, yield 63.77%).

6.2 Preparation of 2-(aminomethyl)5-fluoro-N-[4-(benzyl 1-piperidine-1-carboxylate)]benzamide hydrochloride The preparation was performed with reference to the step 1.10 of the method in Example 1 to give an oil (1.9 g).

6.3 Preparation of 2-[4-(cyclopropoxy)-benzylaminemethyl]-5-fluoro-N-[4-(benzyl piperidine-1-carboxylate)]benzamide The preparation was performed with reference to the step 1.7 of the method in Example 1 to give an oil (1.3 g).

6.4 Preparation of 2-[4-(cyclopropoxy)-benzylaminemethyl]-5-fluoro-N-[4-(benzyl piperidine-1-carboxylate)]benzylamine The preparation was performed with reference to the step 2.6 of the method in Example 2 to give a yellow oil (0.23 g, yield 18.17%).

6.5 Preparation of 8-fluoro-2-[4-(benzyl piperidine-1-carboxylate)-4-[[4-(cyclopropoxy)phenyl]methyl]-1,5-dihydro-2,4-benzodiazepine-3-one The preparation was performed with reference to the step 1.9 of the method in Example 1 to give an oil (0.2 g).

6.6 Preparation of 8-fluoro-2-(1-methylpiperidin-4-yl)-4-[[4-(cyclopropoxy)phenyl]methyl]-1,5-dihydro-2,4-benzodiazepine-3-one The preparation was performed with reference to the step 3.8 of the method in Example 3 to give a brown solid (37.9 mg, yield 24.32%). $^1H$ NMR (400 MHz, DMSO-$d_6$) δ 7.30-7.19 (m, 3H), 7.11 (dd, J=8.4, 5.7 Hz, 1H), 7.05-6.94 (m, 3H), 4.36 (d, J=7.1 Hz, 4H), 4.29 (s, 2H), 3.96 (tt, J=11.4, 4.0 Hz, 1H), 3.80 (tt, J=6.0, 3.0 Hz, 1H), 2.86-2.78 (m, 2H), 2.16 (s, 3H), 1.95-1.85 (m, 2H), 1.89-1.75 (m, 2H), 1.45 (dd, J=11.0, 3.9 Hz, 2H), 0.81-0.67 (m, 2H), 0.67-0.59 (m, 2H); LCMS (ES, m/z): 424 $[M+H]^+$.

Example 7: Preparation of 8-fluoro-2-(1-methylpiperidin-4-yl)-4-[[4-(2-methylpropyl)phenyl]methyl]-1,5-dihydro-2,4-benzodiazepine-3-one (A19008)

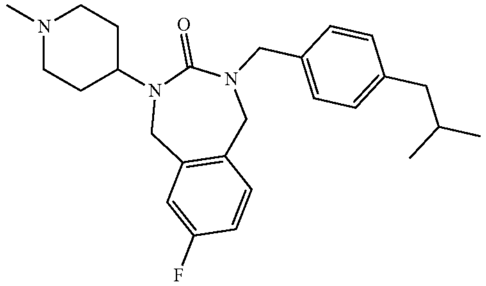 [SMILES: CC(C)Cc1ccc(CN2Cc3ccc(F)cc3CN(C3CCN(C)CC3)C2=O)cc1]

7.1 Preparation of 2-[4-[(2-methylpropyl)-benzylaminemethyl]-5-fluoro-N-[4-(benzyl piperidine-1-carboxylate)]benzamide The preparation was performed with reference to the step 1.7 of the method in Example 1 to give a yellow oil (2.3 g, yield 61.76%).

7.2 Preparation of 2-[4-(2-methylpropyl)-benzylamine-methyl]-5-fluoro-N-[4-(benzylpiperidine-1-carboxylate)]benzylamine The preparation was performed with reference to the step 2.6 of the method in Example 2 to give a yellow oil (0.69 g).

7.3 Preparation of 8-fluoro-2-[4-(benzyl piperidine-1-carboxylate)]-4-[[4-(2-methylpropyl)phenyl] methyl]-1,5-dihydro-2,4-benzodiazepine-3-one The preparation was performed with reference to the step 1.9 of the method in Example 1 to give a yellow oil (0.7 g).

7.4 Preparation of 8-fluoro-2-(1-methylpiperidin-4-yl)-4-[[4-(2-methylpropyl)phenyl]methyl]-1,5-dihydro-2,4-benzodiazepine-3-one The preparation was performed with reference to the step 3.8 of the method in Example 3 to give a yellow solid (21 mg, yield 3.85%). $^1H$ NMR (400 MHz, DMSO-$d_6$) δ 10.87 (s, 1H), 7.23-6.96 (m, 7H), 4.43 (d, J=7.8 Hz, 4H), 4.34 (s, 3H), 3.86 (s, 1H), 3.45-3.37 (m, 2H), 3.17 (s, 1H), 3.11-2.95 (m, 2H), 2.71 (d, J=4.8 Hz, 3H), 2.44-2.27 (m, 4H), 1.80 (dp, J=13.5, 6.8 Hz, 1H), 1.72-1.59 (m, 2H), 0.85 (d, J=6.6 Hz, 6H); LCMS (ES, m/z): 424 $[M+H]^+$.

Example 8: Preparation of 8-fluoro-2-(1-methylpiperidin-4-yl)-4-[(4-methoxyphenyl)methyl]-1,5-dihydro-2,4-benzodiazepine-3-one (A19009)

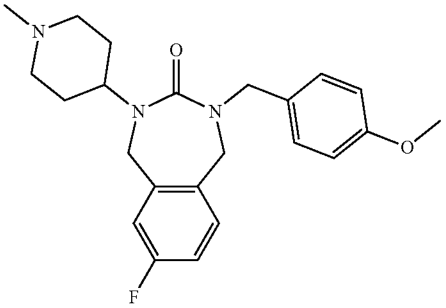

8.1 Preparation of 2-[(4-methoxy)-benzylamine-methyl]-5-fluoro-N-[4-(benzyl piperidine-1-carboxylate)]benzamide The preparation was performed with reference to the step 1.7 of the method in Example 1 to give a yellow oil (0.48 g).

8.2 Preparation of 2-[(4-methoxy)-benzylamine-methyl]-5-fluoro-N-[4-(benzyl piperidine-1-carboxylate)]benzylamine The preparation was performed with reference to the step 2.6 of the method in Example 2 to give a yellow oil (0.13 g).

8.3 Preparation of 8-fluoro-2-[4-(benzyl piperidine-1-carboxylate)]-4-[(4-methoxyphenyl)methyl]-1,5-dihydro-2,4-benzodiazepine-3-one The preparation was performed with reference to the step 1.9 of the method in Example 1 to give a yellow oil (0.09 g).

8.4 Preparation of 8-fluoro-2-(1-methylpiperidin-4-yl)-4-[(4-methoxyphenyl)methyl]-1,5-dihydro-2,4-benzodiazepine-3-one The preparation was performed with reference to the step 3.8 of the method in Example 3 to give a white solid (9 mg, yield 13.2%). $^1H$ NMR (400 MHz, DMSO-$d_6$) δ 7.25 (dd, J=11.0, 7.5 Hz, 3H), 7.10 (dd, J=8.5, 5.7 Hz, 1H), 7.01 (td, J=8.7, 2.7 Hz, 1H), 6.87 (d, J=8.4 Hz, 2H), 4.36 (d, J=7.2 Hz, 4H), 4.28 (s, 2H), 4.03-3.92 (m, 1H), 3.73 (s, 3H), 2.85 (d, J=9.8 Hz, 2H), 2.20 (s, 3H), 1.96 (s, 2H), 1.91-1.77 (m, 2H), 1.46 (d, J=11.2 Hz, 2H); LCMS (ES, m/z): 398 $[M+H]^+$.

Example 9: Preparation of 8-fluoro-2-(1-methylpiperidin-4-yl)-4-[[(2-fluoro-4-isopropoxy)phenyl]methyl]-1,5-dihydro-2,4-benzodiazepine-3-one (A19011)

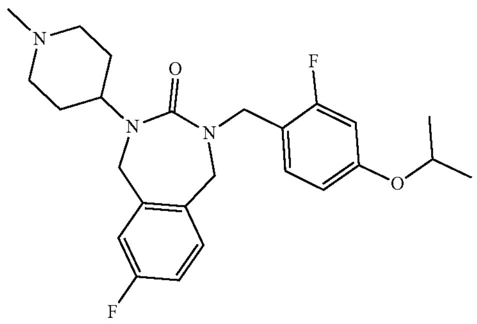 [SMILES: CC(C)Oc1ccc(CN2Cc3ccc(F)cc3CN(C3CCN(C)CC3)C2=O)c(F)c1]

9.1 Preparation of 2-[(2-fluoro-4-isopropoxy)-benzylamine-methyl]-5-fluoro-N-[4-(benzyl piperidine-1-carboxylate)]benzamide The preparation was performed with reference to the step 1.7 of the method in Example 1 to give a yellow oil (0.88 g).

9.2 Preparation of 2-[(2-fluoro-4-isopropoxy)-benzylamine-methyl]-5-fluoro-N-[4-(benzyl piperidine-1-carboxylate)]benzylamine The preparation was performed with reference to the step 2.6 of the method in Example 2 to give a yellow oil (0.117 g).

9.3 Preparation of 8-fluoro-2-[4-(benzyl piperidine-1-carboxylate)]-4-[[(2-fluoro-4-isopropoxy)phenyl]methyl]-1,5-dihydro-2,4-benzodiazepine-3-one The preparation was performed with reference to the step 1.9 of the method in Example 1 to give a yellow oil (0.09 g).

9.4 Preparation of 8-fluoro-2-(1-methylpiperidin-4-yl)-4-[[(2-fluoro-4-isopropoxy)phenyl]methyl]-1,5-dihydro-2,4-benzodiazepine-3-one The preparation was performed with reference to the step 3.8 of the method in Example 3 to give an orange solid (5.3 mg, yield 7.5%). $^{1}$H NMR (400 MHz, DMSO-$d_6$) δ 9.54 (s, 1H), 7.22-7.00 (m, 4H), 6.76 (dd, J=12.4, 2.5 Hz, 1H), 6.69 (dd, J=8.5, 2.5 Hz, 1H), 4.60 (p, J=6.0 Hz, 1H), 4.42 (s, 2H), 4.36 (d, J=16.6 Hz, 4H), 2.76 (d, J=4.7 Hz, 3H), 2.14-2.04 (m, 1H), 1.74 (d, J=14.9 Hz, 2H), 1.25 (d, J=5.9 Hz, 7H); LCMS (ES, m/z): 444 $[M+H]^+$.

Example 10: Preparation of 8-fluoro-2-(1-methylpiperidin-4-yl)-4-[[(3-fluoro-4-isopropoxy)phenyl]methyl]-1,5-dihydro-2,4-benzodiazepine-3-one (A19012)

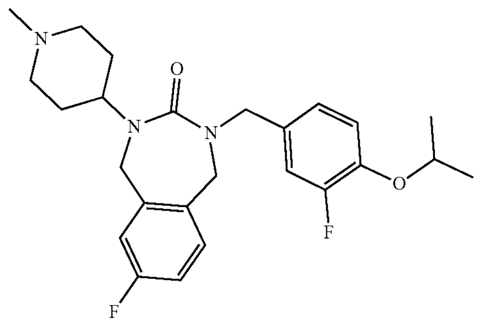 [SMILES: CC(C)Oc1ccc(CN2Cc3ccc(F)cc3CN(C3CCN(C)CC3)C2=O)cc1F]

10.1 Preparation of 2-[(3-fluoro-4-isopropoxy)-benzylamine-methyl]-5-fluoro-N-[4-(benzyl piperidine-1-carboxylate)]benzamide The preparation was performed with reference to the step 1.7 of the method in Example 1 to give a yellow oil (1.0 g).

10.2 Preparation of 2-[(3-fluoro-4-isopropoxy)-benzylamine-methyl]-5-fluoro-N-[4-(benzyl piperidine-1-carboxylate)]benzylamine The preparation was performed with reference to the step 2.6 of the method in Example 2 to give a yellow oil (0.118 g).

10.3 Preparation of 8-fluoro-2-[4-(benzyl piperidine-1-carboxylate)]-4-[[(3-fluoro-4-isopropoxy)phenyl]methyl]-1,5-dihydro-2,4-benzodiazepine-3-one The preparation was performed with reference to the step 1.9 of the method in Example 1 to give a yellow oil (0.11 g).

10.4 Preparation of 8-fluoro-2-(1-methylpiperidin-4-yl)-4-[[(3-fluoro-4-isopropoxy)phenyl]methyl]-1,5-dihydro-2,4-benzodiazepine-3-one The preparation was performed with reference to the step 3.8 of the method in Example 3 to give a yellow oil (4.3 mg, yield 4.9%). $^{1}$H NMR (400 MHz, DMSO-$d_6$) δ 9.16 (s, 1H), 7.18 (dd, J=8.3, 5.6 Hz, 1H), 7.15-7.01 (m, 5H), 4.58 (p, J=6.0 Hz, 1H), 4.40-4.32 (m, 6H), 4.16 (s, 1H), 2.78 (d, J=4.4 Hz, 3H), 2.44 (s, 12H), 2.05 (q, J=12.9, 12.3 Hz, 2H), 1.78 (d, J=13.5 Hz, 2H), 1.27 (d, J=6.0 Hz, 6H), 1.24 (s, 1H); LCMS (ES, m/z): 444 $[M+H]^+$.

Example 11: Preparation of 8-fluoro-2-(1-methylpiperidin-4-yl)-4-[[(6-isopropoxy)pyridin-3-yl]methyl]-1,5-dihydro-2,4-benzodiazepine-3-one (A19013)

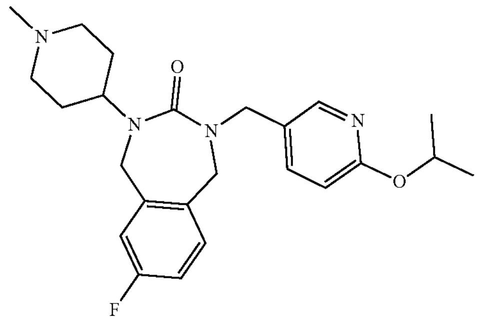 [SMILES: CC(C)Oc1ccc(CN2Cc3ccc(F)cc3CN(C3CCN(C)CC3)C2=O)cn1]

11.1 Preparation of 2-[(6-isopropoxypyridin-3-yl)-methyl-aminomethyl]-5-fluoro-N-[4-(benzyl piperidine-1-carboxylate)]benzamide The preparation was performed with reference to the step 1.7 of the method in Example 1 to give a yellow oil (2.4 g).

11.2 Preparation of 2-[(6-isopropoxypyridin-3-yl)-methyl-aminomethyl]-5-fluoro-N-[4-(benzyl piperidine-1-carboxylate)]benzylamine The preparation was performed with reference to the step 2.6 of the method in Example 2 to give a yellow oil (0.38 g).

11.3 Preparation of 8-fluoro-2-[4-(benzyl piperidine-1-carboxylate)]-4-[[(6-isopropoxy)pyridin-3-yl]methyl]-1,5-dihydro-2,4-benzodiazepine-3-one The preparation was performed with reference to the step 1.9 of the method in Example 1 to give a yellow oil (0.37 g).

11.4 Preparation of 8-fluoro-2-(1-methylpiperidin-4-yl)-4-[[(6-isopropoxy)pyridin-3-yl]methyl]-1,5-dihydro-2,4-benzodiazepine-3-one The preparation was performed with reference to the step 3.8 of the method in Example 3 to give a white solid (50.6 mg, yield 17.3%). $^1H$ NMR (400 MHz, DMSO-$d_6$) S $^1H$ NMR (400 MHz, DMSO-$d_6$) δ 8.09 (s, 1H), 7.62 (d, J=8.6 Hz, 1H), 7.27 (d, J=9.3 Hz, 1H), 7.15 (t, J=7.1 Hz, 1H), 7.02 (t, J=8.3 Hz, 1H), 6.67 (d, J=8.6 Hz, 1H), 5.21 (dt, J=13.0, 6.6 Hz, 1H), 4.39-4.31 (m, 6H), 3.98 (d, J=12.3 Hz, 1H), 2.82 (d, J=10.3 Hz, 2H), 2.17 (s, 3H), 1.88 (dt, J=28.7, 12.2 Hz, 4H), 1.48-1.40 (m, 2H), 1.27 (d, J=6.1 Hz, 6H); LCMS (ES, m/z): 427 $[M+H]^+$.

Example 12: Preparation of 8-fluoro-2-(1-methylpyrrol-3-yl)-4-[[(4-isobutoxy)phenyl]methyl]-1,5-dihydro-2,4-benzodiazepine-3-one (A19015)

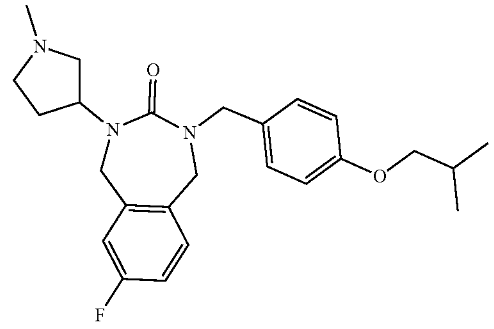 [SMILES: CC(C)COc1ccc(CN2Cc3ccc(F)cc3CN(C3CCN(C)C3)C2=O)cc1]

12.1 Preparation of 2-[(4-isobutoxy)benzylamine methyl]-5-fluoro-N-[3-(benzyl pyrrole-1-carboxylate)]benzamide The preparation was performed with reference to the step 1.7 of the method in Example 1 to give a yellow oil (3.3 g).

12.2 Preparation of 2-[4-(isobutoxy)benzylamine methyl]-5-fluoro-N-[3-(benzyl pyrrole-1-carboxylate)]benzylamine The preparation was performed with reference to the step 2.6 of the method in Example 2 to give a colorless oil (0.32 g).

12.3 Preparation of 8-fluoro-2-[3-(benzyl pyrrole-1-carboxylate)]-4-[[(4-isobutoxy)phenyl]methyl]-1,5-dihydro-2,4-benzodiazepine-3-one The preparation was performed with reference to the step 1.9 of the method in Example 1 to give a yellow oil (0.31 g).

12.4 Preparation of 8-fluoro-2-(1-methylpyrrol-3-yl)-4-[[(4-isobutoxy)phenyl]methyl]-1,5-dihydro-2,4-benzodiazepine-3-one The preparation was performed with reference to the step 3.8 of the method in Example 3 to give a white solid (47.3 mg, yield 18.6%). $^1H$ NMR (400 MHz, DMSO-$d_6$) S $^1H$ NMR (400 MHz, DMSO-$d_6$) δ 8.53 (s, 1H), 7.23-7.17 (m, 2H), 7.09 (dd, J=9.0, 2.6 Hz, 1H), 7.02 (dd, J=8.3, 5.5 Hz, 1H), 6.94 (td, J=8.6, 2.6 Hz, 1H), 6.89-6.82 (m, 2H), 4.67-4.28 (m, 7H), 3.73 (d, J=6.4 Hz, 2H), 3.70-3.55 (m, 2H), 3.28 (dd, J=11.9, 8.8 Hz, 1H), 3.04 (td, J=10.5, 8.2 Hz, 1H), 2.87 (s, 3H), 2.55-2.43 (m, 1H), 2.15 (ddt, J=13.6, 8.8, 4.6 Hz, 1H), 2.05 (dq, J=13.3, 6.7 Hz, 1H), 1.04 (d, J=6.7 Hz, 6H); LCMS (ES, m/z): 426 $[M+H]^+$.

Example 13: Preparation of 7-fluoro-1'-methyl-2-[[4-(2-methylpropoxy)phenyl]methyl]-1,2-dihydrospiro[benzo[c]azepine-4,4'-piperidine]-3(5H)-one (A19019)

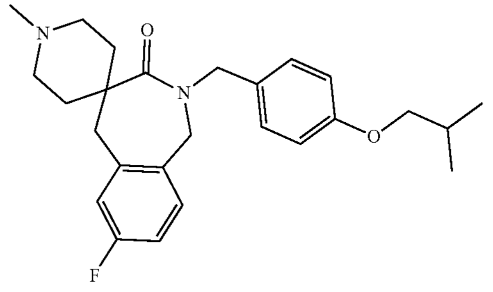 [SMILES: CC(C)COc1ccc(CN2Cc3ccc(F)cc3CC3(CCN(C)CC3)C2=O)cc1]

Synthetic Route:

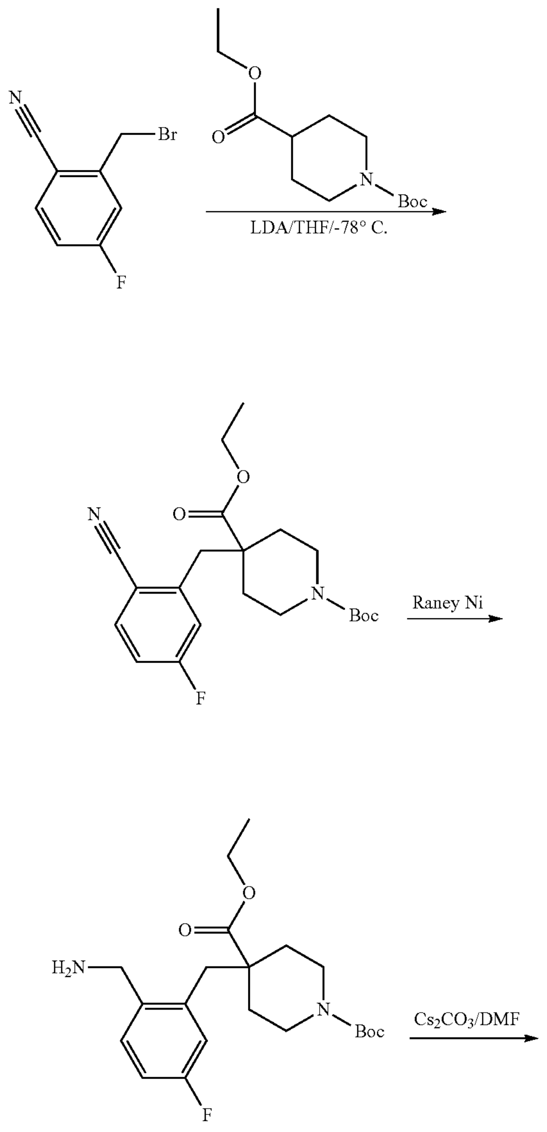

-continued

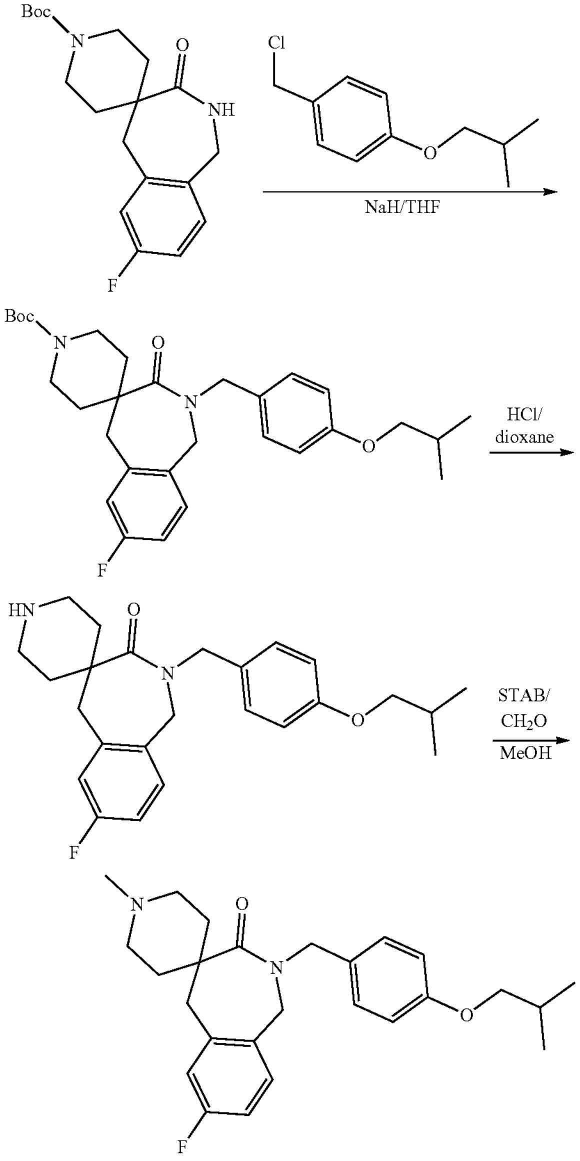

13.1 Preparation of 1-tert-butyl-4-ethyl 4-[(2-cyano-5-fluorophenyl)methyl]piperidine-1,4-dicarboxylate 2-(bromomethyl)-4-fluorobenzonitrile (2.5 g, 11.680 mmol), LDA (1.38 g, 12.88 mmol) and THF (25 mL) were placed in a 100 mL three-necked round bottom flask, and the mixture was stirred at room temperature overnight. After purging with nitrogen for 30 min, 1-tert-butyl 4-ethylpiperidine-1,4-dicarboxylate (3.01 g, 0.012 mol) was added dropwise at −78° C., and the resulting mixture was stirred at room temperature overnight under nitrogen atmosphere. The reaction mixture was added with saturated $NH_4Cl$ (200 mL) solution to quench the reaction, and extracted with EtOAc (3x25 mL). The resulting mixture was washed with brine (2x25 mL), dried over anhydrous $Na_2SO4$ and filtered, and the filtrate was concentrated under reduced pressure and eluted by silica gel column chromatography (PE/EtOAc=3:1) to give a yellow solid (3.5 g, yield 76.74%).

13.2 Preparation of 1-tert-butyl-4-ethyl 4-[(2-aminomethyl-5-fluorophenyl)methyl]piperidine-1,4-dicarboxylate The preparation was performed with reference to the step 2.1 of the method in Example 2 to give a white solid (1.5 g, yield 55.4%).

13.3 Preparation of tert-butyl-7-fluoro-3-oxo-1,2,3,5-tetrahydrospiro[benzo[c]azepine-4,4'-piperidine]-1'-carboxylate 1-tert-butyl-4-ethyl 4-[(2-aminomethyl-5-fluorophenyl)methyl]piperidine-1,4-dicarboxylate (1 g, 2.54 mmol), $Cs_2CO_3$ (2.48 g, 0.008 mol) and DMF (10 mL) were placed in a 50 mL three-necked round-bottom flask, and the mixture was purged with nitrogen and stirred at 80° C. for 2 h. The reaction mixture was filtered, and the filtrate was added with water (20 mL) and extracted with EtOAc (3×20 mL). The resulting mixture was washed with brine (3×20 mL), dried over anhydrous $Na_2SO_4$ and filtered, and the filtrate was concentrated under reduced pressure to give a yellow solid (0.83 g, yield 93.9%).

13.4 Preparation of tert-butyl 7-fluoro-2-[[4-(2-methylpropoxy)phenyl]methyl]-3-oxo-1,2,3,5-tetrahydrospiro[benzo[c]azepine-4,4'-piperidine]-1'-carboxylate tert-butyl-7-fluoro-3-oxo-1,2,3,5-tetrahydrospiro[benzo[c]azepine-4,4'-piperidine]-1'-carboxylate (0.48 g, 1.38 mmol) and tetrahydrofuran (4 mL) were placed in a 50 mL three-necked round-bottom flask, NaH (91 mg, 2.29 mmol) was added at 0° C. under nitrogen atmosphere, and 1-(chloromethyl)-4-(2-methylpropoxy)benzene (0.27 g, 1.37 mmol) was added dropwise at room temperature. After the reaction was completed, the reaction mixture was added with water to quench the reaction and extracted with EtOAc (3×10 mL). The resulting mixture was washed with brine (2×20 mL), dried over anhydrous $Na_2SO_4$ and filtered, and the filtrate was concentrated under reduced pressure to give a yellow solid (0.5 g, yield 71.4%).

13.5 Preparation of 7-fluoro-2-[[4-(2-methylpropoxy)phenyl]methyl]-1,2-dihydrospiro[benzo[c]azepine-4,4'-piperidine]-3(5H)-one The preparation was performed with reference to the step 1.10 of the method in Example 1 to give an oil (0.4 g).

13.6 Preparation of 7-fluoro-1'-methyl-2-[[4-(2-methylpropoxy)phenyl]methyl]-1,2-dihydrospiro[benzo[c]azepine-4,4'-piperidine]-3(5H)-one 7-fluoro-2-[[4-(2-methylpropoxy)phenyl]methyl]-1,2-dihydrospiro[benzo[c]azepine-4,4'-piperidine]-3(5H)-one (0.4 g, 0.97 mmol), HCHO (58 mg, 1.9 mmol), HOAc (292 mg, 4.8 mmol) and MeOH (4 mL) were placed in a 50 mL three-necked round-bottom flask, and the mixture was stirred for 30 min under nitrogen atmosphere, followed by the addition of STAB (309 mg, 1.461 mmol) at room temperature. After the reaction was completed, the reaction mixture was added with water and extracted with EtOAc (3×10 mL). The resulting mixture was washed with brine (2×20 mL), dried over anhydrous $Na_2SO_4$ and filtered, and the filtrate was concentrated under reduced pressure. The crude product was purified by preparative high performance liquid chromatography to give a white solid (7.6 mg, yield 1.84%). $^1H$ NMR (400 MHz, DMSO-$d_6$) δ 7.20-7.06 (m, 4H), 6.96 (td, J=8.7, 2.7 Hz, 1H), 6.91-6.83 (m, 2H), 4.56 (s, 2H), 4.42 (s, 2H), 3.72 (d, J=6.5 Hz, 2H), 3.09 (s, 2H), 2.58 (dt, J=11.4, 3.6 Hz, 2H), 2.32-2.21 (m, 2H), 2.21 (s, 3H), 2.15 (td, J=12.7, 4.2 Hz, 2H), 2.01 (dq, J=13.3, 6.6 Hz, 1H), 1.34 (d, J=12.9 Hz, 2H), 0.98 (d, J=6.7 Hz, 6H); LCMS (ES, m/z): 425 $[M+H]^+$.

Compounds A19014-0 and A19014-0A were synthesized according to the following general synthetic route:

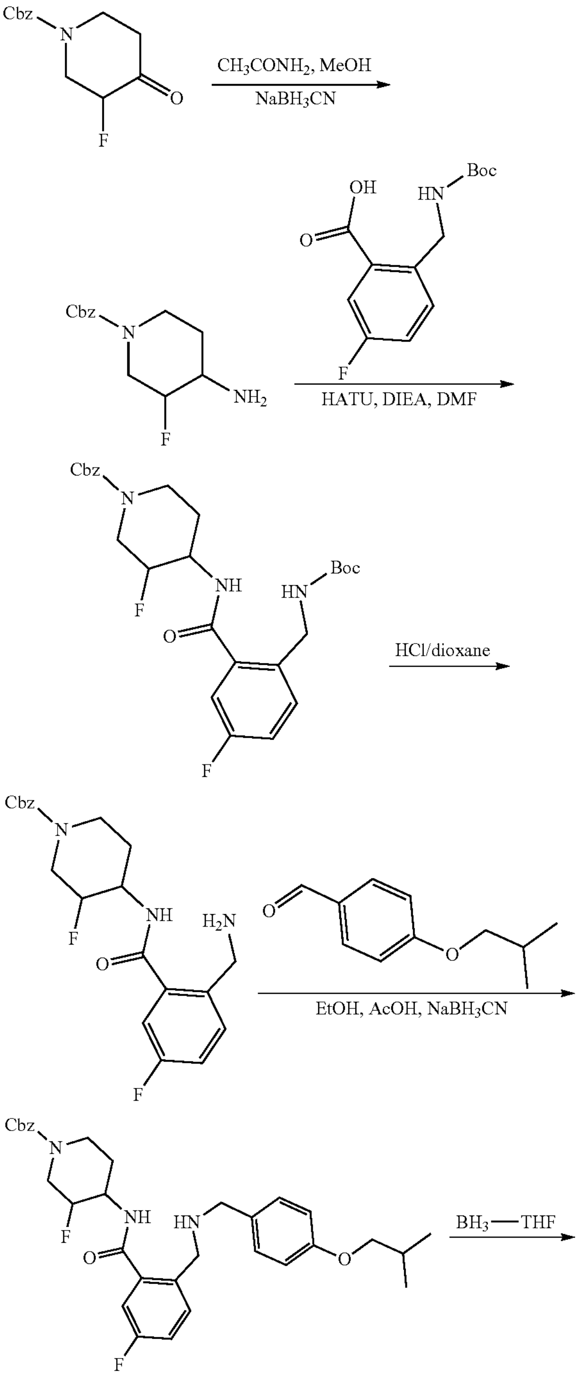

-continued

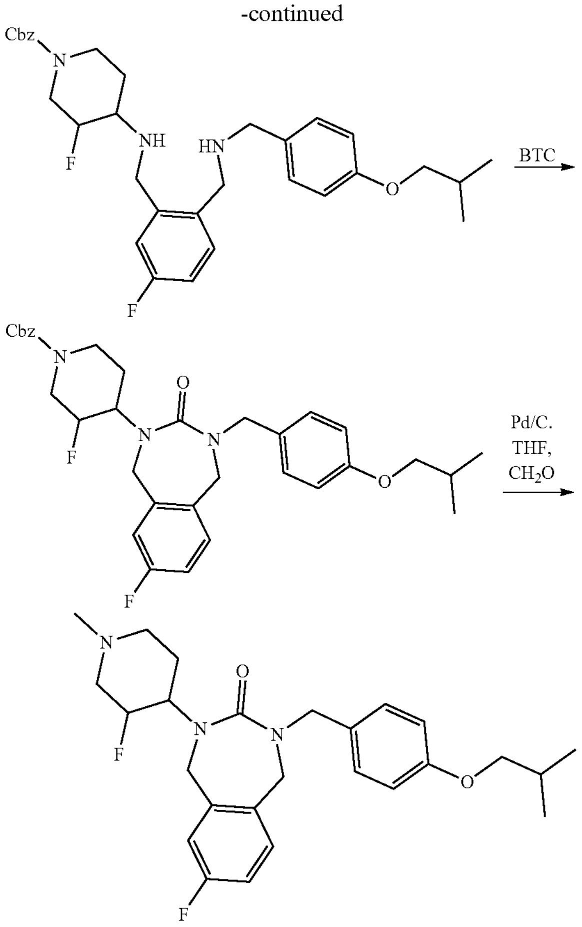

Example 14: Preparation of (3R,4S)-8-fluoro-2-(1-methyl-3-fluoropiperidin-4-yl)-4-[[4-(2-methylpropoxy)phenyl]methyl]-1,5-di hydro-2,4-benzodiazepine-3-one (A19014-0)

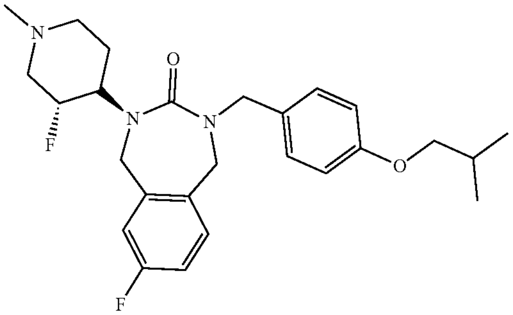

14.1 Preparation of benzyl 4-amino-3-fluoropiperidine-1-carboxylate

Benzyl 3-fluoro-4-oxopiperidine-1-carboxylate (2 g, 7.9 mmol), acetamide (2.35 g, 39.8 mmol), $NaBH_3CN$ (1 g, 15.9 mmol) and methanol (10 mL) were placed in a 25 mL three-necked round-bottom flask, and the mixture was reacted at room temperature overnight with nitrogen purging. After the reaction was completed, the reaction mixture was extracted with EtOAc (3x30 mL). The resulting mixture was washed with brine (2x20 mL), dried over anhydrous $Na_2SO_4$ and filtered, the filtrate was concentrated under reduced pressure, and the residue was purified by silica gel column chromatography (ethyl acetate/petroleum ether=1:1) to give a colorless oil (0.7 g, yield 34.86%).

14.2 Preparation of benzyl 4-[2-[(tert-butoxycarbonyl)amino]methyl]-5-fluorobenzamido]-3-fluoropiperidine-1-carboxylate The preparation was performed with reference to the step 2.3 of the method in Example 2 to give an oil (1.3 g).

14.3 Preparation of benzyl 4-[2-(aminomethyl)-5-fluorobenzamide]-3-fluoropiperidine-1-carboxylate The preparation was performed with reference to the step 1.10 of the method in Example 1 to give a light yellow oil (1 g).

14.4 Preparation of benzyl 3-fluoro-4-[5-fluoro-2-[[4-(2-methylpropoxy)benzyl]methylamino]benzamide-piperidine-1-carboxylate The preparation was performed with reference to the step 2.5 of the method in Example 2 to give a yellow oil (0.6 g, yield 42.8%).

14.5 Preparation of benzyl 3-fluoro-4-[5-fluoro-2-[[4-(2-methylpropoxy)benzyl]methylamino]benzylamino-piperidine-1-carboxylate The preparation was performed with reference to the step 2.6 of the method in Example 2 to give a yellow oil (0.23 g, yield 18.32%).

14.6 Preparation of 8-fluoro-2-(benzyl 3-fluoropiperidine-1-carboxylate)-4-[[4-(2-methylpropoxy)phenyl]methyl]-1,5-dihydro-2,4-benzodiazepine-3-one The preparation was performed with reference to the step 1.9 of the method in Example 1 to give a colorless oil (0.13 g, yield 88.7%).

14.7 Preparation of (3R,4S)-8-fluoro-2-(1-methyl-3-fluoropiperidin-4-yl)-4-[[4-(2-methylpropoxy)phenyl]methyl]-1,5-di hydro-2,4-benzodiazepine-3-one The preparation was performed with reference to the step 3.8 of the method in Example 3 to give a racemate, which was purified by Flash-Prep-HPLC to give a yellow solid (18.1 mg, yield 17.03%). $^1H$ NMR (400 MHz, Methanol-$d_4$) δ 7.23-7.18 (m, 2H), 7.13 (dd, J=9.0, 2.6 Hz, 1H), 7.00 (dd, J=8.4, 5.5 Hz, 1H), 6.93 (td, J=8.6, 2.6 Hz, 1H), 6.88-6.84 (m, 2H), 4.85-4.77 (m, 1H), 4.71 (d, J=5.1 Hz, 1H), 4.59-4.40 (m, 5H), 4.35-4.21 (m, 2H), 3.74 (d, J=6.5 Hz, 2H), 3.26 (dt, J=10.5, 5.3 Hz, 0H), 2.98-2.84 (m, 1H), 2.38 (s, 3H), 2.221.90 (m, 4H), 1.87-1.71 (m, 1H), 1.04 (d, J=6.7 Hz, 6H); LCMS (ES, m/z): 458 $[M+H]^+$.

Example 15: Preparation of (3S,4S)-8-fluoro-2-(1-methyl-3-fluoropiperidin-4-yl)-4-[[4-(2-methylpropoxy)phenyl]methyl]-1,5-dihydro-2,4-benzodiazepine-3-one (A19014-0A)

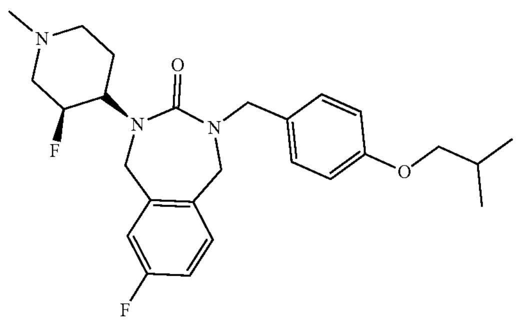

The preparation was performed with reference to the method in Example 14 to give a colorless oil (84 mg, yield 74.25%). $^1$H NMR (400 MHz, Methanol-$d_4$) δ 7.22 (d, J=8.5 Hz, 2H), 7.07 (dd, J=9.1, 2.7 Hz, 1H), 7.01 (dd, J=8.4, 5.5 Hz, 1H), 6.93 (td, J=8.6, 2.7 Hz, 1H), 6.89-6.84 (m, 2H), 4.80-4.19 (m, 8H), 3.74 (d, J=6.5 Hz, 2H), 3.24-3.11 (m, 1H), 3.03 (d, J=11.5 Hz, 1H), 2.49-2.17 (m, 6H), 2.06 (dt, J=13.3, 6.6 Hz, 1H), 1.60 (d, J=12.4 Hz, 1H), 1.09-0.99 (m, 6H); LCMS (ES, m/z): 458 $[M+H]^+$.

Example 16: Preparation of 7,8-difluoro-2-(4-isobutoxybenzyl)-4-(1-methylpiperidin-4-yl)-1,2,4,5-tetrahydro-3H-benzo[e][1,3]diazepin-3-one (A20001)

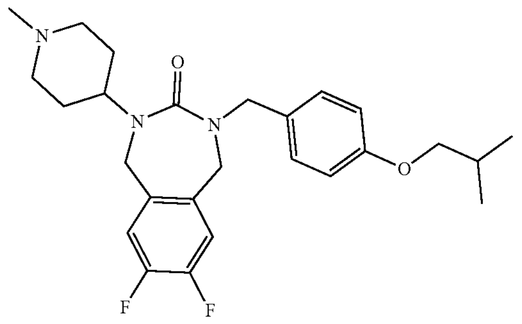 [SMILES: CC(C)COc1ccc(CN2Cc3cc(F)c(F)cc3CN(C3CCN(C)CC3)C2=O)cc1]

The preparation was performed with reference to the method in Example 1 to give a white solid (51.9 mg). $^1$H NMR (400 MHz, Methanol-$d_4$) δ 7.34 (dd, J=10.0, 8.4 Hz, 1H), 7.20 (d, J=8.4 Hz, 2H), 6.92 (dd, J=10.0, 8.4 Hz, 1H), 6.90-6.82 (m, 2H), 4.47 (d, J=14.0 Hz, 4H), 4.36 (s, 2H), 4.40-4.28 (m, 1H), 3.73 (d, J=6.5 Hz, 2H), 3.60 (d, J=12.2 Hz, 2H), 3.21-3.11 (m, 2H), 2.90 (s, 3H), 2.35 (dd, J=13.5, 3.8 Hz, 1H), 2.29 (dd, J=13.1, 3.8 Hz, 1H), 2.05 (hept, J=6.7 Hz, 1H), 1.94 (d, J=13.6 Hz, 2H), 1.04 (d, J=6.7 Hz, 6H). LCMS (ES, m/z): 458 $[M+H]^+$.

Example 17: Preparation of 6-fluoro-N-(1-methylpiperidin-4-yl)-2-[[4-(2-methylpropoxy)phenyl]methyl]-3-oxoimidazo[1,5-a]pyridine-8-carboxamide (A19016)

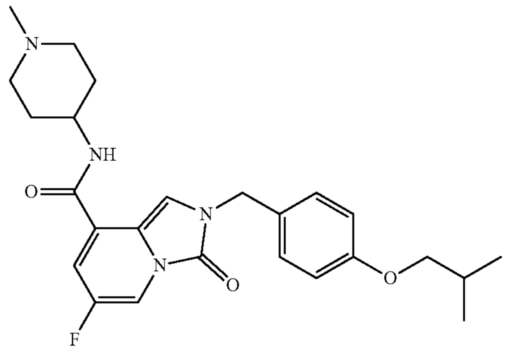 [SMILES: CC(C)COc1ccc(Cn2cc3c(C(=O)NC4CCN(C)CC4)cc(F)cn3c2=O)cc1]

The preparation was performed with reference to the method in Example 14 to give a red solid (308 mg). $^1$HNMR (400 MHz, DMSO-$d_6$) δ 8.33 (d, J=7.7 Hz, 1H), 7.76 (ddd, J=4.1, 1.9, 0.9 Hz, 1H), 7.29-7.17 (m, 2H), 7.10 (dd, J=8.6, 1.9 Hz, 1H), 7.06 (d, J=0.9 Hz, 1H), 6.94-6.83 (m, 2H), 4.91 (s, 2H), 3.72 (d, J=6.5 Hz, 2H), 3.69-3.56 (m, 1H), 2.78-2.71 (m, 2H), 2.15 (s, 3H), 2.06-1.86 (m, 3H), 1.73 (d, J=12.5 Hz, 2H), 1.51 (qt, J=12.0, 6.0 Hz, 2H), 0.96 (d, J=6.7 Hz, 6H). LCMS (ES, m/z): 455 $[M+H]^+$.

Example 18: Preparation of 7-fluoro-2-[[4-(2-hydroxy-2-methylpropyl)phenyl]methyl]-4-(1-methylpiperidin-4-yl)-1,5-dihydro-2,4-benzodiazepin-3-one (A19010)

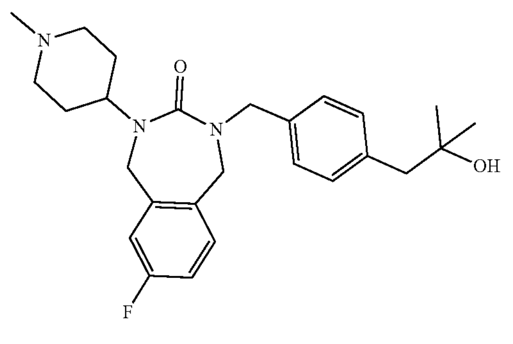 [SMILES: CN1CCC(N2Cc3cc(F)ccc3CN(Cc3ccc(CC(C)(C)O)cc3)C2=O)CC1]

Synthetic Route:
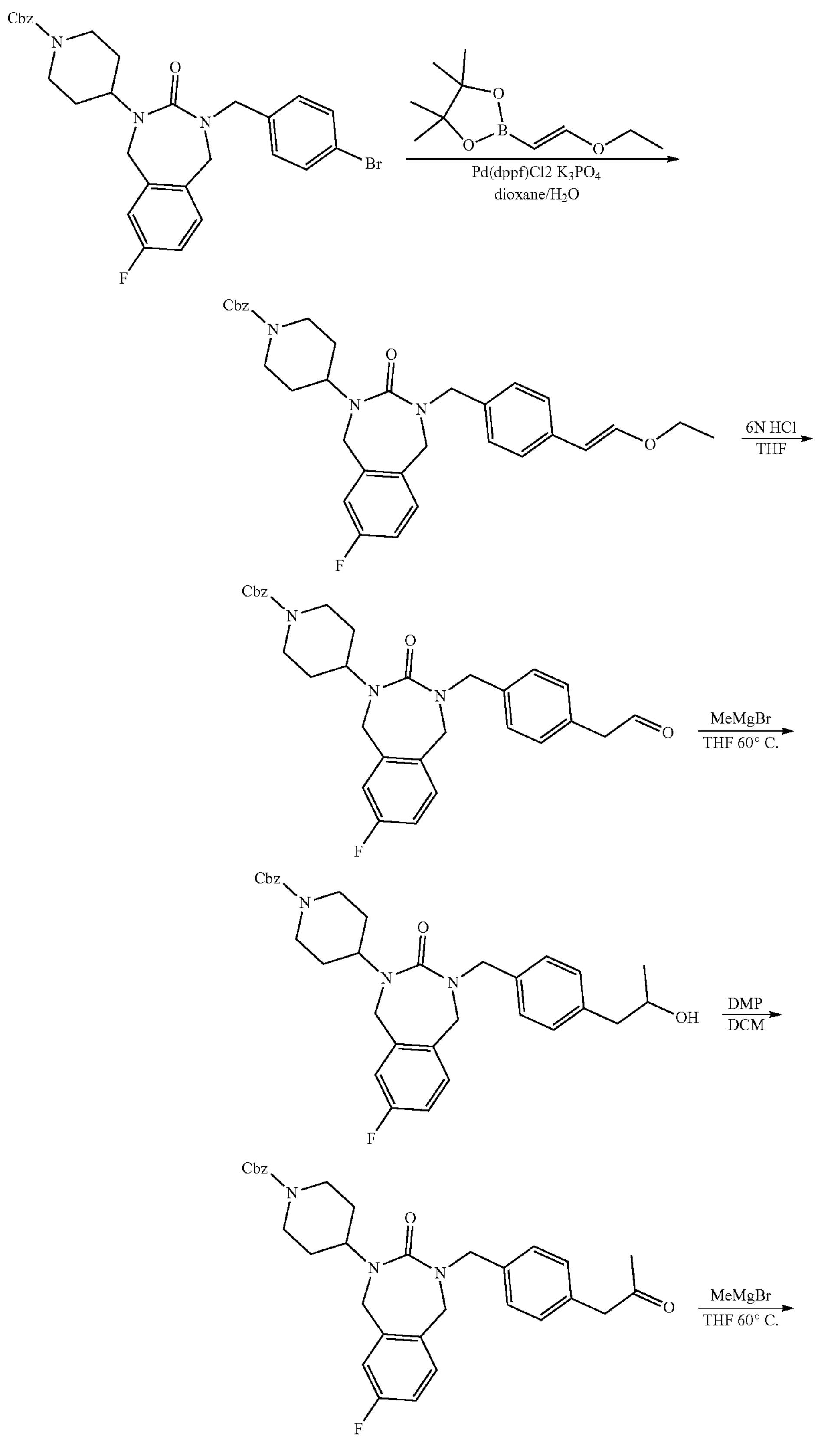

-continued

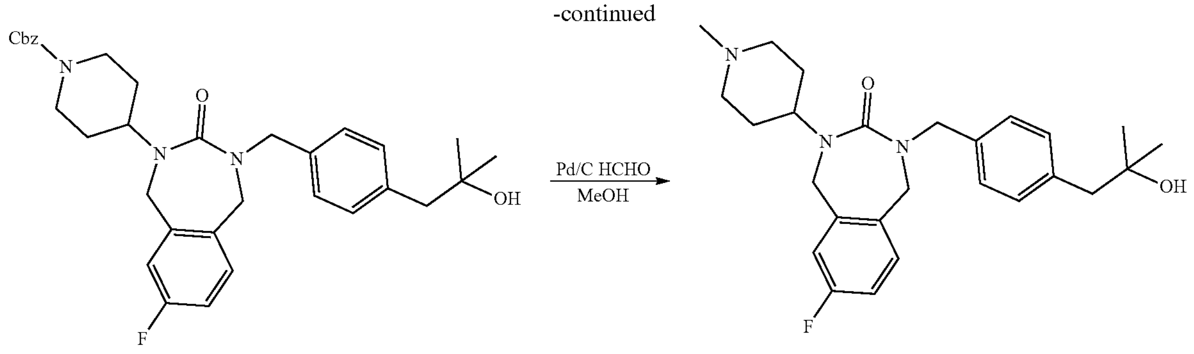

18.1 Preparation of benzyl 4-[4-[(4-bromophenyl) methyl]-8-fluoro-3-oxo-1,5-dihydro-2,4-benzodiazepin-2-yl]piperidine-1-carboxylate The preparation was performed with reference to the method in Example 4 to give a light yellow oil (1 g).

18.2 Preparation of benzyl-4-[4-([4-[(E)-2-ethoxyvinyl]phenyl]methyl)-8-fluoro-3-oxo-1,5-dihydro-2,4-benzodiazepin-2-yl]piperidine-1-carboxylate Benzyl-4-[4-[(4-bromophenyl)methyl]-8-fluoro-3-oxo-1,5-dihydro-2,4-benzodiazepin-2-yl]piperidine-1-carboxylate (1.00 g, 1.765 mmol), (E)-2-(2-ethoxyvinyl)-4,4,5,5-tetramethyl-1,3,2-dioxaborane (0.70 g, 3.531 mmol), dioxane (10.00 mL), water (2.00 mg) and $K_3PO_4$ (1.12 g, 5.296 mmol) were added into a 100 mL three-necked flask respectively, and the resulted solution was stirred at 25° C. for 10 min, added with Pd(dppf)$Cl_2$ (0.14 g, 0.177 mmol), warmed up to 100° C. and reacted for 2 h.

After the reaction was completed, the reaction mixture was added with water to quench the reaction, and extracted with ethyl acetate (3×20 mL). The organic phase was washed with 1 N hydrochloric acid solution (2×20 mL) and saturated brine (2×20 mL) sequentially, dried over anhydrous sodium sulfate, evaporated to remove the solvent under pressure, and purified by column chromatography (EA:PE=1:30) to give the compound benzyl-4-[4-([4-[(E)-2-ethoxyvinyl]phenyl]methyl)-8-fluoro-3-oxo-1,5-dihydro-2,4-benzodiazepin-2-yl]piperidine-1-carboxylate (400 mg, yield 40.63%) as a brown oil.

18.3 Preparation of benzyl 4-(8-fluoro-3-oxo-4-[[4-(2-oxoethyl)phenyl]methyl]-1,5-dihydro-2,4-benzodiazepin-2-yl)piperidine-1-carboxylate Benzyl-4-[4-([4-[(E)-2-ethoxyvinyl]phenyl]methyl)-8-fluoro-3-oxo-1,5-dihydro-2,4-benzodiazepin-2-yl]piperidine-1-carboxylate (200.00 mg, 0.359 mmol), tetrahydrofuran (2.00 mL) and HCl (6 M) (2.00 mL) were added into a 50 mL three-necked flask, and the mixture was stirred at 25° C. for 2 h.

After the reaction was completed, the reaction mixture was added with water to quench the reaction, extracted with methyl tert-butyl ether (3×10 mL). The organic phase was washed with saturated brine (30 mL), dried over anhydrous sodium sulfate, and evaporated under reduced pressure to remove the solvent to give the compound benzyl 4-(8-fluoro-3-oxo-4-[[4-(2-oxoethyl)phenyl]methyl]-1,5-dihydro-2,4-benzodiazepin-2-yl)piperidine-1-carboxylate (200 mg, yield 105.30%) as a yellow oil.

18.4 Preparation of benzyl-4-(8-fluoro-4-[[4-(2-hydroxypropyl)phenyl]methyl]-3-oxo-1,5-dihydro-2,4-benzodiazepin-2-yl)piperidine-1-carboxylate Benzyl 4-(8-fluoro-3-oxo-4-[[4-(2-oxoethyl)phenyl]methyl]-1,5-dihydro-2,4-benzodiazepin-2-yl)piperidine-1-carboxylate (200.00 mg, 0.378 mmol) and tetrahydrofuran (3.00 mL) were added into a 50 mL three-necked flask, and the mixture was cooled to 0° C., stirred for 5 min, added with magnesium(methyl)bromide (180.12 mg, 1.511 mmol), warmed up to 60° C. and stirred for 2 h. After the reaction was completed, the reaction mixture was added with $NH_4Cl$ solution to quench the reaction, and extracted with ethyl acetate (3×20 mL). The organic phase was washed with saturated brine (20 mL), dried over anhydrous sodium sulfate, and evaporated under reduced pressure to remove the solvent to give the compound benzyl-4-(8-fluoro-4-[[4-(2-hydroxypropyl)phenyl]methyl]-3-oxo-1,5-dihydro-2,4-benzodiazepine-2-yl)piperidine-1-carboxylate (200 mg, yield 97.06%) as a yellow oil.

18.5 Preparation of benzyl-4-(8-fluoro-3-oxo-4-[[4-(2-oxopropyl)phenyl]methyl]-1,5-dihydro-2,4-benzodiazepin-2-yl)piperidine-1-carboxylate Benzyl-4-(8-fluoro-4-[[4-(2-hydroxypropyl)phenyl]methyl]-3-oxo-1,5-dihydro-2,4-benzodiazepin-2-yl)piperidine-1-carboxylate (200.00 mg, 0.367 mmol) and dichloromethane (20.00 mL) were added into a 50 mL three-necked flask, and the mixture was cooled to 0° C., stirred for 5 min under nitrogen atmosphere, added with DMP (310.92 mg, 0.733 mmol) and stirred at 25° C. for 3 h. After the reaction was completed, the reaction mixture was added with $NaHCO_3$ solution to quench the reaction and extracted with dichloromethane (3×20 mL). The organic phase was washed with saturated brine, dried over anhydrous sodium sulfate, and evaporated under reduced pressure to remove the solvent to give the compound benzyl-4-(8-fluoro-3-oxo-4-[[4-(2-oxopropyl)phenyl]methyl]-1,5-dihydro-2,4-benzodiazepine-2-yl)piperidine-1-carboxylate (180 mg, yield 90.33%) as a yellow oil.

18.6 Preparation of benzyl-4-(8-fluoro-4-[[4-(2-hydroxy-2-methylpropyl)phenyl]methyl]-3-oxo-1,5-dihydro-2,4-benzodiazepin-2-yl)piperidine-1-carboxylate Benzyl-4-(8-fluoro-3-oxo-4-[[4-(2-oxopropyl)phenyl]methyl]-1,5-dihydro-2,4-benzodiazepin-2-yl)piperidine-1-carboxylate (150.00 mg, 0.276 mmol), tetrahydrofuran (5.00 mL, 0.069 mmol) and MeMgBr (2.00 mL, 0.017 mmol)

were added into a 50 mL three-necked flask, and the mixture was warmed up to 60° C. and reacted for 3 h under nitrogen atmosphere. After the reaction was completed, the reaction mixture was added with $NH_4Cl$ solution to quench the reaction, and extracted with ethyl acetate (3×10 mL). The organic phase was washed with saturated brine (10 mL), dried over anhydrous sodium sulfate, and evaporated under reduced pressure to remove the solvent to give the compound benzyl-4-(8-fluoro-4-[[4-(2-hydroxy-2-methylpropyl)phenyl]methyl]-3-oxo-1,5-dihydro-2,4-benzodi azepine-2-yl)piperidine-1-carboxylate (140 mg, yield 90.66%) as a yellow oil.

18.7 Preparation of 7-fluoro-2-[[4-(2-hydroxy-2-methylpropyl)phenyl]methyl]-4-(1-methylpiperidin-4-yl)-1,5-dihydro-2,4-benzodiazepin-3-one Benzyl 4-(8-fluoro-4-[[4-(2-hydroxy-2-methylpropyl) phenyl]methyl]-3-oxo-1,5-dihydro-2,4-benzodiazepine -2-yl)piperidine-1-carboxylate (150.00 mg, 0.268 mmol), methanol (10.00 mL, 246.989 mmol), formaldehyde (2.00 mL, 0.067 mmol) and $Pd(OH)_2/C$ (20.00 mg, 0.142 mmol) were added into a 100 mL three-necked flask, and the mixture was purged with hydrogen, and stirred at 25° C. for 5 h. The reaction mixture was added with water to quench the reaction, and extracted with ethyl acetate (3×10 mL). The organic phase was washed with saturated brine (10 mL), dried over anhydrous sodium sulfate, and evaporated under reduced pressure to remove the solvent, and the residue was purified by column chromatography (DCM:MeOH=30:1) to give the compound 7-fluoro-2-[[4-(2-hydroxy-2-methylpropyl)phenyl]methyl]-4-(1-methylpiperidin-4-yl)-1,5-dihydro-2,4-benzodiazepine-3-one (45 mg, yield 38.19%) as a yellow oil. $^1H$ NMR (400 MHz, Methanol-$d_4$) δ 8.48 (s, 1H, FA), 7.10-6.98 (m, 4H), 6.93 (td, J=8.6, 2.7 Hz, 1H), 6.58 (d, 2H), 4.42 (s, 4H), 4.36 (s, 2H), 4.30-4.18 (m, 1H), 3.46-3.39 (m, 2H), 2.96-2.83 (m, 4H), 2.77 (s, 3H), 2.25-2.05 (m, 2H), 1.96-1.84 (m, 3H), 1.36-1.30 (m, 1H), 0.99 (d, J=6.6 Hz, 6H). LCMS (ES, m/z): 400 $[M+H]^+$.

Example 19: Preparation of 4-[(4-cyclopropoxyphenyl)methyl]-7-fluoro-2-(1-methylpiperidin-4-yl)-1,5-dihydro-2,4-benzodiaze pine-3-one (A19022)

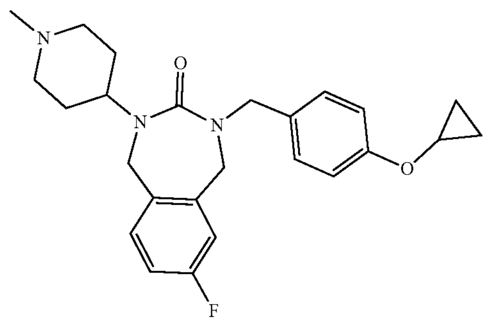 [SMILES: CN1CCC(N2Cc3ccc(F)cc3CN(Cc3ccc(OC4CC4)cc3)C2=O)CC1]

The preparation was performed with reference to the method in Example 2 to give a white solid (9.5 mg). $^1H$-NMR (400 MHz, Chloroform-d): δ 7.25 (d, J=8.5 Hz, 2H), 7.15 (t, J=7.0 Hz, 1H), 7.04-6.97 (m, 2H), 6.90 (td, J=8.4, 2.6 Hz, 1H), 6.65 (dd, J=9.1, 2.6 Hz, 1H), 4.45 (s, 2H), 4.40 (s, 2H), 4.25 (s, 3H), 3.74 (p, J=4.5 Hz, 1H), 3.03 (s, 2H), 2.42-2.38 (m, 3H), 2.22 (s, 2H), 1.99 (s, 2H), 1.73 (d, J=12.5 Hz, 2H), 0.78 (d, J=4.5 Hz, 4H). LCMS (ES, m/z): $424[M+1]^+$.

Pharmacological Examples

Example 20: In Vitro Receptor Binding Assay

Experimental Procedures

1. Formulation of Solutions Required for Experiment

A: (for the preparation of $5\text{-}HT_{2C}$ receptor membrane): 50 mM Tris-HCl buffer: 96.8 g of Tris was weighed and dissolved in double distilled water to reach a total volume of 4000 mL, and the solution was adjusted to pH 7.5 with HCl and diluted to 16000 mL with the pH of 7.4.

B: (for the preparation of $5\text{-}HT_{2A}$ receptor membrane): 11.7 mg of EDTA and 380.84 mg of $MgCl_2$ were weighed and added with 50 mM Tris-HCl buffer to reach a total volume of 400 mL, and the solution was adjusted to pH 7.4 to make final concentrations of 0.1 mM for EDTA and 10 mM for $MgCl_2$.

C: (for the preparation of Dopamine receptor membrane): 2.978 g of HEPES, 1.17 g of NaCl, 0.119 g of $MgCl_2$ and 36.5 mg of EDTA were weighed and added with pure water to reach a total volume of 250 mL, and the solution was adjusted to pH 7.4 to make final concentrations of 50 mM for HEPES, 50 mM for NaCl, 5 mM for $MgCl_2$, and 0.5 mM for EDTA, with the pH of 7.4.

2. Preparation of Receptor Membranes

1) Preparation of CHO-$5\text{-}HT_{2A}$ Receptor Membrane

CHO-$5\text{-}HT_{2A}$ cells were taken out of a refrigerator at −80° C., thawed spontaneously and centrifuged at 2000 g for 15 min at 4° C. The precipitate was collected, and the supernatant was discarded. The solution B was added into the precipitate. The cells were vortexed for 20-30 s for mixing well with the solution B, and the mixture was centrifuged at 50000 g for 25 min at 4° C. The supernatant was carefully discarded, and the solution B was added into the precipitate again. The cells were mixed well with the solution, and the mixture was centrifuged at 50000 g for 25 min at 4° C. The precipitate obtained was stored at −80° C.

2) Preparation of $5\text{-}HT_{2C}$ Membrane

The rat cortex was taken out of a refrigerator at −80° C. and thawed spontaneously. The solution A was added, and the mixture was homogenized for 3-4 s at 4th gear for a total of 4 times and centrifuged at 50000 g for 25 min at 4° C. The supernatant was discarded, and the solution A was added into the precipitate. The mixture was mixed well using a vortex mixer and centrifuged at 50000 g for 25 min at 4° C. (repeated twice). The supernatant was discarded after the centrifugation, and the precipitate was stored at −80° C. for later use.

3) Preparation of CHO-$D_2$ Receptor Membrane

CHO-$D_2$ cells were taken out of a refrigerator at −80° C., thawed spontaneously and centrifuged at 2000 g for 15 min. The homogenate C was added into the precipitate, and the mixture was mixed well using a vortex mixer and centrifuged at 50000 g for 25 min at 4° C. The supernatant was discarded, and the buffer solution C was added into the precipitate for washing and resuspending. The mixture was centrifuged. The supernatant was discarded after the centrifugation, and the precipitate was stored at −80° C. for later use.

3. Competitive Receptor Binding Assay

1) Competitive 5-$HT_{2A}$ Receptor Binding Assay

Step 1: the prepared membrane was suspended in the homogenate B to obtain a 10 mg/mL membrane suspension for later use.

Step 2: 100 μL of the membrane preparation was added into each reaction tube.

Step 3: 100 μL of the solution B was added into a total binding tube (TB), 100 μL of Methysergide (final concentration: $1.0\times10^{-5}$ M) was added into a non-specific binding tube (NB), and 100 μL of test compound was added into each compound binding tube (CB).

Step 4: 10 μL of radioligand $^3$H-Ketanserin was added into each reaction tube to reach a final concentration of 2.98 nM.

Step 5: each reaction tube was incubated at 37° C. for 25 min. After the reaction was completed, the binding ligands were rapidly filtered under reduced pressure, wherein the Whatman test paper GF/C plate was soaked in 0.5% PEI for more than 1 h in advance. After the filtration, the filter membrane was dried at 60° C. and added into a scintillation disc attached with a bottom membrane, which was then added with 40 μL of scintillation liquid, sealed with a top membrane, and left to stand.

Step 6: the scintillation disc was put into a liquid scintillation counter for counting.

2) Competitive 5-$HT_{2C}$ Receptor Binding Assay

Step 1: the prepared membrane was suspended in the homogenate B to obtain a 210 mg/mL membrane suspension for later use.

Step 2: 100 μL of the membrane suspension was added into each reaction tube.

Step 3: 100 μL of the solution B was added into a total binding tube (TB), 100 μL of Ketanserin (final concentration: $1.0\times10^{-5}$ M) was added into a non-specific binding tube (NB), and 100 μL of test compound was added into each compound binding tube (CB).

Step 4: 10 μL of radioligand $^3$H-Mesulergine was added into each reaction tube to reach a final concentration of 3 nM.

Step 5: each reaction tube was incubated at 37° C. for 25 min. After the reaction was completed, the binding ligands were rapidly filtered under reduced pressure, wherein the Whatman test paper GF/C was washed with 0.5% PEI solution 1 h in advance. The filter membrane was fully washed with cold Tris buffer solution, taken out and put into a 4 mL scintillation disc, which was then added with 1 mL toluene scintillation solution and shaken for mixing well.

Step 6: the scintillation disc was put into a liquid scintillation counter for counting.

3) Competitive CHO-$D_2$ Receptor Binding Assay

Step 1: the prepared membrane was suspended in the homogenate C to obtain 8 mg/mL membrane suspension for later use.

Step 2: 100 μL of the membrane suspension was added into each reaction tube.

Step 3: 100 μL of the solution C was added into a total binding tube (TB), 100 μL of Haloperidol (final concentration: $1.0\times10^{-5}$ M) was added into a non-specific binding tube (NB), and 100 μL of test compound was added into each compound binding tube (CB).

Step 4: 10 μL of radioligand $^3$H-Spiperone was added into each reaction tube to reach a final concentration of 1.176 nM.

Step 5: each reaction tube was incubated at 37° C. for 25 min. After the reaction was completed, the binding ligands were rapidly filtered under reduced pressure, wherein the Whatman test paper GF/B plate was soaked in 0.5% PEI for more than 1 h in advance. After the filtration, the filter membrane was dried at 60° C. and added into a scintillation disc attached with a bottom membrane, which was then added with 40 μL of scintillation liquid, sealed with a top membrane, and left to stand.

Step 6: the filter plate was put into a liquid scintillation counter for counting.

4. Experimental Results

The Ki values of pimavanserin for 5-$HT_{2A}$ and 5-$HT_{2C}$ receptors were 0.036 nM and 2.94 nM, respectively, and the Ki values of the compound NH-K-A19016-OA for 5-$HT_{2A}$ and 5-$HT_{2C}$ receptors were 0.002 nM and 26.1 nM, respectively, which were superior to those of pimavanserin; the Ki values of the compound NH-K-A19001 for 5-$HT_{2A}$ and 5-$HT_{2C}$ receptors were 0.028 nM and 2.4 nM, respectively, which were superior to those of pimavanserin; the Ki values of the compound NH-K-A19005 for 5-$HT_{2A}$ and 5-$HT_{2C}$ receptors were 0.429 nM and 3.39 nM, respectively, which were at the same level as those of pimavanserin. The detailed results are shown in the table below.

TABLE 1

| Compound | 5-$HT_{2A}$ (Ki value, nM) | 5-$HT_{2C}$ (Ki value, nM) | 2C/2A |
|---|---|---|---|
| NH-K-A19001 | 0.028 | 2.4 | 86.327 |
| NH-K-A19005 | 0.429 | 3.39 | 7.907 |
| NH-K-A19006 | 0.277 | 1.621 | 5.856 |
| NH-K-A19007 | 2.721 | 27.32 | 10.040 |
| NH-K-A19008 | 5.294 | 42.35 | 7.999 |
| NH-K-A19009 | 2.994 | 2.03 | 0.679 |
| NH-K-A19011 | 12.699 | — | — |
| NH-K-A19012 | 0.947 | 9.363 | 9.882 |
| NH-K-A19013 | 9.775 | — | — |
| NH-K-A19014-0 | 4.187 | 0.20 | 0.049 |
| NH-K-A19015 | 1.690 | 0.41 | 0.241 |
| NH-K-A190017 | 1.626 | 485.8 | 298.694 |
| NH-K-A19019 | 53.312 | — | — |
| NH-K-A19020 | 1.740 | — | — |
| NH-K-A19014-0A | 0.002 | 26.10 | 16029.47 |
| NH-K-A20001 | 5.98 | — | — |
| NH-K-A19010 | 20.05 | 18.23 | 0.91 |
| NH-K-A19022 | 0.15 | 1.33 | 8.76 |
| Pimavanserin | 0.036 | 2.94 | 81.667 |

Example 21: In Vitro hERG Assay

1. Formulation of Compounds a. The stock solutions of the test compounds were diluted with DMSO to obtain 0.3 mM, 1 mM, and 3 mM dilutions sequentially.

b. The stock solutions of the test compounds were diluted in an extracellular fluid to obtain working solutions of the test compounds at concentrations of 0.3 μM, 1 μM, 3 μM, 10 μM and 30 μM. The working solutions of the test compounds were ultrasonically treated for 20 min.

c. 10 mg of cisapride (system positive compound) was formulated with 2002.42 μL of dimethyl sulfoxide (DMSO) to obtain a stock solution at 10.113 mM.

d. The cisapride stock solution was diluted with dimethyl sulfoxide (DMSO) to 1 μM, 10 μM, 100 μM and 1 mM sequentially.

e. 10 μL of the diluted solution at each concentration was added into 10 mL of the extracellular fluid to ensure that the concentration of DMSO is 0.1%.

f. The final concentrations of the working solution of cisapride were 1 nM, 10 nM, 100 nM and 1000 nM, respectively.

g. No visible precipitates were observed in the working solutions at all concentrations by the naked eye.

2. Cell Line Information

In this assay, the HEK-293 cell line stably expressing the hERG potassium channel was used for experimental detection.

The HEK-293 cell line stably expressing the hERG potassium channel were cultured in DMEM medium containing 10% fetal bovine serum and 0.8 mg/mL G418 at 37° C. and a concentration of carbon dioxide of 5%.

Cell passage: the old medium was removed, and the cells were washed once with PBS, added with 0.5 mL TrypLE™ Express solution and incubated at 37° C. for 1 min. When the cells were detached from the bottom of the dish, 3 mL of complete medium preheated at 37° C. was added. The cell suspension was gently pipetted to separate the aggregated cells. The cell suspension was transferred to a sterile centrifuge tube and centrifuged at 300 G for 5 min to collect the cells. The cells were seeded in 6 cm cell culture dishes at a density of $1\times10^5$ cells/dish (final volume: 5 mL) for expansion or maintenance culture.

For patch clamping, $5\times10^3$ cells were plated on a coverslip, and cultured in a 24-well plate (final volume: 500 μL) for 18 h before the experimental detection.

In order to maintain the electrophysiological activity of the cells, the cell density must not exceed 80%.

3. Patch Clamping

Under an inverted microscope, recording electrodes were controlled by a glass electrode micromanipulator (micromanipulation) to contact with the cell. A negative voltage was applied to promote to form a GΩ seal among cells. After forming the GΩ seal, a rapid capacitance compensation was given. Under the continuous negative voltage, the cell membrane was ruptured to perform a whole-cell recording. In the whole-cell recording, a slow capacitance compensation was given, and the values of membrane capacitance and series resistance were recorded.

The FIGURE shows the voltage stimulation scheme for cellular hERG potassium current: the cell membrane clamping voltage was −80 mV; the voltage was first elevated from −80 mV to +30 mV, held for 2.5 s, and rapidly adjusted to and held at −50 mV for 4 s, thus exciting the tail current of the hERG channel. Data were acquired every 10 s. −50 mV was used for leakage current detection.

The coverslip planted with cells was placed in the recording chamber of the inverted microscope. Negative control and test compounds flowed through the recording chamber in an ascending order of concentration by gravity perfusion to quickly act on the cells. During the recording, the extracellular fluid was continuously circulated by a vacuum pump. The current detected in a cell in the negative control was used as the control group for the cell per se. Each concentration was allowed to act for 5 min or until the current was stabilized. All experiments were performed at room temperature.

4. Data analysis

The current for each concentration was first normalized according to $$\left(\frac{\text{Tail current of compound}}{\text{Tail current of blank control}}\right),$$

and then the corresponding inhibition rate was calculated according to $$\left(1-\frac{\text{Tail current of compound}}{\text{Tail current of blank control}}\right),$$

Basic statistics were calculated for each concentration, including mean, standard deviation (SD), standard error (SE), and replicates (n). The dose-dependent curve was fitted with the following equation and the half maximal inhibitory concentration ($IC_{50}$) of the test compounds was calculated:

$$\text{Inhibition}=\frac{1}{1+\left(\frac{IC50}{C}\right)^h}$$

wherein C represents the test compound concentration, $IC_{50}$ represents the half maximal inhibitory concentration, and h represents the Hill coefficient. Curve fitting and calculation of $IC_{50}$ were performed by GraphPad Prism 5.0 software.

5. Experimental Results

In the hERG experiment, the $IC_{50}$ value of pimavanserin was 208 nM, and the ICso values of NH-K-A19001, NH-K-A19005 and NH-K-A19006 were 206 nM, 3173 nM and 1194 nM, respectively. These three compounds have less cardiotoxicity than pimavanserin, suggesting that the compounds of the present invention have lower cardiotoxicity as compared to pimavanserin. The results are shown in the table below.

TABLE 2

| Compound | hERG(nM) |
|---|---|
| NH-K-A19001 | 260 |
| NH-K-A19005 | 3173 |
| NH-K-A19006 | 1194 |
| Pimavanserin | 208 |

Example 22: Animal experiments

1. Test Method 1.1 Effect on MPTP+MK-801-induced Parkinson's disease mouse model (anti-PDP efficacy model)

Animals were injected with different doses of MPTP(1-methyl-4-phenyl-1,2,3,6-tetrahydropyridine) intraperitoneally every morning for 5 consecutive days. On day 5, the mice were injected with pimavanserin or NS intraperitoneally after an interval of 1.5 h following the injection of MPTP in the morning, then injected with dizocilpine(MK-801) at 0.3 mg/kg (or NS) intraperitoneally after an interval of 0.5 h. Then, after an interval of 0.25 h, the mice were placed into an autonomous activity test box (a black polyethylene box with the specification of 29 cm×29 cm×30 cm) for video recording for 20 min. Video analysis was performed after the video recording to evaluate the activity of the mice.

1.2 Effect on MPTP+APO-induced climbing behavior in male mice (DA motor deterioration model) Animals were injected with different doses of MPTP intraperitoneally every morning for 5 consecutive days. On day 5, the mice were injected with pimavanserin, clozapine, quetiapine or NS intraperitoneally after an interval of 1.5 h following the injection of MPTP in the morning, then injected with apomorphine(APO) at 1 mg/kg with an administration volume of 0.1 mL/10 g body weight subcutaneously after an interval of 0.5 h. After the subcutaneous injection, animals were immediately placed into a climbing cage (self-made, a cylindrical cage with the diameter of 13 cm and the height of 15 cm, made of a stainless steel wire mesh with the diameter of about 0.1 cm, the bottom of which is a semi-transparent polyethylene plate, and the cage cover of which is a stainless steel cage cover), and the behaviors of animals at minutes 10-11, 20-21 and 30-31 after the APO injection was observed and scored.

Scoring criteria: four feet on the floor scored 0; two forepaws on the cage scored 1; and four feet on the cage scored 2.

1.3 Investigation of Sedation Side Effects (Anti-Sedation Model)

Qualified SPF grade C57BL/6j mice were taken and randomly divided into 13 groups of 8 mice each: blank group, pimavanserin group, NH-K-A19001 group, NH-K-A19005 group and NH-K-A19006 group. According to different doses of each group, solutions at different concentrations were separately formulated for intraperitoneal injection, with the final administration volume of 10 mL/kg.

All groups were tested for autonomic activities 45 min after the administration of pimavanserin and other compounds. The movement at 0-20 min was recorded on video, and the movement distance in 20 min was analyzed by Top Scan 3.00 software. The inhibition rate of each group relative to the blank group after the administration were calculated, and the sedation effects of the compounds were comprehensively evaluated in combination with a statistical conclusion.

1.4 Test Results

The experiment showed that the $ED_{50}$ values of pimavanserin for the PDP efficacy, the sedation and the motor deterioration were 0.37 mg/kg, 6.79 mg/kg and >30 mg/kg, respectively, with a sedation/PDP efficacy ratio of 18.35 and a motor deterioration/PDP efficacy ratio >81.08; and the $ED_{50}$ values of NH-K-A19001 for the PDP efficacy and the sedation were 0.33 mg/kg and 3.74 mg/kg, respectively, with a sedation/PDP efficacy ratio of 11.33. The $ED_{50}$ values of NH-K-A19005 for the PDP efficacy and the sedation were 1.85 mg/kg and 19.98 mg/kg, respectively, with a sedation/PDP efficacy ratio of 10.8. The $ED_{50}$ values of NH-K-A19006 for the PDP efficacy and the sedation were 0.31 mg/kg and 11.9 mg/kg, respectively, with a sedation/PDP efficacy ratio of 38.39. It can be known that the $ED_{50}$ values of NH-K-A19001 and NH-K-A19006 for the PDP efficacy are comparable to those of pimavanserin, and the safety window of NH-K-A19006 is larger than that of pimavanserin. The $ED_{50}$ of the NH-K-A19005 for the PDP efficacy is slightly higher than that of pimavanserin. In addition, the compounds of the present invention (e.g., NH-K-A19001, NH-K-A19005 and NH-K-A190016) do not have DA mechanism of action and no motor deterioration is observed.

TABLE 3

| | PDP efficacy (high activity mg/kg) | Sedation side effects (sedation mg/kg) | DA side effects (climbing motor deterioration mg/kg) | Ration (Sedation/ PDP) | Ration (DA/ PDP) |
|---|---|---|---|---|---|
| Pimavanserin | 0.37 | 6.79 | >30 | 18.35 | >81.08 |
| NH-K-A19001 | 0.33 | 3.74 | — | 11.33 | — |
| NH-K-A19005 | 1.85 | 19.98 | — | 10.8 | — |
| NH-K-A19006 | 0.31 | 11.9 | — | 38.39 | — |

Example 23: In Vitro and In Vivo Experimental Method and Data of A01 Series of Compounds of the Pimavanserin Project 1. Head Thrust Test in Mice 1.1 Test Method Mice were stratified according to body weight and then randomly divided into a model control group, a blank control group and drug administration groups. 1 h after the intragastric administration of a vehicle or a drug, the animals were placed in a beaker (with the diameter of 13 cm and the height of 19 cm) paved with fresh padding, and were injected with a modeling drug DOI ((±)-1-(2,5-dimethoxy-4-iodophenyl)-2-aminopropane hydrochloride or (±)-2,5-dimethoxy-4-iodoamphetamine hydrochloride) intraperitoneally at a dose of 1 mg/kg. The head shaking times of the mice during the 0-20 min after the intraperitoneal injection of DOI were recorded. The head shaking behavior is defined as a rapid rotational twitching or wet dog-like shaking of the mouse head, which is distinguished from normal grooming or exploring behavior.

1.2 Test Data

The test results showed that $ED_{50}$ value of pimavanserin for inhibiting DOI-induced head shaking behavior of mice was 0.39 mg/kg, and the $ED_{50}$ values of NH-K-A19001, NH-K-A19005, NH-K-A19006 and NH-K-A19012 for inhibiting DOI-induced head shaking behavior of mice were 0.06 mg/kg, 0.15 mg/kg, 0.012 mg/kg and 0.30 mg/kg, respectively, suggesting that the compounds of the present invention have better anti-psychiatric disease effect and better drug efficacy. The detailed results are shown in the table below.

TABLE 4

$ED_{50}$ of compounds such as pimavanserin for inhibiting the DOI-induced head shaking behavior

| Compound | $ED_{50}$ (mg/kg) |
|---|---|
| Pimavanserin | 0.39 |
| NH-K-A19001 | 0.06 |
| NH-K-A19005 | 0.15 |
| NH-K-A19006 | 0.012 |
| NH-K-A19012 | 0.30 |

Note: $ED_{50}$ represents the median effective dose.

2. Dizocilpine (MK-801)-Induced High Activity Test in Mice 2.1 Test Method

Mice were stratified according to body weight and then randomly divided into a model control group, a blank control group and drug administration groups. After the administration of a test substance (or a control substance), the mice were placed into an autonomous activity test box (a black polyethylene box with the specification of 29 cm×29 cm×30 cm) for adaptation, and injected with MK-801 at 0.3 mg/kg intraperitoneally 1 h after the intragastric administration. The mice were then placed into the autonomous activity test box for video recording for 60 min. Video analysis was performed after the video recording to evaluate the activity of the mice.

2.2 Test Results

The test results showed that the $ED_{50}$ value of pimavanserin for inhibiting MK-801-induced high activity behavior of mice was 3.288 mg/kg, and the $ED_{50}$ values of NH-K-A19005, NH-K-A19006 and NH-K-A19012 for inhibiting MK-801-induced high activity behavior of mice were 1.01 mg/kg, 0.2648 mg/kg and 3.728 mg/kg, respectively, suggesting that the compounds of the present invention have better anti-psychiatric disease effect and better drug efficacy. The detailed results are shown in the table below.

TABLE 5

$ED_{50}$ of compounds such as pimavanserin for inhibiting the MK-801-induced high activity behavior

| Compound | $ED_{50}$ (mg/kg) |
|---|---|
| Pimavanserin | 3.288 |
| NH-K-A19005 | 1.01 |
| NH-K-A19006 | 0.2648 |
| NH-K-A19012 | 3.728 |

Note:
$ED_{50}$ represents the median effective dose.

3. DOI ((f)-1-(2,5-dimethoxy-4-iodophenyl)-2-aminopropane hydrochloride or (f)-2,5-dimethoxy-4-iodoamphetamine hydrochloride) induced PPI impairment effect test in rats 3.1 Test Method Intervention Test:

30 min after the intragastric administration of a drug (or a vehicle) and 30 min after the subcutaneous injection of DOI at 0.5 mg/kg at the neck, namely 60 min after the intragastric administration, the rats were placed into a startle reflex test box for testing.

The test was performed according to literature and preliminary experiments, and the specific process was as follows: first an adaptation period of 5 min was given (62 dB background sound), and 5 separate startle reflex stimuli were given after the adaptation period (blockl, results not included in the analysis to reduce the initial response of the animals to a plateau level), followed by 4 different types of tests (block2) presented in a pseudo-random manner, namely: 1) startle reflex stimulus alone (pulse-alone, 120 dB, lasting 20 ms); 2) prepulse stimulus alone 13 dB above the background sound (prepulse-alone, 75 dB, lasting 20 ms); 3) prepulse stimulus in combination with startle reflex stimulus, each lasting 20 ms, with an interval of 100 ms; and 4) no stimulus in which only the background sound was given (no stimulus). Each trial was performed 5 times, with an average interval of 20 s (10-30 s) between trials.

The response amplitude of the startle reflex stimulus alone or the prepulse stimulus in combination with startle reflex stimulus was expressed as the AVG (instrument-specific unit) value, which indirectly reflects the size of the flinching response of the rat body.

Evaluation index: PPI %=(1−response amplitude of prepulse stimulus in combination with startle reflex stimulus/response amplitude of startle reflex stimulus alone)×100. The higher the value is, the greater the degree of the inhibition is.

Dosing Test:

The DOI at 0.5 mg/kg administered to animals in the above groups was changed to normal saline (NS), and other operations including administration and testing were the same as those in the intervention test.

3.2 Experimental Results

PPI refers to the inhibitory effect on the startle reflex produced by a weak stimulus that precedes a strong shock reflex stimulus (30-500 ms). Studies have shown that the neuronal nuclei and pharmacological mechanisms that regulate PPI in humans and rodents are very similar, so that PPI is a cross-species behavioral indicator. Clinical studies have also found that patients with schizophrenia have PPI impaired, which can be improved by some antipsychotic drugs. Based on the above characteristics, this model is widely used to study the pathogenesis of schizophrenia and the pharmacological action of antipsychotic drugs, and is also used as a tool for screening antipsychotic drugs, especially for predicting the efficacy on negative symptoms and cognitive disorder of schizophrenia.

In this experiment, the administration of DOI at 0.5 mg/kg can significantly destroy PPI ($P<0.05$) in rats, and the administration of NH-K-A19006 at 0.3 mg/kg, NH-K-A19005 at 3 mg/kg and pimavanserin at 3 mg/kg can significantly reverse the DOI-induced PPI impairment in rats ($P<0.05$). The detailed results are shown in the table below. In the table, "MEAN" represents mean value, "SD" represents standard deviation, and "P" represents P value. The values in the table represent reversal of the impairment, where a larger value indicates a greater relief in symptoms as compared to the model group.

This study showed that NH-K-A19006 at 0.3 mg/kg and NH-K-A19005 at 3 mg/kg could significantly reverse the DOI-induced PPI impairment in rats, and no significant effects were seen in normal rats at the above doses, suggesting that NH-K-A19005 and NH-K-A19006 are effective on psychiatric diseases and are effective on negative symptoms and cognitive disorder of schizophrenia.

TABLE 6

Effect of NH-K-A19006 on 0.5 mg/kg DOI-induced PPI impairment in rats

| | DOI 0.5 mg/kg | | | |
|---|---|---|---|---|
| Animal No. | Model | NH-K-A19006 0.3 mg/kg | NH-K-A19006 0.1 mg/kg | NH-K-A19006 0.03 mg/kg |
| 1 | 1.04 | 39.78 | 10.18 | 20.87 |
| 2 | 38.22 | 22.65 | 65.40 | 38.06 |
| 3 | 5.94 | 60.53 | 12.46 | 49.78 |
| 4 | 20.35 | 60.18 | 51.33 | 58.97 |
| 5 | −4.12 | 56.91 | 38.29 | 53.17 |
| 6 | 29.97 | 67.62 | 47.73 | 2.79 |
| 7 | 58.89 | 85.73 | 47.53 | 32.00 |
| 8 | 7.72 | 7.56 | 74.93 | 8.44 |
| MEAN | 19.75 | 50.12 | 43.48 | 33.01 |
| SD | 21.49 | 25.36 | 22.88 | 20.88 |
| P | 0.023 | 0.022 | 0.051 | 0.231 |

Note:
model group vs. blank group; and each administration group vs. model group.

TABLE 7

| Effect of pimavanserin and NH-K-A19005 on 0.5 mg/kg DOI-induced PPI impairment in rats | | | | | | | |
|---|---|---|---|---|---|---|---|
| | DOI 0.5mg/kg | | | | | | |
| | Model | Pimavanserin | | | A19005 | | |
| Dose (mg/kg) | 0 | 10 | 3 | 1 | 10 | 3 | 1 |
| Animal No. 1 | 27.03 | 33.19 | 62.41 | 55.33 | 52.03 | 38.90 | 11.24 |
| Animal No. 2 | 33.59 | 55.00 | 75.59 | 41.86 | 43.86 | 23.16 | 71.74 |
| Animal No. 3 | 32.13 | 69.36 | 25.79 | 30.19 | 86.67 | 36.23 | 55.27 |
| Animal No. 4 | 40.14 | 54.29 | 45.06 | 7.34 | 28.57 | 53.57 | 13.13 |
| Animal No. 5 | 15.53 | 71.90 | 35.48 | 12.78 | 78.84 | 36.93 | 49.29 |
| Animal No. 6 | 0.00 | 24.73 | 4.10 | −9.80 | 65.78 | 47.37 | 40.22 |
| Animal No. 7 | -4.14 | 32.57 | 30.23 | 36.56 | 63.08 | 45.54 | |
| Animal No. 8 | 23.97 | 37.52 | 62.54 | 57.19 | 0.38 | 61.94 | |
| MEAN | 21.03 | 47.32 | 42.65 | 28.93 | 52.40 | 42.95 | 40.15 |
| SD | 16.02 | 17.81 | 23.46 | 23.75 | 28.07 | 11.89 | 23.98 |
| P | 0.000 | 0.008 | 0.049 | 0.448 | 0.016 | 0.008 | 0.098 |

Note:
model group vs. blank group; and each administration group vs. model group.

TABLE 8

| Effect of NH-K-A19006 on PPI in normal rats | | | | |
|---|---|---|---|---|
| | Normal saline | | | |
| Animal No. | Blank | NH-K-A19006 0.3 mg/kg | NH-K-A19006 0.1 mg/kg | NH-K-A19006 0.03 mg/kg |
| 1 | 29.93 | 65.07 | 50.53 | 74.39 |
| 2 | 55.30 | 16.28 | 89.95 | 87.22 |
| 3 | 26.14 | 62.68 | 60.40 | 43.35 |
| 4 | 45.95 | 47.76 | 60.40 | 81.41 |
| 5 | 35.39 | 42.79 | 81.41 | 91.96 |
| 6 | 64.88 | 68.71 | 77.50 | 55.90 |
| 7 | 39.64 | 70.20 | 71.96 | 54.35 |
| 8 | 41.15 | 55.52 | 69.71 | 60.94 |
| MEAN | 42.30 | 53.62 | 70.23 | 68.69 |
| SD | 12.89 | 17.99 | 12.83 | 17.53 |
| P | | 0.170 | 0.001 | 0.004 |

Note:
each administration group vs. blank group.

TABLE 9

| Effect of pimavanserin and NH-K-A19005 on PPI in normal rats | | | | | | | |
|---|---|---|---|---|---|---|---|
| | NS (normal saline) | | | | | | |
| | Blank | Pimavanserin | | | A19005 | | |
| Dose (mg/kg) | 0 | 10 | 3 | 1 | 10 | 3 | 1 |
| Animal No. 1 | 61.08 | −32.12 | 71.78 | 83.93 | 72.39 | 38.56 | 52.82 |
| Animal No. 2 | 58.56 | 72.74 | 84.89 | 70.62 | 61.37 | 48.95 | 71.15 |
| Animal No. 3 | 82.04 | 72.49 | 63.88 | 68.32 | 81.26 | 56.22 | 68.46 |
| Animal No. 4 | 84.10 | 83.19 | 76.95 | 14.80 | 55.11 | 59.36 | 80.68 |
| Animal No. 5 | 60.90 | 80.13 | 37.54 | 45.96 | 96.41 | 82.61 | 15.47 |
| Animal No. 6 | 48.49 | 44.91 | 42.51 | 67.95 | 53.03 | 79.48 | 49.79 |
| Animal No. 7 | 50.66 | 82.49 | 64.49 | 61.11 | 84.89 | 48.75 | |
| Animal No. 8 | 90.19 | 52.16 | 42.29 | 92.15 | 84.43 | 42.42 | |
| MEAN | 67.00 | 57.00 | 60.54 | 63.11 | 73.61 | 57.04 | 56.40 |
| SD | 16.08 | 38.67 | 17.74 | 23.95 | 15.77 | 16.27 | 23.17 |
| P | | 0.510 | 0.458 | 0.708 | 0.420 | 0.238 | 0.330 |

Note:
each administration group vs. blank group.

The invention claimed is:

1. A compound of formula I:

I

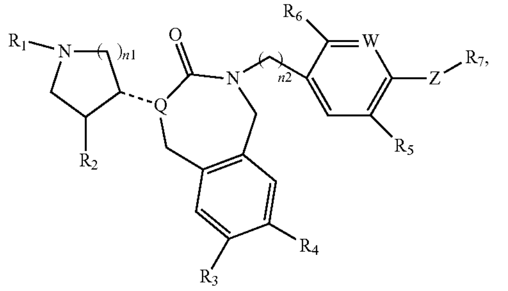

wherein in formula I:

n1 and n2 are independently integers of 1-3;

$R_1$ is selected from C1-C8 linear or branched alkyl, C2-C8 alkenyl, and C2-C8 alkynyl, wherein the alkyl, alkenyl and alkynyl are each independently and optionally substituted with substituents selected from halogen and C1-C8 haloalkyl;

$R_2$ is selected from hydrogen, halogen and C1-C8 haloalkyl;

$R_3$, $R_4$, $R_5$ and $R_6$ are each independently selected from hydrogen, halogen, and C1-C8 haloalkyl;

$R_7$ is selected from C1-C8 linear or branched alkyl, cycloalkyl, and

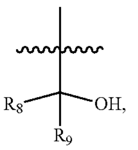

wherein $R_8$ and $R_9$ are each independently selected from C1-C8 linear or branched alkyl, and the alkyl and cycloalkyl are optionally substituted with substituents selected from halogen and C1-C8 haloalkyl;

Z is selected from C, O and N;

Q and W are each independently selected from C and N; and the symbol ------ represents absence of a bond or is a single bond;

when the symbol ------ represents the absence of a bond, the compound of formula I is a compound of formula II:

II

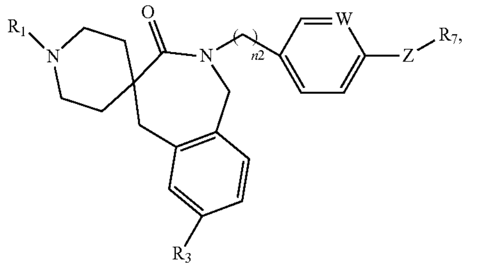

or when the symbol ------ is a single bond, the compound of formula I is a compound of formula III:

III

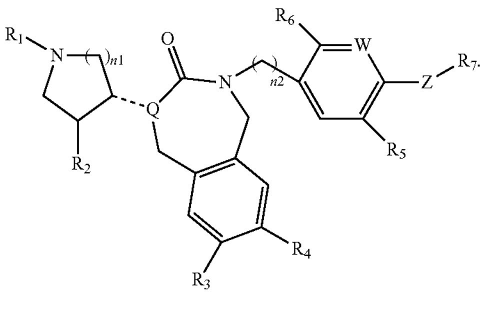

2. The compound of formula I according to claim 1, wherein, $R_1$ is selected from C1-C5 linear or branched alkyl, C2-C5 alkenyl, and C2-C5 alkenyl, wherein the alkyl, alkenyl and alknyl are each independently and optionally substituted with substituents selected from halogen and C1-C5 haloalkyl, or $R_2$ is selected from hydrogen, halogen, and C1-C5 haloalkyl; or $R_3$, $R_4$, $R_5$ and $R_6$ are each independently selected from hydrogen, halogen, and C1-C5 haloalkyl; or $R_7$ is selected from C1-C5 linear or branched alkyl, $C_3$-$C_{10}$ cycloalkyl, and

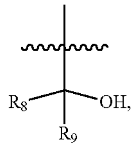

wherein $R_8$ and $R_9$ are each independently selected from C1-C5 linear or branched alkyl, and the alkyl and cycloalkyl are optionally substituted with substituents selected from halogen and C1-C5 haloalkyl.

3. The compound of formula I according to claim 1, wherein the halogen in a substitute group selected from $R_1$ to $R_9$ is independently fluorine, chlorine, bromine, or iodine.

4. The compound of formula I according to claim 2, wherein:

an alkyl in the C1-C5 linear or branched alkyl is methyl, ethyl, propyl, isopropyl, butyl, isobutyl, pentyl, or isopentyl;

the cycloalkyl is cyclopropyl, cyclobutyl, or cyclopentyl.

5. The compound of formula I according to claim 1, wherein:

Z is O, $R_1$ is C1-C5 linear or branched alkyl;

$R_2$ is selected from hydrogen and halogen;

$R_3$, $R_4$, $R_5$ and $R_6$ are each independently selected from hydrogen and halogen; and $R_7$ is selected from C1-C5 linear or branched alkyl and C3-C6 cycloalkyl.

6. The compound of formula I according to claim 1, wherein the compound of formula I is a compound of formula I-1:

I-1

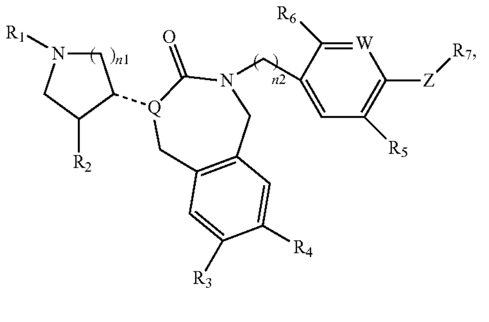

wherein:

$R_1$ is C1-C5 linear or branched alkyl;

$R_2$ is selected from hydrogen and halogen;

$R_3$, $R_4$, $R_5$ and $R_6$ are each independently selected from hydrogen and halogen;

$R_7$ is selected from C1-C5 linear or branched alkyl and C3-C6 cycloalkyl; and

Q is N.

7. The compound of formula I according to claim 1, wherein the compound of formula I is a compound of formula IV:

IV

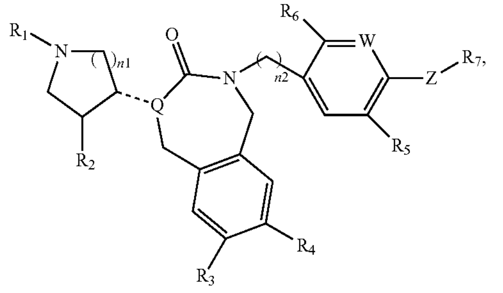

wherein: n1 and n2 are independently integers of 1-3;

$R_1$ is selected from methyl, ethyl, propyl, and butyl;

$R_2$ is selected from hydrogen, fluorine, chlorine, bromine, and iodine;

$R_3$, $R_4$, $R_5$ and $R_6$ are each independently selected from hydrogen, fluorine, and chlorine; and $R_7$ is selected from isopropyl, isobutyl, ethyl, propyl, methyl, cyclopropyl, cyclobutyl, and

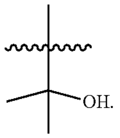 [SMILES: *C(C)(C)O]

8. The compound of formula I according to claim 1, wherein the compound of formula I is a compound of formula V:

V

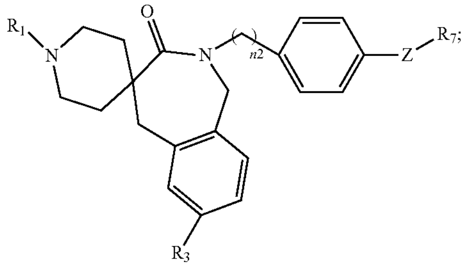

wherein n2 is an integer of 1-2;

$R_1$ is selected from methyl, ethyl, propyl, and butyl;

$R_3$ is selected from hydrogen, fluorine, and chlorine; and $R_7$ is selected from isopropyl, isobutyl, ethyl, propyl, methyl, cyclopropyl, cyclobutyl, and

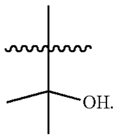 [SMILES: *C(C)(C)O]

9. The compound of formula I according to claim 1, wherein the compound of formula I is a compound of formula VI:

VI

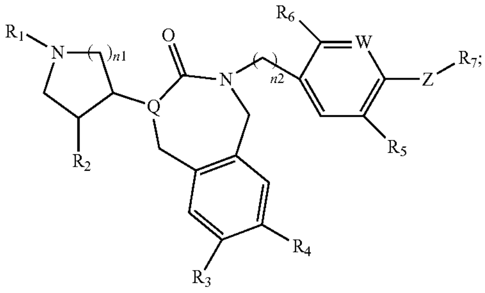

wherein n1 and n2 are independently integers of 1-3;

$R_1$ is methyl;

$R_2$ is selected from fluorine and hydrogen;

$R_3$, $R_4$, $R_5$ and $R_6$ are each independently selected from hydrogen, fluorine, and chlorine;

$R_7$ is selected from isopropyl, cyclopropyl, isobutyl, methyl, and

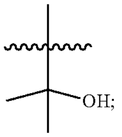 [SMILES: *C(C)(C)O]

Z is selected from C, O and N; and

Q and W are each independently selected from C and N.

10. The compound of formula I according to claim 1, selected from the following compounds:

A19020

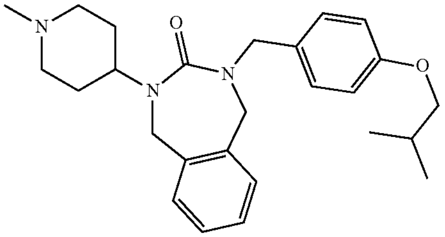

;

A19001

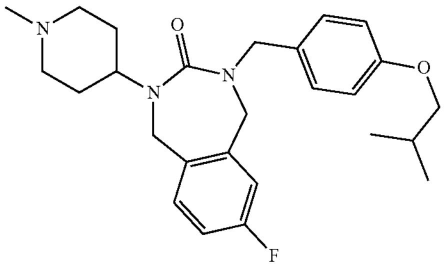

;

-continued
A190017
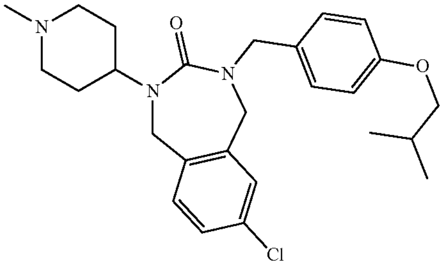
;
A19005
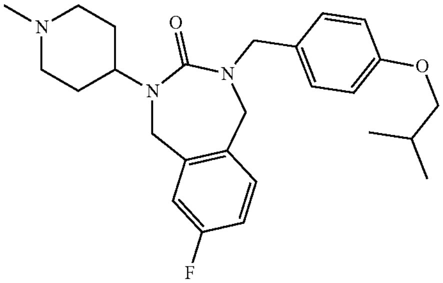
;
A19007
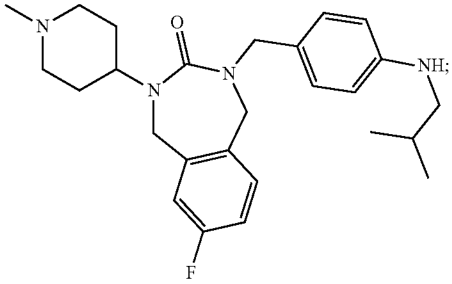
;
A19006
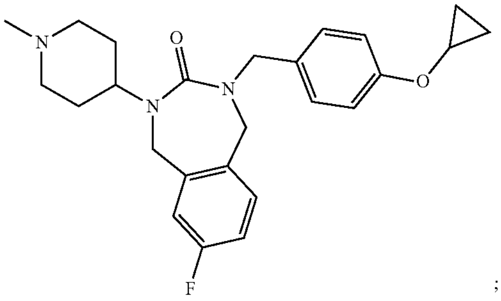
;
A19008
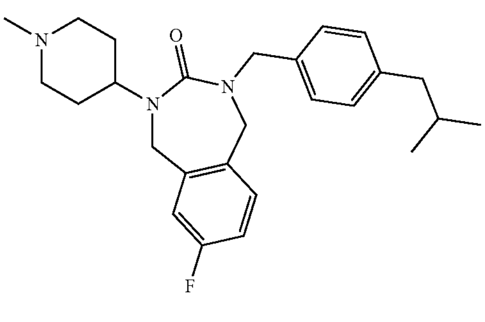
;
-continued
A19009
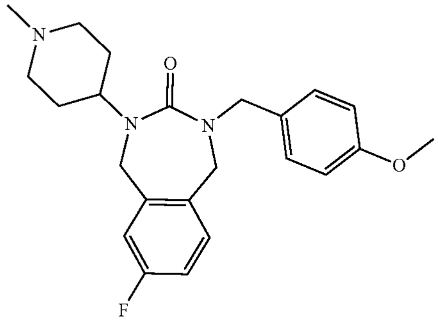
;
A19011
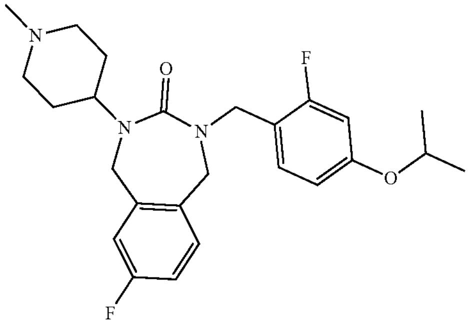
;
A19012
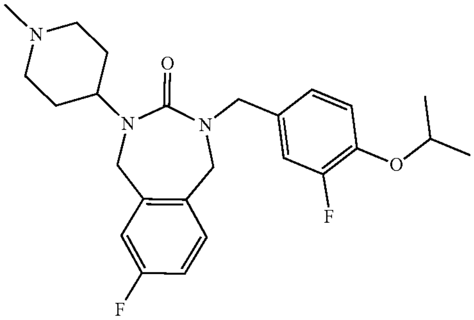
;
A19013
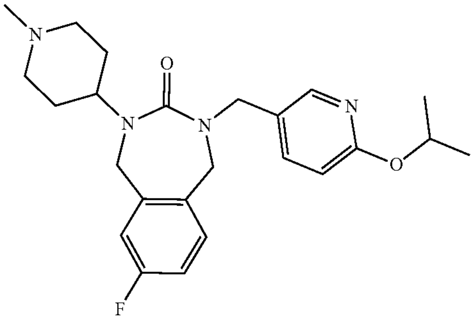
;

-continued

A19015

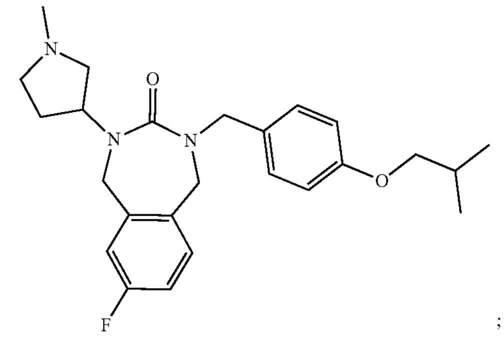

;

A19019

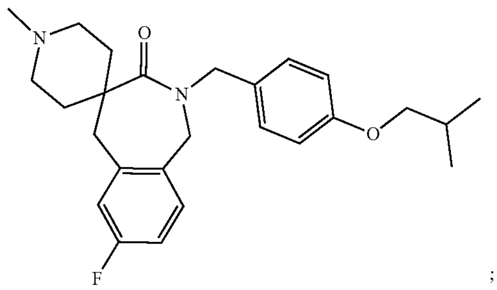

;

A19014-0

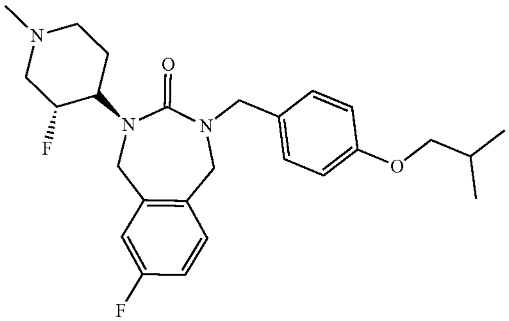

;

A19014-0A

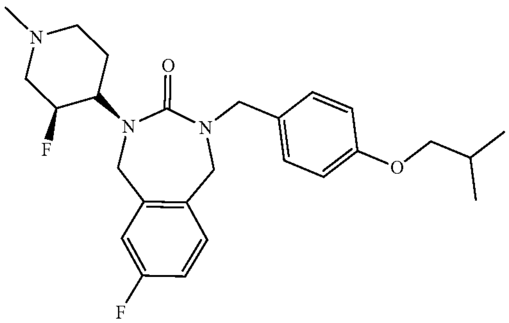

;

-continued

A20001

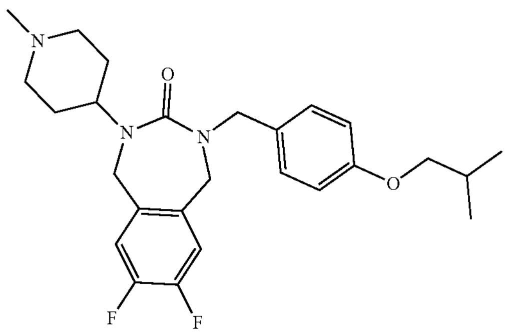

;

A19010

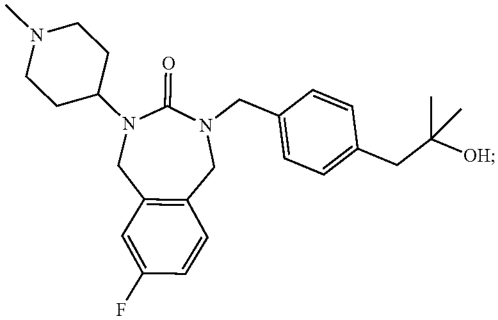

; and

A19022

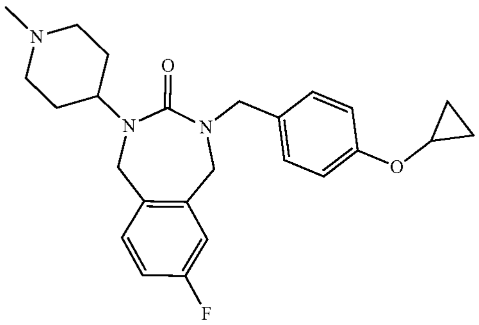

.

11. A pharmaceutical composition, comprising the compound according to claim 1, a pharmaceutically acceptable excipient, carrier, adjuvant, or vehicle.

12. A method for treating a psychiatric disease, comprising administering an effective amount of a medicament comprising the compound of claim 1 to a subject in need thereof, wherein the psychiatric disease is schizophrenia, Parkinson's disease, behavioral symptom of dementia, or psychological symptom of dementia.

13. A method for treating a psychiatric disease, comprising administering an effective amount of the pharmaceutical composition of claim 11 to a subject in need thereof, wherein the psychiatric disease is schizophrenia, Parkinson's disease, behavioral symptom of dementia, or psychological symptom of dementia.

* * * * *